US012686884B2

(12) United States Patent
Gibbons

(10) Patent No.: US 12,686,884 B2
(45) Date of Patent: Jul. 21, 2026

(54) COMPOSITIONS, SYSTEMS AND METHODS FOR CRISPR-BASED ENZYME OPTIMIZATION

(71) Applicant: 10x Genomics, Inc., Pleasanton, CA (US)

(72) Inventor: Michael Gibbons, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 539 days.

(21) Appl. No.: 18/312,914

(22) Filed: May 5, 2023

(65) Prior Publication Data

US 2024/0002901 A1      Jan. 4, 2024

Related U.S. Application Data

(60) Provisional application No. 63/339,267, filed on May 6, 2022.

(51) Int. Cl.
*C12Q 1/48* (2006.01)
*C12N 9/12* (2006.01)

(52) U.S. Cl.
CPC .............. *C12Q 1/485* (2013.01); *C12N 9/12* (2013.01)

(58) Field of Classification Search
CPC ................................. C12Q 1/485; C12N 9/12
See application file for complete search history.

(56) References Cited

U.S. PATENT DOCUMENTS 6,265,552 B1     7/2001  Schatz
10,428,326 B2   10/2019  Belhocine et al.

10,550,429 B2     2/2020  Harada et al.
2010/0105112 A1   4/2010  Holtze et al.
2014/0155295 A1   6/2014  Hindson et al.
2014/0378345 A1  12/2014  Hindson et al.
(Continued)

FOREIGN PATENT DOCUMENTS

WO     2014210353 A2   12/2014
WO     2018075693 A1    4/2018
(Continued)

OTHER PUBLICATIONS

Sambrook et al., "Molecular Cloning: A Laboratory Manual". Third Edition, Cold Spring Harbor Laboratory Press, Cold Spring Harbor, New York, 2000. 2,272 pages.
(Continued)

*Primary Examiner* — David W Berke-Schlessel
*Assistant Examiner* — Trent R Clarke
(74) *Attorney, Agent, or Firm* — Saul Ewing LLP; Justin W. Crotty; Thomas Murray

(57) ABSTRACT

Provided herein are reaction mixtures, compositions, systems, methods, and kits for assessing enzymatic activity. Aspects of the disclosure include use of a reactant barcoded oligonucleotide (RBO) construct comprising a first oligonucleotide comprising a reaction barcode sequence and a first linker that connects the first oligonucleotide to a first reactant, an amplification construct comprising a second oligonucleotide that is complementary to at least a portion of the first oligonucleotide and a second linker that connects the second oligonucleotide to a second reactant, and a blocking construct, comprising a third oligonucleotide that is complementary to at least a portion of the first oligonucleotide. A rate of reaction product generation may be measured to determine an enzymatic activity of a given enzyme.

22 Claims, 23 Drawing Sheets

(56)     References Cited

U.S. PATENT DOCUMENTS

| | | |
|---|---|---|
| 2015/0376609 A1 | 12/2015 | Hindson et al. |
| 2018/0105808 A1 | 4/2018 | Mikkelsen et al. |
| 2019/0064173 A1 | 2/2019 | Bharadwaj et al. |
| 2019/0100632 A1 | 4/2019 | Delaney et al. |
| 2019/0177800 A1 | 6/2019 | Boutet et al. |
| 2019/0323088 A1 | 10/2019 | Boutet et al. |
| 2019/0367969 A1 | 12/2019 | Belhocine et al. |
| 2019/0367997 A1 | 12/2019 | Bent et al. |

FOREIGN PATENT DOCUMENTS

| | | |
|---|---|---|
| WO | 2018119447 A2 | 6/2018 |
| WO | 2019040637 A1 | 2/2019 |
| WO | 2019165181 A1 | 8/2019 |
| WO | 2020167862 A1 | 8/2020 |
| WO | 2020185791 A1 | 9/2020 |

OTHER PUBLICATIONS

Hughes et al., "Choose Your Label Wisely: Water-Soluble Fluorophores Often Interact with Lipid Bilayers," PLoS ONE 9(2): e87649, https://doi.org/10.1371/journal.pone.0087649, Feb. 4, 2014, 8 pages.

Fang et al., "Fluoride-cleavable biotinylation phosphoramidite for 5'-end-labelling and affinity purification of synthetic oligonucleotides," Nucleic Acids Research, 2003, vol. 31, No. 2, pp. 708-715.

Longwell et al., "High-throughput screening technologies for enzyme engineering," Science Direct, Current Opinion in Biotechnology, vol. 48, Dec. 2017, pp. 196-202.

Goddard et al., "Enzyme assays for high-throughput screening," Science Direct, Current Opinion in Biotechnology, vol. 15, Issue 4, Aug. 2004, pp. 314-322.

100

110

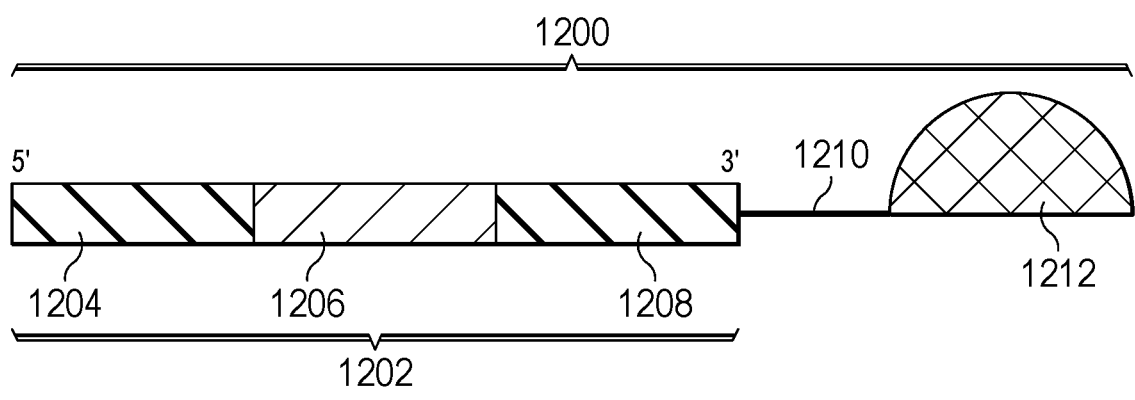
FIG. 12A
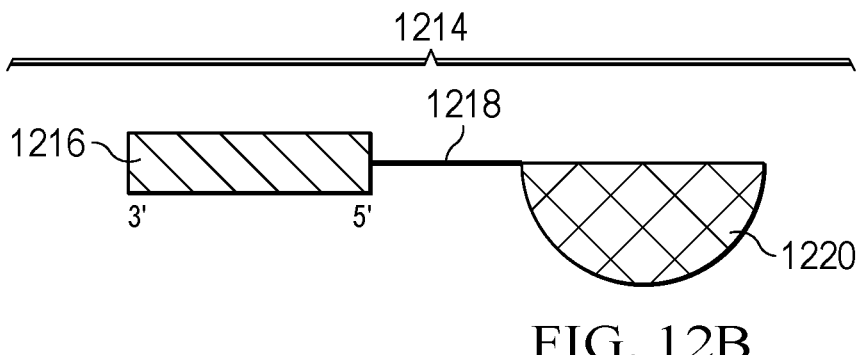
FIG. 12B
FIG. 12C

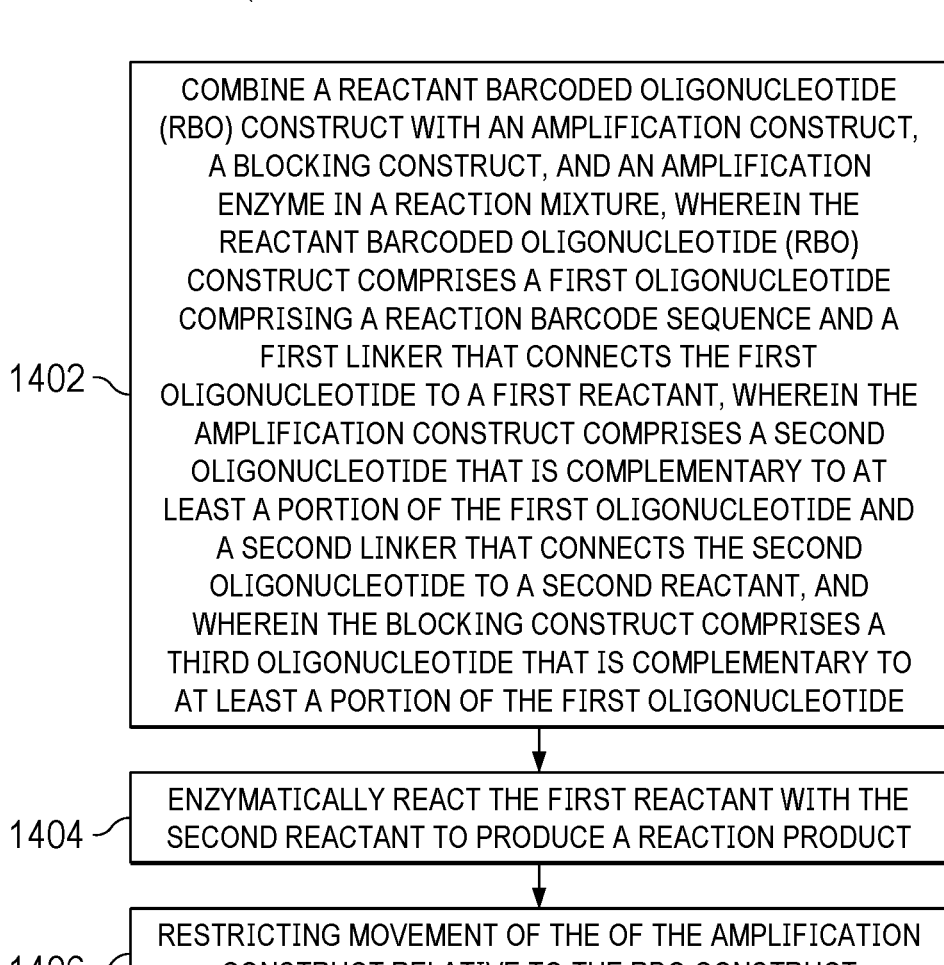

1400

1402 — COMBINE A REACTANT BARCODED OLIGONUCLEOTIDE (RBO) CONSTRUCT WITH AN AMPLIFICATION CONSTRUCT, A BLOCKING CONSTRUCT, AND AN AMPLIFICATION ENZYME IN A REACTION MIXTURE, WHEREIN THE REACTANT BARCODED OLIGONUCLEOTIDE (RBO) CONSTRUCT COMPRISES A FIRST OLIGONUCLEOTIDE COMPRISING A REACTION BARCODE SEQUENCE AND A FIRST LINKER THAT CONNECTS THE FIRST OLIGONUCLEOTIDE TO A FIRST REACTANT, WHEREIN THE AMPLIFICATION CONSTRUCT COMPRISES A SECOND OLIGONUCLEOTIDE THAT IS COMPLEMENTARY TO AT LEAST A PORTION OF THE FIRST OLIGONUCLEOTIDE AND A SECOND LINKER THAT CONNECTS THE SECOND OLIGONUCLEOTIDE TO A SECOND REACTANT, AND WHEREIN THE BLOCKING CONSTRUCT COMPRISES A THIRD OLIGONUCLEOTIDE THAT IS COMPLEMENTARY TO AT LEAST A PORTION OF THE FIRST OLIGONUCLEOTIDE

1404 — ENZYMATICALLY REACT THE FIRST REACTANT WITH THE SECOND REACTANT TO PRODUCE A REACTION PRODUCT

1406 — RESTRICTING MOVEMENT OF THE OF THE AMPLIFICATION CONSTRUCT RELATIVE TO THE RBO CONSTRUCT

1408 — GENERATE A REVERSE COMPLEMENT OF THE REACTION BARCODE SEQUENCE WITH AN AMPLIFICATION ENZYME

FIG. 14

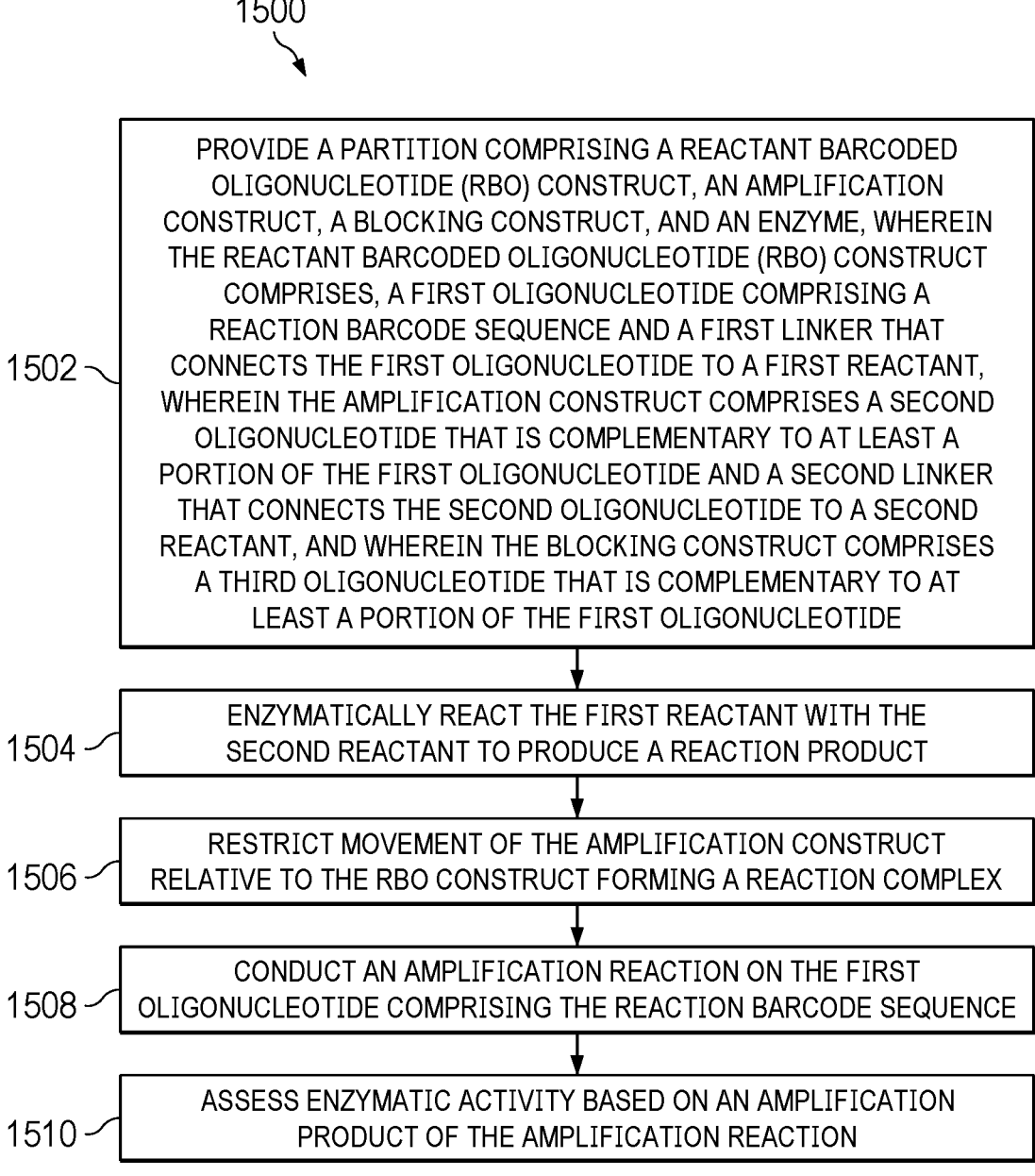

1500

1502 — PROVIDE A PARTITION COMPRISING A REACTANT BARCODED OLIGONUCLEOTIDE (RBO) CONSTRUCT, AN AMPLIFICATION CONSTRUCT, A BLOCKING CONSTRUCT, AND AN ENZYME, WHEREIN THE REACTANT BARCODED OLIGONUCLEOTIDE (RBO) CONSTRUCT COMPRISES, A FIRST OLIGONUCLEOTIDE COMPRISING A REACTION BARCODE SEQUENCE AND A FIRST LINKER THAT CONNECTS THE FIRST OLIGONUCLEOTIDE TO A FIRST REACTANT, WHEREIN THE AMPLIFICATION CONSTRUCT COMPRISES A SECOND OLIGONUCLEOTIDE THAT IS COMPLEMENTARY TO AT LEAST A PORTION OF THE FIRST OLIGONUCLEOTIDE AND A SECOND LINKER THAT CONNECTS THE SECOND OLIGONUCLEOTIDE TO A SECOND REACTANT, AND WHEREIN THE BLOCKING CONSTRUCT COMPRISES A THIRD OLIGONUCLEOTIDE THAT IS COMPLEMENTARY TO AT LEAST A PORTION OF THE FIRST OLIGONUCLEOTIDE

1504 — ENZYMATICALLY REACT THE FIRST REACTANT WITH THE SECOND REACTANT TO PRODUCE A REACTION PRODUCT

1506 — RESTRICT MOVEMENT OF THE AMPLIFICATION CONSTRUCT RELATIVE TO THE RBO CONSTRUCT FORMING A REACTION COMPLEX

1508 — CONDUCT AN AMPLIFICATION REACTION ON THE FIRST OLIGONUCLEOTIDE COMPRISING THE REACTION BARCODE SEQUENCE

1510 — ASSESS ENZYMATIC ACTIVITY BASED ON AN AMPLIFICATION PRODUCT OF THE AMPLIFICATION REACTION

FIG. 15

COMPOSITIONS, SYSTEMS AND METHODS FOR CRISPR-BASED ENZYME OPTIMIZATION

CROSS-REFERENCE TO RELATED APPLICATION

This application claims priority to and the benefit of U.S. Provisional Application 63/339,267, filed May 6, 2022, which is incorporated herein by reference in its entirety.

FIELD OF THE INVENTION

This description is generally directed towards reaction mixtures, compositions, systems, methods, and kits for enzyme detection and activity assays. The enzyme related assays can be used in conjunction with CRISPR-based enzyme modification methods as described. The description further includes reaction mixtures, compositions, systems, methods, and kits for enzyme modification and then detecting/assessing enzymatic function of the modified enzyme.

BACKGROUND

CRISPR/Cas machinery can be used to modify genomes of single cells and specific genes of interest. In particular, CRISPR gene editing is also useful for modifying the resulting polypeptide sequence of enzymes to optimize enzymatic activity for a specific or customized purpose or application. Unfortunately, once enzyme modification has occurred there are no currently existing technologies for detecting and assessing enzymatic activity on a small or single cell scale. Current enzymatic activity assays rely on bulk inputs requiring large quantities of enzymes and reactants resulting in a slow and costly process that is not commercially viable. As such, there is a need for technologies that can generate large pools of modified enzymes and then accurately measure enzymatic activity at a single cell level for each of those modified enzymes. The present disclosure addresses this and other needs.

SUMMARY

Aspects of the description include a reaction mixture for assessing enzymatic activity, in accordance with various embodiments. The reaction mixture may comprise a reactant barcoded oligonucleotide (RBO) construct. The RBO construct may comprise a first oligonucleotide comprising a reaction barcode sequence. The RBO construct may comprise a first linker that connects the first oligonucleotide to a first reactant. The reaction mixture may comprise an amplification construct. The amplification construct may comprise a second oligonucleotide that may be complementary to at least a portion of the first oligonucleotide. The amplification construct may comprise a second linker that connects the second oligonucleotide to a second reactant. The reaction mixture may comprise a blocking construct. The blocking construct may comprise a third oligonucleotide that may be complementary to at least a portion of the first oligonucleotide.

Aspects of the description include a method for assessing enzymatic activity, in accordance with various embodiments. The method may comprise combining a reactant barcoded oligonucleotide (RBO) construct with an amplification construct, a blocking construct, and an enzyme in a reaction mixture. The RBO construct may comprise a first oligonucleotide comprising a reaction barcode sequence.

The RBO construct may comprise a first linker that connects the first oligonucleotide to a first reactant. The amplification construct may comprise a second oligonucleotide that may be complementary to at least a portion of the first oligonucleotide. The amplification construct may comprise a second linker that connects the second oligonucleotide to a second reactant. The blocking construct may comprise a third oligonucleotide that may be complementary to at least a portion of the first oligonucleotide. The method may comprise enzymatically reacting the first reactant with the second reactant to produce a reaction product. The method may comprise restricting movement of the of the amplification construct relative to the RBO construct. The method may comprise generating a reverse complement of the reaction barcode sequence with an amplification enzyme.

Aspects of the description include a method of assessing enzymatic activity within a partition, in accordance with various embodiments. The method may comprise providing a partition comprising a reactant barcoded oligonucleotide (RBO) construct, an amplification construct, a blocking construct, and an enzyme. The RBO construct may comprise a first oligonucleotide. The first oligonucleotide may comprise a reaction barcode sequence and a first linker that connects the first oligonucleotide to a first reactant. The amplification construct may comprise a second oligonucleotide that may be complementary to at least a portion of the first oligonucleotide. The amplification construct may comprise a second linker that connects the second oligonucleotide to a second reactant. The blocking construct may comprise a third oligonucleotide that may be complementary to at least a portion of the first oligonucleotide. The method may comprise enzymatically reacting the first reactant with the second reactant to produce a reaction product. The method may comprise restricting movement of the of the amplification construct relative to the RBO construct forming a reaction complex. The method may comprise conducting an amplification reaction on the first oligonucleotide comprising the reaction barcode sequence. The method may comprise assessing enzymatic activity based on an amplification product of the amplification reaction.

Aspects of the description include a partition, in accordance with various embodiments. The partition may comprise a reactant barcoded oligonucleotide (RBO) construct. The RBO may comprise a first oligonucleotide comprising a reaction barcode sequence. The RBO may comprise a first linker that connects the first oligonucleotide to a first reactant. The partition may comprise an amplification construct. The amplification product may comprise a second oligonucleotide that may be complementary to at least a portion of the first oligonucleotide. The amplification product may comprise a second linker that connects the second oligonucleotide to a second reactant. The partition may comprise a blocking construct. The blocking construct may comprise a third oligonucleotide that may be complementary to at least a portion of the first oligonucleotide.

Aspects of the description include a kit, in accordance with various embodiments. The kit may comprise a reactant barcoded oligonucleotide (RBO) construct. The RBO construct may comprise a first oligonucleotide comprising a reaction barcode sequence. The RBO construct may comprise a first linker that connects the first oligonucleotide to a first reactant. The kit may comprise an amplification construct. The amplification construct may comprise a second oligonucleotide that may be complementary to at least a portion of the first oligonucleotide The amplification construct may comprise a second linker that connects the second oligonucleotide to a second reactant. The kit may comprise a blocking construct. The blocking construct may comprise a third oligonucleotide that may be complementary to at least a portion of the first oligonucleotide.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF FIGURES

The novel features of the technology are set forth with particularity in the appended claims. A better understanding of the features and advantages of the present technology will be obtained by reference to the following detailed description that sets forth illustrative embodiments, in which the principles of the technology are utilized, and the accompanying drawings (also "Figure" and "FIG." herein). The accompanying drawings are not intended to be drawn to scale. Like reference numbers and designations in the various drawings indicate like elements. For purposes of clarity, not every component can be labeled in every drawing. In the drawings:

4

FIG. 12A schematically illustrates an exemplary RBO construct for a reaction mixture for assessing enzymatic activity according to various embodiments.

FIG. 12B schematically illustrates an exemplary amplification construct for a reaction mixture for assessing enzymatic activity according to various embodiments.

FIG. 12C schematically illustrates an exemplary blocking construct for a reaction mixture for assessing enzymatic activity according to various embodiments.

Figure 12D:
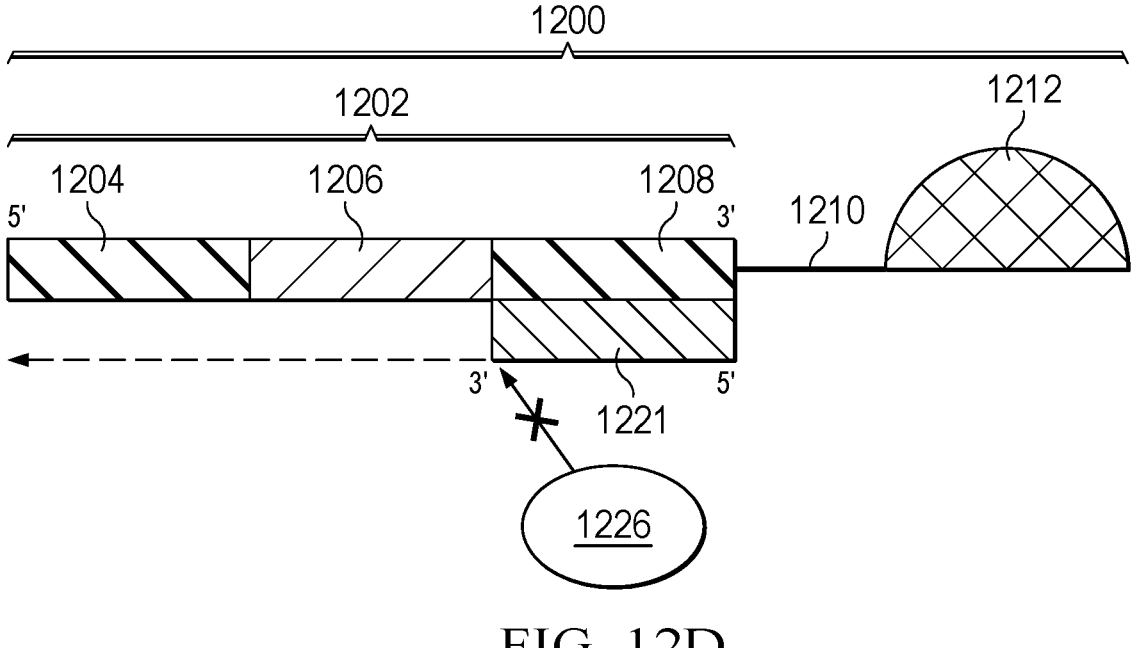

FIG. 12D schematically illustrates a blocking construct hybridized to an RBO construct for assessing enzymatic activity according to various embodiments.

Figure 12E:
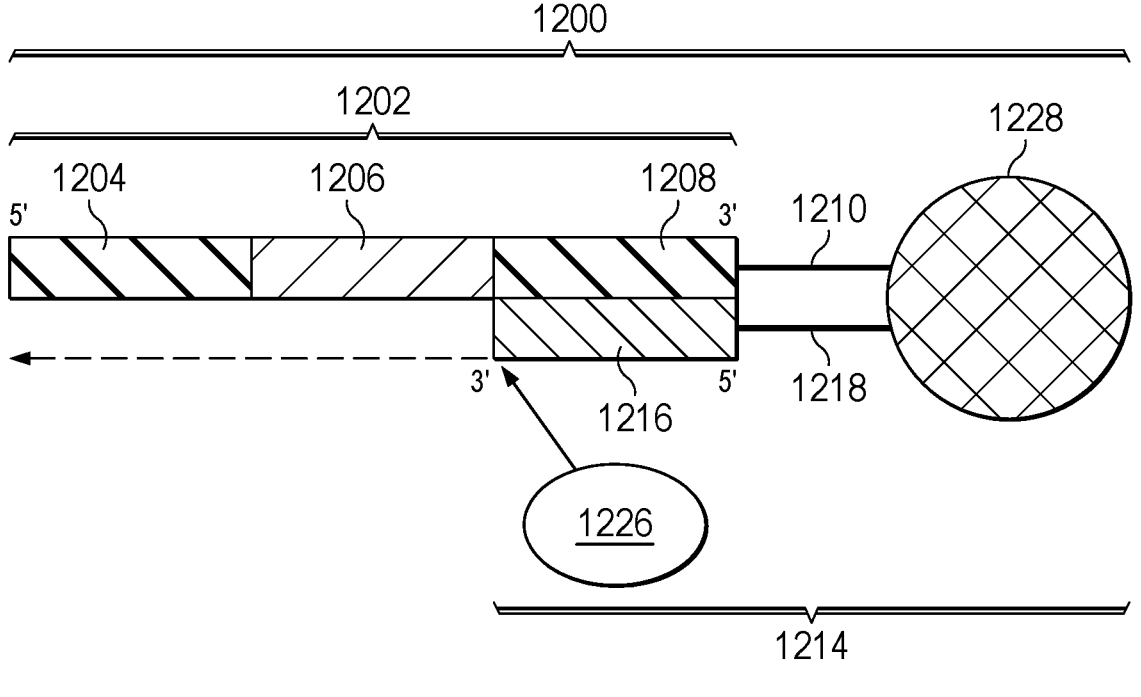

FIG. 12E schematically illustrates an amplification construct hybridized to an RBO construct for assessing enzymatic activity according to various embodiments.

Figure 12F:
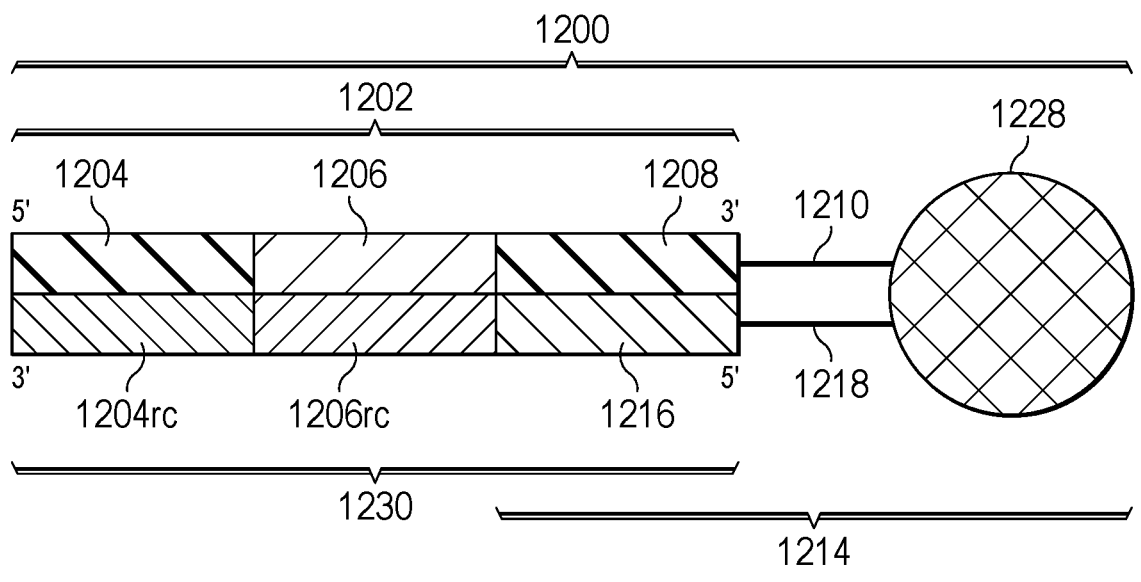

FIG. 12F schematically illustrates a completed extension product hybridized to a first oligonucleotide of an RBO construct in accordance with various embodiments.

Figure 12G:
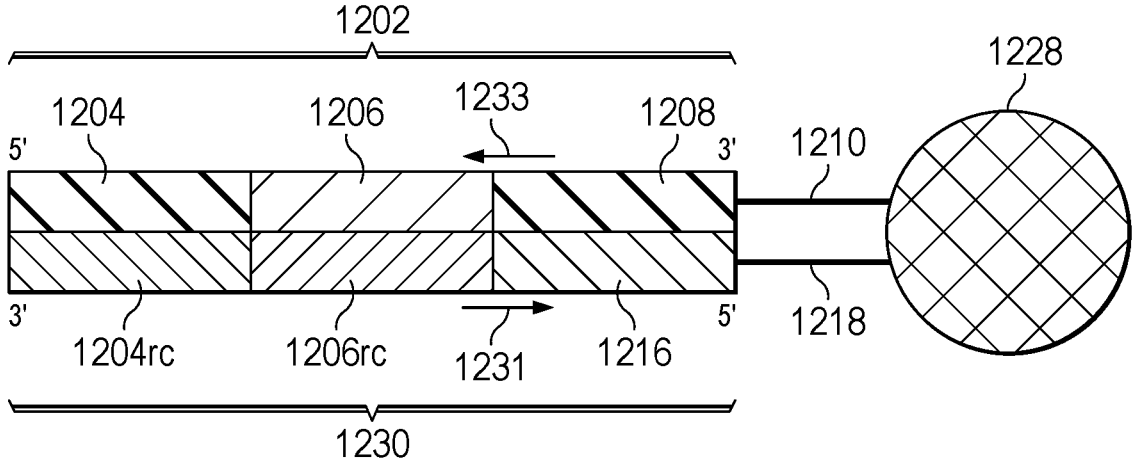

FIG. 12G schematically illustrates an amplification construct and an RBO construct that can be included in a reaction mixture for assessing enzymatic activity by amplifying a first oligonucleotide and an extension product in accordance with various embodiments.

Figure 12H:
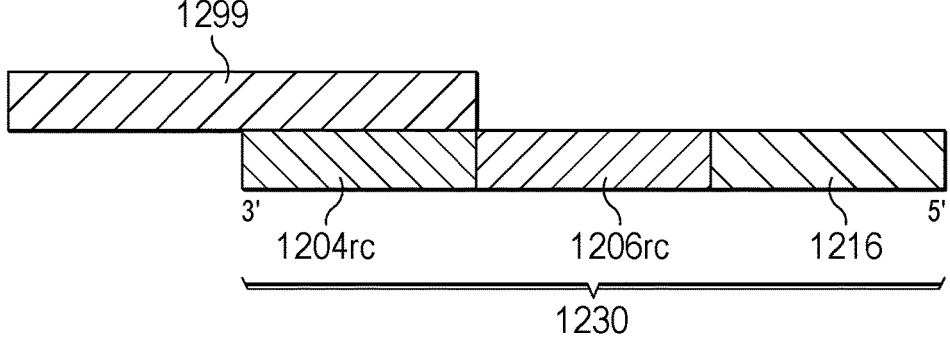

FIG. 12H schematically illustrates a non-limiting example of compositions that can be included in a reaction mixture for assessing enzymatic activity in accordance with various embodiments.

Figure 12I:
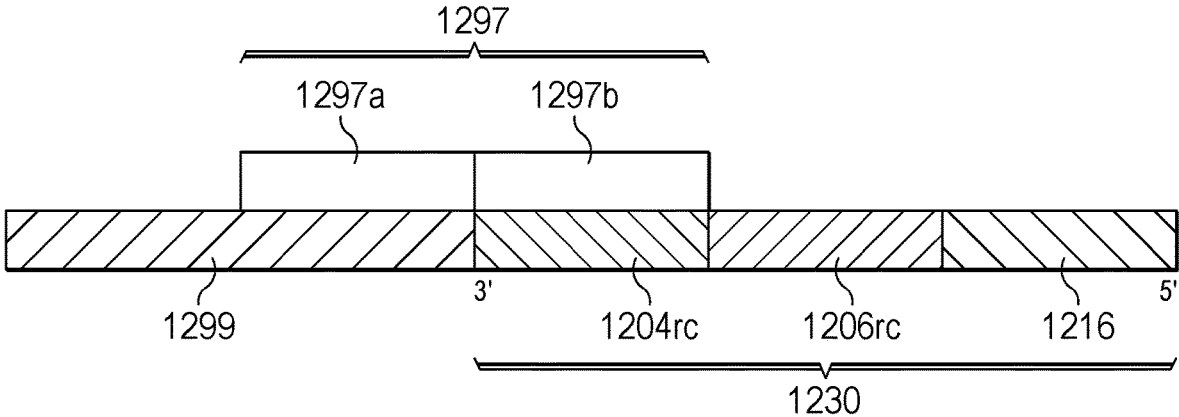

FIG. 12I schematically illustrates a non-limiting example of compositions that can be included in a reaction mixture for assessing enzymatic activity in accordance with various embodiments.

Figure 12J:
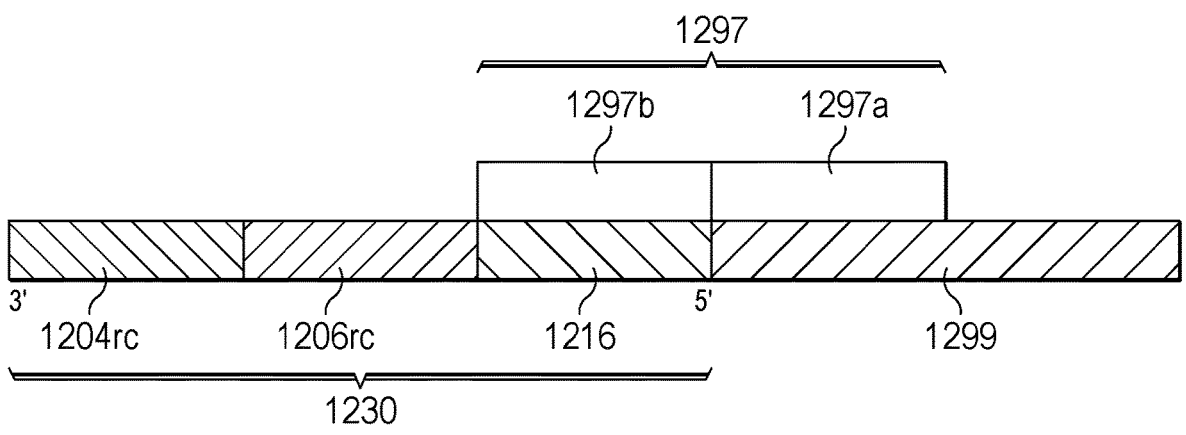

FIG. 12J schematically illustrates a non-limiting example of compositions that can be included in a reaction mixture for assessing enzymatic activity in accordance with various embodiments.

Figure 12K:
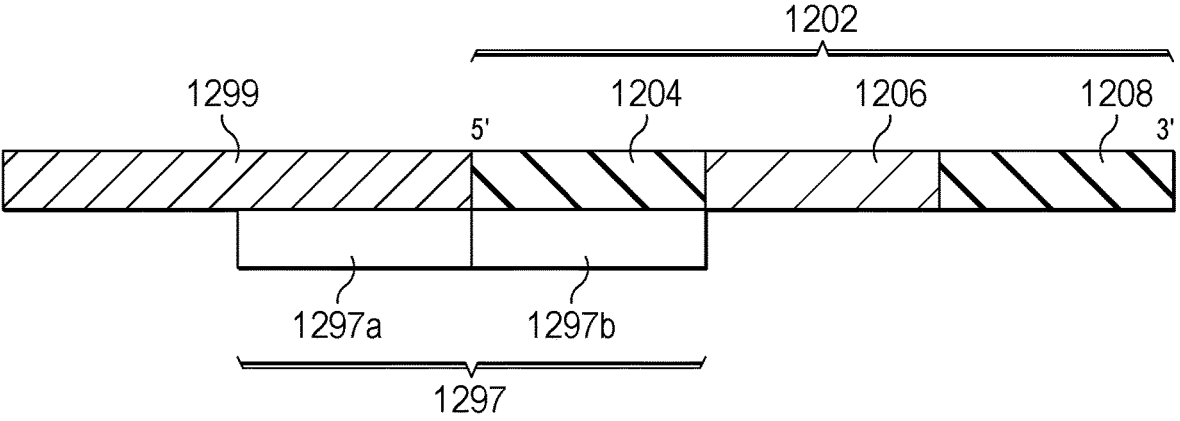

FIG. 12K schematically illustrates another non-limiting example of compositions that can be included in a reaction mixture for assessing enzymatic activity in accordance with various embodiments.

Figure 12L:
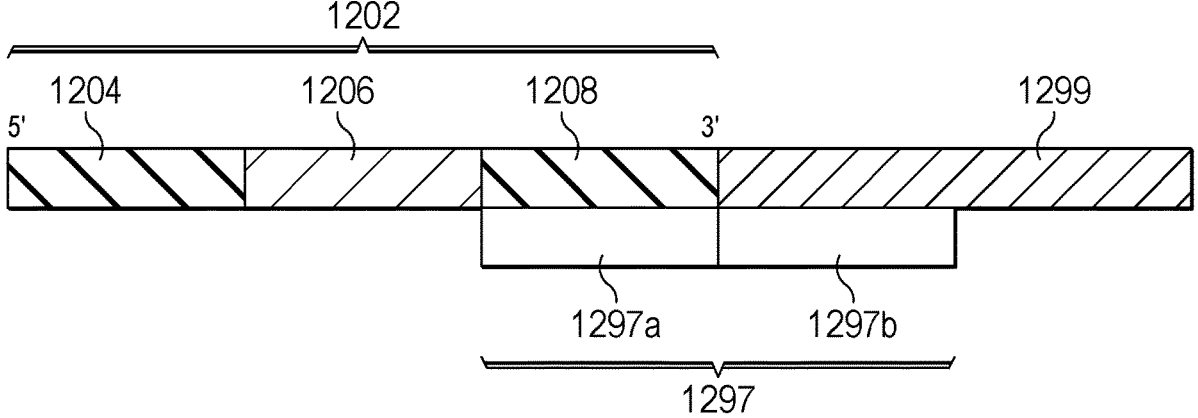

FIG. 12L schematically illustrates a non-limiting example of compositions that can be included in a reaction mixture for assessing enzymatic activity in accordance with various embodiments.

Figure 13:
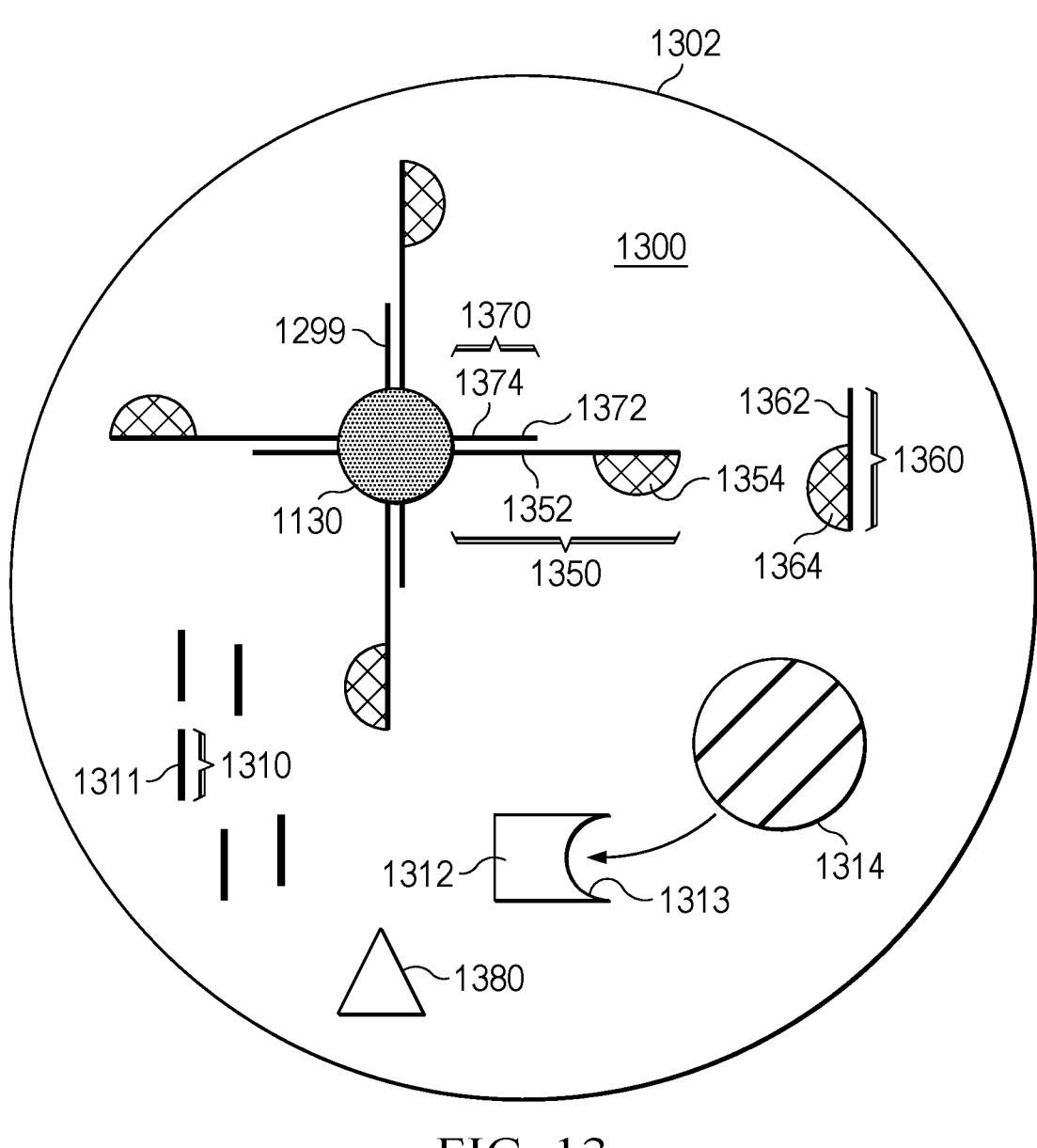

FIG. 13 illustrates reaction mixture comprising a partition (e.g., a droplet) including a bead associated with an RBO construct in accordance with various embodiments.

FIG. 14 illustrates steps in a method for assessing enzymatic activity according to various embodiments.

FIG. 15 illustrates steps in a method for assessing enzymatic activity according to various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

This specification describes various exemplary embodiments of technologies for detecting and assessing enzymatic activity. In some aspects, one or more enzymes can be modified to generate many different variants using CRISPR gene editing or other technologies and then the modified enzymes can be screened. Such technologies enable researchers and medical practitioners to optimize an enzymatic activity for a specific application. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

It should be understood that any uses of subheadings herein are for organizational purposes and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary descriptions of specific features are used, largely for informational purposes, and not in any way to limit the design, subfeature, and functionality of the specifically described feature.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those available and commonly used in the art.

I. Definitions

The term "3' end blocker," "PCR blocker," or "PCR blocker oligonucleotides" may be used interchangeably and, as used herein, generally refer to one or more oligonucleotides that can be naturally occurring or can be modified to inhibit a polymerase during the elongation step of a polymerase chain reaction. In various embodiments disclosed herein, 3' end blockers lack a hydroxyl group at the 3' end required for extension in PCR. There are a variety of 3' end blockers known in the art, which may include, without limitation, 3' spacers, 3' phosphates, dideoxy cytidines (ddCs), and 3' inverted ends.

The terms "adapter(s)", "adaptor(s)" and "tag(s)" may be used synonymously. An adapter or tag can be coupled to a polynucleotide sequence to be "tagged" by any approach, including ligation, hybridization, or other approaches.

The term "amplification construct," as used herein generally refers to oligonucleotide. In various embodiments, the oligonucleotide can be linked to a reactant or a reaction product by a linker. In various embodiments, the oligonucleotide can comprise an adapter. In various embodiments, the adapter can comprise a primer. In various embodiments, the primer can be extended by a polymerase. In various embodiments, the polymerase comprises a reverse transcriptase. In alternative embodiments, the polymerase comprises a DNA polymerase. In various embodiments, extension of the primer can produce a reverse complement of the reactant barcode sequence or a portion thereof.

The term "analyte," as used herein, generally refers to a species of interest for detection. An analyte can be a biological analyte, such as a nucleic acid molecule or protein. An analyte can be an atom or molecule. An analyte can be a subunit of a larger unit, such as, e.g., a given sequence of a polynucleotide sequence or a sequence as part of a larger sequence. An analyte of the present disclosure includes a secreted analyte, a soluble analyte, and/or an extracellular analyte. In various embodiments, an analyte can comprise a reactant. In various embodiments, an analyte can comprise a reaction product.

As used herein, the term "barcode," generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode can be unique. Barcodes can have a variety of different formats. For example, barcodes can include: polynucleotide barcodes or barcode sequences; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence can be a targeted sequence or a non-targeted sequence. The nucleic acid barcode molecule can be coupled to or attached to the nucleic acid molecule comprising the nucleic acid sequence. For example, in the methods and compositions described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). The processing of the nucleic acid molecule comprising the nucleic acid sequence, the nucleic acid barcode molecule, or both, can include a nucleic acid reaction, such as, in non-limiting examples, reverse transcription, nucleic acid extension, ligation, etc. The nucleic acid reaction can be performed prior to, during, or following barcoding of the nucleic acid sequence to generate the barcoded nucleic acid molecule. For example, the nucleic acid molecule comprising the nucleic acid sequence can be subjected to reverse transcription and then be attached to the nucleic acid barcode molecule to generate the barcoded nucleic acid molecule, or the nucleic acid molecule comprising the nucleic acid sequence can be attached to the nucleic acid barcode molecule and subjected to a nucleic acid reaction (e.g., extension, ligation) to generate the barcoded nucleic acid molecule. A barcoded nucleic acid molecule can serve as a template, such as a template polynucleotide, that can be further processed (e.g., amplified) and sequenced to obtain the target nucleic acid sequence. For example, in the methods and systems described herein, a barcoded nucleic acid molecule can be further processed (e.g., amplified) and sequenced to obtain the nucleic acid sequence of the nucleic acid molecule (e.g., mRNA).

The term "bead," as used herein, generally refers to a particle. The bead can be a solid or semi-solid particle. The bead can be a gel bead. The gel bead can include a polymer matrix (e.g., matrix formed by polymerization or cross-linking). The polymer matrix can include one or more polymers (e.g., polymers having different functional groups or repeat units). Polymers in the polymer matrix can be randomly arranged, such as in random copolymers, and/or have ordered structures, such as in block copolymers. Cross-linking can be via covalent, ionic, or inductive, interactions, or physical entanglement. The bead can be a macromolecule. The bead can be formed of nucleic acid molecules bound or hybridized together. The bead can be formed via covalent or non-covalent assembly of molecules (e.g., macromolecules), such as monomers or polymers. Such polymers or monomers can be natural or synthetic. Such polymers or monomers can be or include, for example, nucleic acid molecules (e.g., DNA or RNA). The bead can be formed of a polymeric material. The bead can be magnetic or non-magnetic. The bead can be rigid. The bead can be flexible and/or compressible. The bead can be disruptable or dissolvable. The bead can be a solid particle (e.g., a metal-based particle including but not limited to iron oxide, gold or silver) covered with a coating comprising one or more polymers. Such coating can be disruptable or dissolvable.

The term "bead specific barcode" as used herein, generally refers to a barcode that identifies a bead. In various embodiments, a bead specific barcode can comprise a unique molecular identifier (UMI).

The term "biological particle," as used herein, generally refers to a discrete biological system derived from a biological sample. The biological particle can be a macromolecule. The biological particle can be a small molecule. The biological particle can be a virus. The biological particle can be a cell or derivative of a cell. The biological particle can be an organelle. The biological particle can be a cell nucleus. The biological particle can be a rare cell from a population of cells. The biological particle can be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle can be a constituent of a cell. The biological particle can be or can include DNA, RNA, organelles, proteins, or any combination thereof. The biological particle can be or can include a matrix (e.g., a gel or polymer matrix) comprising a cell or one or more constituents from a cell (e.g., cell bead), such as DNA, RNA, organelles, proteins, or any combination thereof, from the cell. The biological particle can be obtained from a tissue of a subject. The biological particle can be a hardened cell. Such hardened cell may or may not include a cell wall or cell membrane. The biological particle can include one or more constituents of a cell, but may not include other constituents of the cell. An example of such constituents is a nucleus or an organelle. A cell may be a live cell. The live cell can be capable of being cultured, for example, being cultured when enclosed in a gel or polymer matrix, or cultured when comprising a gel or polymer matrix.

As used herein, the term "blocking construct" generally refers to an oligonucleotide that is unable to act as a primer for a polymerase. In various embodiments, the blocking construct can prevent reverse transcription of a portion of an oligonucleotide of an RBO construct. In various embodiments, a 3' end can be non-reactive and can comprise a 3' end blocker.

The term "cell bead," as used herein, generally refers to a hydrogel, polymeric, or crosslinked material that comprises (e.g., encapsulates, contains, etc.) a biological particle (e.g., a cell, a nucleus, a fixed cell, a cross-linked cell), a virus, components of or macromolecular constituents of or derived from a cell or virus. For example, a cell bead can comprise a virus and/or a cell. In various cases, a cell bead comprises a single cell. In various cases, a cell bead can comprise multiple cells adhered together. A cell bead can include any type of cell, including without limitation prokaryotic cells, eukaryotic cells, bacterial, fungal, plant, mammalian, or other animal cell types, mycoplasmas, normal tissue cells, tumor cells, immune cells, e.g., a T-cell (e.g., CD4 T-cell, CD4 T-cell that comprises a dormant copy of human immunodeficiency virus (HIV)), a B cell, or a dendritic cell, a fixed cell, a cross-linked cell, a rare cell from a population of cells, or any other cell type, whether derived from single cell or multicellular organisms. Furthermore, a cell bead can comprise a live cell, such as, for example, a cell can be capable of being cultured. Moreover, in various examples, a cell bead can comprise a derivative of a cell, such as one or more components of the cell (e.g., an organelle, a cell protein, a cellular nucleic acid, genomic nucleic acid, messenger ribonucleic acid, a ribosome, a cellular enzyme, etc.). In various examples, a cell bead can comprise material obtained from a biological tissue, such as, for example, obtained from a subject. In various cases, cells, viruses or macromolecular constituents thereof are encapsulated within a cell bead. Encapsulation can be within a polymer or gel matrix that forms a structural component of the cell bead. In various cases, a cell bead is generated by fixing a cell in a fixation medium or by cross-linking elements of the cell, such as the cell membrane, the cell cytoskeleton, etc.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

The terms "coupled," "linked," "conjugated," "associated," "attached," "connected" or "fused," as used herein, may be used interchangeably herein and generally refer to one molecule (e.g., polypeptide, receptor, analyte, etc.) being attached, bound, or connected (e.g., chemically bound) to another molecule (e.g., polypeptide, receptor, analyte, etc.). In various embodiments described herein, linked comprises covalently linked or non-covalently linked.

In various embodiments, oligonucleotides can be linked to a reactant. In various embodiments, one or more oligonucleotides can be linked to a reaction product. In various embodiments, first oligonucleotide can be linked to a reaction product by a first linker and a second oligonucleotide can be linked to a reaction product by a second.

The term "covalent" as used herein can mean a chemical bond involving the sharing of at least one electron pair. Accordingly, two molecules are "covalently linked" or "covalently attached" to one another when at least one atom in the first molecule shares at least one electron pair with at least one atom in the second molecule. In some circumstances, a covalent linkage between two molecules can involve one or more intermediary molecules, for example, where a first molecule and a second molecule are each covalently linked to a linker molecule. In such a circumstance, the first and second molecules may be considered covalently linked via the linker molecule.

As used herein, the term "deoxyribonucleic acid" or "DNA" means a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

As used herein, the term "enzymatic activity" means a rate of reaction catalyzed by an enzyme in accordance with various embodiments. In various embodiments, enzymatic activity can be expressed quantitatively. A non-limiting example of a quantitative unit for enzymatic activity can comprise micromoles of reaction product or substrate formed per minute.

As used herein, the term "inert polymer" means a polymer that is non-reactive to enzymatic activity. Inert polymers may be resistant to oxidation or reduction. Non-limiting examples of inert polymers include polyethylene glycol (PEG), Poly(N-vinylpyrrolidone) (PVP), Polyglycerol (PG), Poly(N-(2-hydroxypropyl) methacrylamide) (PHPMA), or Polyoxazolines (POZs).

The term "insert oligonucleotide," as used herein, generally means a nucleotide molecule including a targeting or tagging sequence with two flanking sequences on either side of the tagging sequence. In various aspects, insert oligonucleotides are configured to be inserted into a targeting genomic locus or a tagging genomic locus using a complementary sequence of the targeting or tagging sequences to the targeting or tagging genomic loci. In various embodiments, an insert oligonucleotide can comprise a tagging barcode.

As used herein, the term "linker" may be used interchangeably with the term "spacer" or "linker molecule" and means an inert polymer that can hold two or more molecules together. In various embodiments, linkers may act to distance two molecules away from one another. In various embodiments, a linker length may be selected for a specified application. In various embodiments, linkers may comprise polyethylene glycol (PEG), Poly(N-vinylpyrrolidone) (PVP), Polyglycerol (PG), Poly(N-(2-hydroxypropyl) methacrylamide) (PHPMA), Polyoxazolines (POZs), or any other known or useful non-reactive molecule able to connect two or one other molecules together. As used herein, linkers may be used to connect oligonucleotides to reactants or reaction products.

As used herein, the term "locked nucleic acid (LNA)" also known as "bridged nucleic acid (BNA) and often referred to as inaccessible RNA means an inaccessible nucleotide such as RNA. In various embodiments, LNAs comprise a modified RNA nucleotide in which the ribose moiety is modified with an extra bridge connecting the 2' oxygen and 4' carbon.

The term "macromolecular constituent," as used herein, generally refers to a macromolecule contained within or from a biological particle. The macromolecular constituent may comprise a nucleic acid. In various cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

As used herein, the term "ones" means more than one.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In various cases, a partition may be a virtual compartment that can be defined and identified by an index (e.g., indexed libraries) across multiple and/or remote physical compartments. For example, a physical compartment may comprise a plurality of virtual compartments.

As used herein, the term "plurality" can be 2, 3, 4, 5, 6, 7, 8, 9, 10, or more.

A "polynucleotide", "nucleic acid", or "oligonucleotide" refers to a linear polymer of nucleotides (including deoxyribonucleotides, ribonucleotides, or analogs thereof) joined by internucleotidic linkages. Typically, a polynucleotide comprises at least three nucleotides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

A "reactant" and "substrate" are used synonymously and, as used herein generally refer to a molecule that can bind to an active site of an enzyme. In various embodiments, one or more reactants can bind to the active site of the enzyme. The enzyme can then convert the reactant(s) into one or more reaction products. In some embodiments, the rate at which reactants are converted into reaction products by an enzyme can be referred to an enzymatic activity. In various embodiment, systems and methods are disclosed for measuring the enzymatic activity (e.g., rate of reactant to reaction product conversion).

As used herein, the term "reactant barcoded oligonucleotide" (RBO) construct means an oligonucleotide comprising first and second adapter binding sites on adjacent and opposing sides of a barcode sequence. In various embodiments, RBO constructs may comprise linkers. In various embodiments linkers can have a first portion attached to a 3' end of an adapter binding site of the oligonucleotide and a second portion attached a reactant, thereby connecting the oligonucleotide to the reactant. In various embodiments, the reactant may have been modified into a reaction product by an enzyme and the reaction product may be linked to the RBO construct.

As used herein, the term "reactant barcode sequence," generally refers to a barcode that identifies a reactant or reaction product. In various embodiments, a reactant barcode sequence can comprise a nucleotide sequence. In various embodiments, the nucleotide sequence can be an oligonucleotide of an RBO construct.

A "reaction product," as used herein generally refers to a product produced by an enzyme. In various embodiments, the enzyme can bind a reactant at an active site and perform an enzymatic reaction to convert the reactant into a reaction product. In various embodiments, two or more reactants can bind to the active site of the enzyme and be converted into one or more reaction products. In various embodiments, reactants can be chemically modified by the enzyme.

The phrase "restricting movement," as used herein generally refers to inhibiting movement of two or more molecules relative to one another. More specifically, restricting movement comprises inhibiting movement and/or maintaining proximity of two oligonucleotides relative to one another at all times and particularly during reverse transcription reaction or a PCR amplification reaction. In some embodiments, restricting movement comprises inhibiting movement and/or maintaining proximity of two oligonucleotides relative to one another during a denaturation step and/or at temperatures that can denature double stranded DNA. In various embodiments described herein, restricting movement can increase the likelihood that two specific oligonucleotides remain hybridized, anneal readily, and/or have a high or increased affinity for one another.

In various embodiments, restricting movement of an RBO construct and an amplification construct can enable an adapter (e.g., a primer) of an oligonucleotide of the amplification construct to bind to an adapter binding site of an oligonucleotide of the RBO construct. In various embodiments, a polymerase can be recruited to extend the primer. In various embodiments, the recruited polymerase can comprise a reverse transcriptase. In various embodiments, the recruited polymerase can comprise a DNA polymerase.

One or both of the oligonucleotides described above, whose movement is restricted with respect to one another, may comprise one or more locked nucleic acids (LNAs). In various embodiments, LNAs may create a more rigid nucleotide structure and, therefore, increase an affinity of the oligonucleotides to one another. Further, the presence of one or more LNAs in at least one strand of a nucleotide sequence may serve to reduce breathing between the two complementary or partially complementary DNA sequences.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In various examples, such systems provide sequencing reads (also "reads" herein). A read may include a string of nucleic acid bases corresponding to a sequence of a nucleic acid molecule that has been sequenced. In various situations, systems and methods provided herein may be used with proteomic information.

As used herein, the term "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses). The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those available and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those available and commonly used in the art.

II. Overview

Figure 1A:
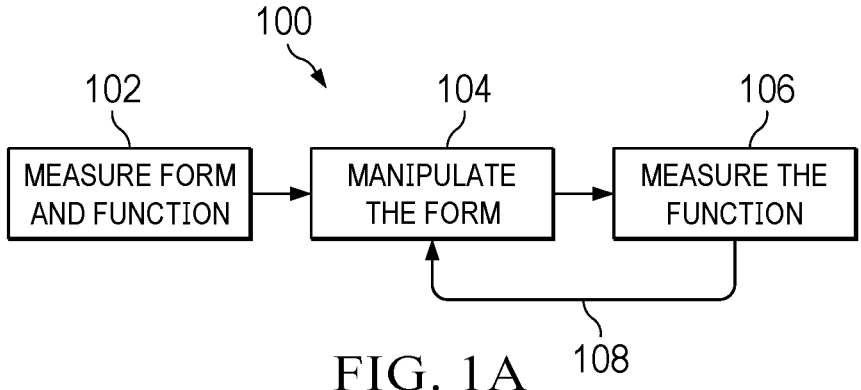
FIG. 1A illustrates an iterative process for enzyme optimization according to various embodiments.

A variety of technologies described herein (e.g., CRISPR/ Cas facilitated gene editing) and elsewhere may be used to generate many enzyme variants having different enzymatic activity levels. Detecting and assessing (e.g., quantifying) enzymatic activity level of the enzyme variants may allow researchers and medical practitioners to screen and select enzyme variants suitable for specific uses or applications based on their known, modified enzymatic activity level. Unfortunately, currently existing enzymatic activity assays are limited to bulk assays inhibited by low-throughput and require large quantities of raw input material, making them costly and inefficient. The technologies described herein solve this problem and many others. For example, the technologies and workflows described herein facilitate screening of large numbers of enzymatic variants by detecting the specific variant and assessing activity level of the enzyme variants at a single cell level, which has never before been successfully accomplished. The technologies described herein also provide techniques for assessing enzymatic reactions (e.g., the quantity of reaction product produced, or reactant consumed) either in bulk or at a single cell level. One non-limiting example of a biological endpoint assay provided herein comprises systems and methods for comparing treatment conditions versus control conditions. Additionally, the methods described herein comprise an iterative process enabling researchers to further optimize the previously modified enzyme variants and further refine enzymatic activity and function. The embodiments described herein can be impactful when applied in the fields of renewable energy, green chemistry, enzyme replacement therapy, and a variety of other fields. Enzymatic optimization systems and methods:

FIG. 1A illustrates an iterative process for optimizing enzymatic activity 100 according to various embodiments.

In various embodiments of the process, an initial step of measuring form and function 102 can be used to assess or characterize an original enzyme. For example, an amino acid sequence can be determined in accordance with various embodiments. Additionally, an enzymatic activity rate for the original enzyme in accordance with various embodiments. In various embodiments of the process 100, an enzymatic activity may be quantitatively assessed using the technologies disclosed herein.

In various embodiments, measuring an enzymatic activity may comprise measuring, in units, a rate of reaction catalyzed by an enzyme. In various embodiments, the units may comprise micromoles of a reactant transformed per minute. In various embodiments, aspects of an enzymatic activity assay may need to be kept constant, such as pH, temperature, enzyme concentration, reactant concentration, etcetera to compare different variants of an enzyme. Additionally, some enzymes operate optimally under different environmental conditions, so the assays disclosed herein may be customized to suit specific enzymes.

In various embodiments, after a base or original enzyme has been evaluated for enzymatic activity (e.g., Step 102), the enzyme form may be manipulated using CRISPR editing technologies to edit the gene encoding the enzyme, thereby modifying an enzymatic activity (e.g., by modifying the amino acid sequence of the enzyme). In various embodiments, many variants may be generated and then screened for enzymatic activity and identified.

In various embodiments of the process, a step for measuring the function 106 of the manipulated enzyme can be used to quantify an enzymatic activity. In various embodiments, the enzymatic activity of the original variant can be compared to the enzymatic activity of the manipulated enzyme.

In various embodiments, step 104 can be carried out any number of times and the function of each enzyme variant can be measured using step 106 in an iterative process 108. In various embodiments, enzyme variants producing more desirable quantitative measurements (e.g., enzymatic activity) can undergo further manipulation of form. The process can be performed iteratively until one or more enzyme variant reach an optimized enzymatic function (e.g., enzymatic activity).

In various embodiments, the iterative process 108 may be performed 1, 2, 3, 4, 5, 6, 7, 8, 9, 10, 20, 50, 100, 1000 or any number of times to optimize an enzymatic activity of an enzyme for a specific application or purpose. Purposes can include research, industrial, or therapeutic activities. For example, an enzyme's activity may be increased to produce a commercial product at an increased rate for a lower cost.

Figure 1B:
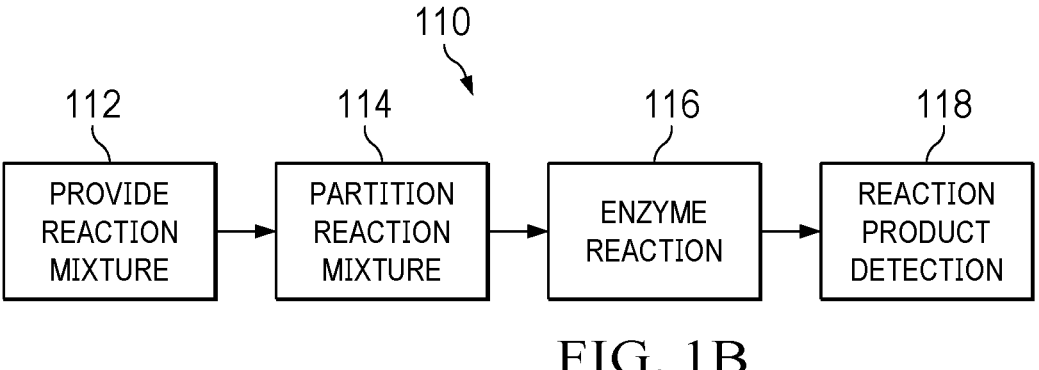
FIG. 1B illustrates steps in a method for assessing enzymatic activity according to various embodiments.

FIG. 1B illustrates steps in a method for assessing enzymatic activity 110 according to various embodiments. In various embodiments, step 106 may include one or more of the steps described in FIG. 1B.

Step 112 includes providing a reaction mixture using a plurality of the compositions described herein. For example, reactions mixtures may include an enzyme, a reactant barcoded oligonucleotide (RBO) construct, an amplification construct, and a blocking construct. Typically, buffers and other reagents may be included in the reaction mixture ensuring the enzyme remains functional.

Step 114 can include generating a partition and/or partitioning a reaction mixture into a partition (e.g., a well or vessel). In some cases, a reaction mixture may be created in the same step as partition generation. Partitions may serve to compartmentalize the reaction mixture. Compartmentalization may allow for identification of an origin of one or more of the components/reagents in the reaction mixture. For example, the enzyme may originate from a single cell.

Step 116 includes using the enzyme to generate one or more reaction products. The compositions (e.g., the reactant barcoded oligonucleotide (RBO) construct, the amplification construct, and the blocking construct) described herein may interact in a manner allowing for quantification of an enzymatic activity.

Step 118 includes detecting one or more reaction products generated from the enzyme converting reactants into reaction products. Detection of reaction products may include using one or more of the compositions described herein with one or more of the method steps described herein. Detection can include quantification of the reaction product. Detection can include identification of a cell of original. Detection can include identification of a partition of origin.

Figure 2:
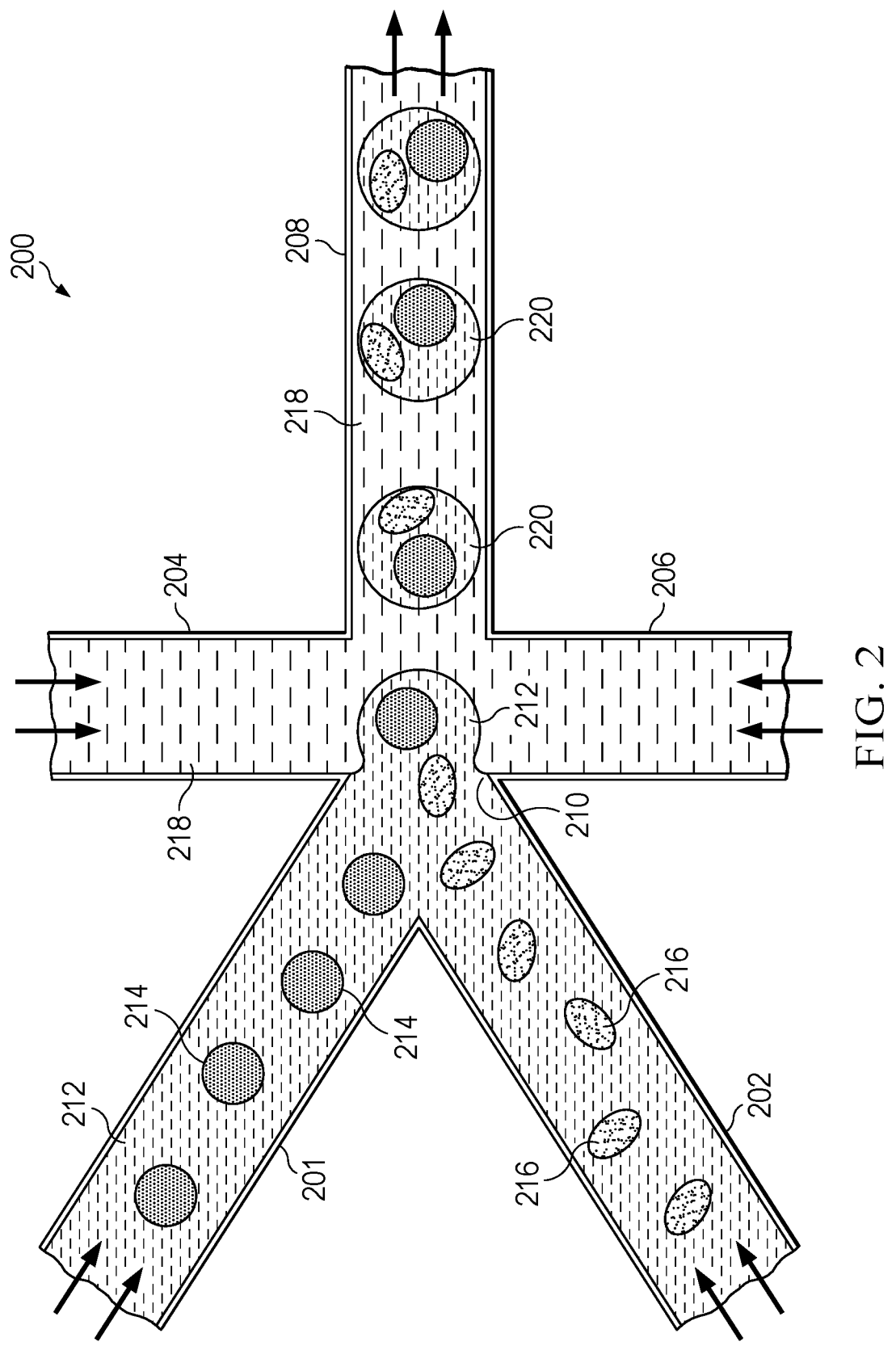
FIG. 2 is a schematic illustration showing an example of a microfluidic channel structure for delivering barcode carrying beads to droplets according to various embodiments.

The systems, compositions, and methods described herein allow for enzyme optimization by collecting data using the process described in FIG. 2 and iteratively changing a form of the enzyme as described in FIG. 1.

I. Exemplary Reaction Mixtures and Compositions

II.A. Exemplary Reaction Mixtures

FIG. 13 illustrates a reaction mixture 1300 in accordance with various embodiments. In various embodiments, a partition 1302 can comprise a reaction mixture 1300. In various embodiments, the partition 1302 can comprise a bead 1130 including one or more bead oligonucleotides 1370 extending therefrom. In various embodiments, the reaction mixture 1300 can further comprise one or more RBO constructs 1350, one or more amplification constructs 1360, one or more blocking constructs 1310, and an enzyme 1312. In some embodiments, the enzyme 1312 may enter the reaction mixture 1300 from a lysed cell 1314. In various embodiments, a cell may be added to the reaction mixture 1300 and subsequently lysed. In various embodiments, the reaction mixture 1300 can comprise an amplification enzyme 1380.

In various embodiments, the reaction mixture 1300 can comprise reagents necessary for cellular function. Non-limiting examples of cellular function can comprise enzymatic activity, protein synthesis, nucleic acid synthesis, respiration, metabolism, and ion transport processes. The reagents can comprise amino acids, nucleotides, salts, serum, and other nutrients in accordance with various embodiments. In various embodiments, the reaction mixture 1300 can comprise adapters (e.g., oligonucleotides comprising primers and barcode sequences). In various embodiments, the reaction mixture can comprise oligonucleotide amplification components (e.g., polymerase, nucleotides, adapters, and primers). In some embodiments, the reaction mixture 1300 can comprise CRISPR components (e.g., gRNA, CRISPR-associated endonuclease).

In various embodiments, the partition 1302 can comprise a physical barrier. In various embodiments, the physical compartment can include a droplet as described herein. In some embodiments, the physical compartment can include a well (e.g., a well in a 96-well plate).

In various embodiments, a bead oligonucleotide 1370 can be coupled to a bead 1130. The bead oligonucleotide 1370 may include a linear chain of nucleotides. In some cases, the chain of nucleotides may be branched. In various embodiments, the chain of nucleotides can be single stranded. In other embodiments, the chain of nucleotides may include one or more double stranded sequences. In various embodiments, the bead oligonucleotide 1370 can comprise a capture sequence 1372 and a nucleic acid barcode molecule 1374. In some embodiments, the bead oligonucleotide 1370 can, optionally, comprise a UMI. The bead 1130 can be used in the single cell workflows described herein, e.g., see Section V. SYSTEMS AND METHODS FOR SAMPLE COMPARTMENTALIZATION.

In various embodiments, the capture sequence 1372 of the bead oligonucleotide 1370 can hybridize to other single stranded oligonucleotides (e.g., a portion of the first oligonucleotide 1352 of the RBO construct 1350). In many cases, the capture sequence 1372 can be complementary to at least a portion of the first oligonucleotide 1352 of an RBO construct 1350. In many cases, the capture sequence 1372 can be complementary to at least a portion of a first adapter binding site of the RBO construct 1350.

In various embodiments, the nucleic acid barcode molecule 1374 can comprise a bead specific barcode. The bead specific barcode can serve to identify a bead origin. In various embodiments, the nucleic acid barcode molecule 1374 can comprise a partition-specific barcode sequence. The partition-specific barcode sequence can serve to identify a partition origin.

In various embodiments, the RBO construct 1350 can be coupled to the bead 1130. In many applications, the RBO construct 1350 can hybridize to the bead oligonucleotide 1370, or a portion thereof. In various embodiments, the RBO construct 1350 comprises a first reactant 1354.

In various embodiments, the blocking construct 1310 can be configured to prevent or inhibit the amplification enzyme 1380 from carrying out a reverse transcription reaction from generating a reverse complement of the first oligonucleotide 1352 of the RBO construct 1350. In various embodiments, the blocking construct 1310 can comprise a third oligonucleotide 1311. In various embodiments, at least a portion of the third oligonucleotide 1311 is complementary to at least a portion of the first oligonucleotide 1352 of the RBO construct 1350. Accordingly, the result of the assay will show less enzymatic activity as described herein (e.g., see Section III. EXEMPLARY METHODS).

In various embodiments, the amplification construct 1360 can comprise a second oligonucleotide 1362 and a second reactant 1364.

In various embodiments, the second oligonucleotide 1362 can be complementary to at least a portion of the first oligonucleotide 1352. In some embodiments, a portion of the second oligonucleotide 1362 can hybridize with a portion of the first oligonucleotide 1352.

In various embodiments, the second reactant 1364 of the amplification construct 1360 can be configured to react with the first reactant 1354 of the RBO construct 1350. In various embodiments, the enzyme 1312 can be configured to enzymatically react the first reactant 1354 with the second reactant 1364 to produce a reaction product.

In various embodiments, the reaction mixture 1300 can comprise the blocking construct 1310 in molar excess to the amplification construct 1360. In various embodiments, molar excess comprises 10-fold more of the blocking construct 1310 to the amplification construct 1360. In other embodiments, 100-fold more. In still other embodiments, 1000-fold more.

In various embodiments, the enzyme 1312 comprises an active site 1313. In various embodiments, the active site 1313 can interact with the reactants 1354, 1364. In various embodiments, the interaction can comprise the active site 1313 temporarily binding with the first reactant 1354 and temporarily binding with the second reactant 1364 to affect a chemical reaction between the first reactant 1354 and the second reactant 1364 to produce the reaction product. In various embodiments, binding can form between amino acid residues of the active site 1313 and amino acid residues of each of the reactants 1354, 1364.

In various embodiments, the reaction mixture 1300 can further comprise a splint oligonucleotide that can hybridize to the bead oligonucleotide 1370 and at least a portion of the first oligonucleotide 1352 of the RBO construct 1350. In various embodiments, the reaction mixture 1300 can further comprise a splint oligonucleotide that can hybridize to the bead oligonucleotide 1370 and at least a portion of a reverse complement of the first oligonucleotide 1352 of the RBO construct 1350.

In various embodiments, a plurality of reaction mixtures can each comprise an RBO construct, an amplification construct, and a blocking construct. In various embodiments each of the plurality of reaction mixtures can comprise a unique variant of an enzyme for comparison. In various embodiments, each of the plurality of reaction mixtures can comprise unique reactants for enzymatically producing a unique reaction product.

II.B. Exemplary RBO Constructs

FIG. 12A schematically illustrates an exemplary RBO construct 1200 for a reaction mixture for assessing enzymatic activity according to various embodiments. In various embodiments, the RBO construct 1200 can comprise a first oligonucleotide 1202 coupled to a first reactant 1212 by a first linker 1210. In various embodiments, the first oligonucleotide 1202 can comprise a reaction barcode sequence 1206, and can optionally include adapter binding sites (e.g., a first adapter binding site 1204 and a second adapter binding site 1208) on adjacent and opposing sides of the reaction barcode sequence 1206.

In various embodiments, an RBO construct 1200 can comprise a first oligonucleotide 1202 comprising a reaction barcode sequence 1206 having a first adapter binding site 1204 and a second adapter binding site 1208 adjacent to and on opposing sides and a first linker 1210 linked or covalently linked to a first reactant 1212. In various embodiments the first linker 1210 can be attached to the 3' end of the first oligonucleotide 1202.

In accordance with various embodiments, adapter binding sites 1204, 1208 as described herein can include, e.g., primer binding sites, sequences substantially identical or complementary to a capture sequence, sequences complementary to a portion of a splint oligonucleotide, or any combination thereof. In various embodiments, a first adapter binding site 1204 can be substantially identical or complementary to a capture sequence of a bead oligonucleotide (e.g., comprises a reverse complement sequence to the capture sequence) 1299. In various embodiments, the capture sequence can be complementary to the various bead oligonucleotides 1299 as described herein. In various embodiments, the bead oligonucleotide 1299 can be a gel bead oligonucleotide as described herein. In various embodiments, a first adapter binding site 1204 can comprise a sequence complementary to at least a portion of a splint oligonucleotide 1297, 1297a, 1297b (see FIGS. 12I, 12J, 12K, 12L) as described herein. An adapter can comprise a functional sequence, e.g., a functional sequence described herein.

In various embodiments, the first oligonucleotide 1202 can comprise 1, 2, 3, 4, 5, 6, 7, 8, 9, 10, 11, 12, 13, 14, 15, 16, 17, 18, 19, 20, or any number of LNAs. In various embodiments, the entire first oligonucleotide 1202 can be comprised of LNAs. In various embodiments 5%, 10%, 15%, 20%, 25%, 30% 35%, 40%, 45%, 50%, 55%, 60%, 65%, 70%, 75%, 80%, 85%, 90%, 95%, or 100% of the nucleotides within the first oligonucleotide 1202 can include LNAs or include a range between any of these percentages. In various embodiments, the first oligonucleotide 1202 comprises no LNAs.

II.C. Exemplary Amplification Constructs

FIG. 12B schematically illustrates an exemplary amplification construct 1214 for a reaction mixture for assessing enzymatic activity according to various embodiments. In various embodiments, the amplification construct 1214 can comprise a second oligonucleotide 1216 coupled to a second reactant 1220 by a second linker 1218.

In various embodiments, the second oligonucleotide 1216 can comprise a second adapter sequence.

In various embodiments, the second oligonucleotide 1216 can comprise 1, 2, 3, 4, 5, 6, 7, 8, 9, 10, 11, 12, 13, 14, 15, 16, 17, 18, 19, 20, or any number of LNAs. In various embodiments, the entire second oligonucleotide 1216 can be comprised of LNAs. In various embodiments 5%, 10%, 15%, 20%, 25%, 30% 35%, 40%, 45%, 50%, 55%, 60%, 65%, 70%, 75%, 80%, 85%, 90%, 95%, or 100% of the nucleotides within the second oligonucleotide 1216 can include LNAs or include a range between any of these percentages. In various embodiments, the second oligonucleotide 1216 comprises no LNAs.

II.D. Exemplary Blocking Constructs

FIG. 12C schematically illustrates an exemplary blocking construct 1221 for a reaction mixture for assessing enzymatic activity according to various embodiments. In various embodiments, the blocking construct 1221 can comprise a third oligonucleotide 1222.

In various embodiments, the third oligonucleotide 1222 can comprise 1, 2, 3, 4, 5, 6, 7, 8, 9, 10, 11, 12, 13, 14, 15, 16, 17, 18, 19, 20, or any number of LNAs. In various embodiments, the entire third oligonucleotide 1222 can be comprised of LNAs. In various embodiments 5%, 10%, 15%, 20%, 25%, 30% 35%, 40%, 45%, 50%, 55%, 60%, 65%, 70%, 75%, 80%, 85%, 90%, 95%, or 100% of the nucleotides within the third oligonucleotide 1222 can include LNAs or include a range between any of these percentages. In various embodiments, the third oligonucleotide 1222 comprises no LNAs.

In various embodiments, a portion of a first oligonucleotide can be complementary to the third oligonucleotide 1222. In various embodiments, when the first oligonucleotide 1202 is hybridized to the third oligonucleotide 1222, an amplification reaction can be prevented from occurring (e.g., an amplification reaction using an amplification enzyme [e.g., reverse transcriptase] to extend second adapter [e.g., a second primer]) of the first oligonucleotides. In various embodiments, the third oligonucleotide 1222 of the blocking construct 1221 competes with a second oligonucleotide of the amplification construct for hybridization with the first oligonucleotide of an RBO construct. In exemplary reaction mixtures a quantity of the blocking construct 1221 can be greater than a quantity of the amplification construct. In exemplary reaction mixtures a quantity of an blocking construct 1221 can be 10-fold more than a quantity of an amplification construct. In exemplary reaction mixtures a quantity of the blocking construct 1221 can be 100-fold more than a quantity of an amplification construct. In exemplary reaction mixtures a quantity of the blocking construct 1221 can in molar excess relative to a quantity of the amplification construct.

In various embodiments, the third oligonucleotide 1221 comprises a non-reactive 3' end or 3' end blocker, thereby preventing amplification or polymerization of a reverse complement of the first oligonucleotide of RBO construct when hybridized thereto. In various embodiments, amplification of the first oligonucleotide can be prevented by a hybridized third oligonucleotide 1222 of a blocking construct 1221 comprising a non-reactive 3' end. In various embodiments, the 3' end can comprise a phosphorylated 3' end. In various embodiments, the 3' end can comprise a carbon spacer (e.g., a spacer C3, a spacer C6, a spacer C9, a spacer C12, and a spacer C18. In various embodiments, the 3' end can be biotinylated. In various embodiments, the 3' end can comprise an inverted base (e.g., an inverted dideoxy-T). Systems and methods for 3' end modification are described in International Application No. WO2020185791, which is entirely incorporated herein by reference for all purposes.

II.E. Exemplary Extension Reactions and Products

FIG. 12D schematically illustrates a blocking construct 1221 hybridized to a second adapter binding site 1208 of a first oligonucleotide 1202 of an RBO construct 1200 for assessing enzymatic activity according to various embodiments.

In various embodiments, a first reactant 1212 can be coupled to the RBO construct 1200 by a linker 1210. In various embodiments, the first reactant 1212 has not undergone an enzymatic reaction.

In various embodiments, the blocking construct 1221 cannot be extended in a polymerization reaction. As such, an amplification enzyme 1226 cannot produce a reverse complement of a reaction barcode sequence 1206 of the RBO construct in accordance with various embodiments. In this example, a first adapter binding site 1204 also can remain unused in accordance with various embodiments.

FIG. 12E schematically illustrates portion of a second oligonucleotide 1216 of an amplification construct 1214 hybridized to a portion of an RBO construct 1200 for assessing enzymatic activity according to various embodiments. In various embodiments, hybridization between a portion of a first oligonucleotide 1202 of the RBO construct 1200 and a portion of the second oligonucleotides 1216 can be facilitated by the RBO construct 1200 and the amplification construct 1214 being held in close proximity due to a first reactant and a second reactant joining to form a reaction product 1228 using an enzyme. In some embodiments, the reaction product 1228 can be coupled to the first oligonucleotide 1202 through a linker 1210. In some embodiments, the reaction product 1228 can be coupled to the second oligonucleotide 1216 through a linker 1218.

In various embodiments, a amplification enzyme 1226 can extend the second oligonucleotide 1216 (e.g., a primer) to generate a reverse complement of the reaction barcode sequence 1206 and the first adapter binding site 1204.

In various embodiments, the first oligonucleotide 1202 can comprise a first adapter binding site 1204 adjacent to a 5' end of the reaction barcode sequence 1206. In various embodiments, the RBO construct 1200 can comprise a second adapter binding site 1208 adjacent to a 3' end of the reaction barcode sequence 1206. In various embodiments, a plurality of first adapters comprising a sequence that is complementary to at least a portion of the first adapter binding site 1204 can be added to the compositions. In various embodiments, a plurality of second adapters comprising a sequence that can be complementary to at least a portion of the second adapter binding site 1208 can be added to the compositions. In various embodiments, one or more of amplification enzymes 1226 can be used in an amplification reaction to generate a reverse complement of the barcode sequence by extending the second adapter of the second oligonucleotide 1216. In some embodiments, the one or more amplification enzymes comprises a polymerase. In some embodiments, the one or more amplification enzymes comprises a reverse transcriptase.

In various embodiments, the second oligonucleotide 1216 can comprise at least one locked nucleic acid (LNA) for increasing the affinity between the first oligonucleotide 1202 and the second oligonucleotide 1216 relative to when no LNAs are present. One or more LNAs can be present in any of the nucleotide sequences described herein and can increase a binding affinity to a reverse complement sequence relative to other adapters other sequences present that do not include an LNA. In various embodiments, the second oligonucleotide 1216 can comprise 1, 2, 3, 4, 5, 6, 7, 8, 9, 10, 11, 12, 13, 14, 15, 16, 17, 18, 19, 20, or any number of LNAs. In various embodiments, the entire second oligonucleotide is comprised of LNAs. In various embodiments 5%, 10%, 15%, 20%, 25%, 30% 35%, 40%, 45%, 50%, 55%, 60%, 65%, 70%, 75%, 80%, 85%, 90%, 95%, or 100% of the nucleotides within the second oligonucleotide 1216 can comprise LNAs or include a range between any of these percentages. In various embodiments, the second oligonucleotide 1216 comprises no LNAs.

Amplification reactions in accordance with embodiments of the invention can include, e.g., methods to extend adapters/primers, polymerase chain reaction (PCR), reverse transcription or any combination thereof. In various embodiments, an amplification reaction can comprise PCR. In various embodiments, an amplification reaction can comprise reverse transcription.

In various embodiments, the amplification enzyme 1226 can comprise any molecule having catalytic nucleotide extension properties, including, but not limited to, transcriptases and polymerases. In various embodiments, the amplification enzyme can comprise a reverse transcriptase. In various embodiments, the amplification enzyme can comprise a DNA polymerase. In various embodiments, the amplification enzyme can comprise an RNA polymerase.

In some embodiments, the amplification enzyme 1226 can be a reverse transcriptase. In some embodiments, the amplification enzyme 1226 (e.g., reverse transcriptase) can carry out an extension reaction to generate an extension product 1230 (see FIG. 12F).

Extension products in accordance with embodiments of the invention can include, e.g., nucleotide sequences, ssDNA molecules, dsDNA molecules, RNA molecules, or any combination thereof.

In various embodiments, the compositions can comprise a reaction product 1228 catalyzed by enzymatic action from an enzyme undergoing assessment. The reactants can be selected for based on an enzyme under investigation. Specifically, reactants can be anything that can be reacted with by the enzyme under investigation. In various embodiments, the enzyme under investigation can react the reactants forming the reaction product 1228 can them bring the RBO construct 1200 and the amplification construct 1214 into close proximity to outcompete the blocking construct in hybridizing with the second adapter binding site 1208 of the first oligonucleotide 1202. In various embodiments, reacting the reactants can increase the affinity of the second oligonucleotide 1216 of the amplification construct 1214 and the second adapter binding site 1208 of the first oligonucleotide 1202 of the RBO construct 1200. In various embodiments, the reactants and reaction product 1228 can comprise a protein, carbohydrate, double stranded nucleotide, or a synthetic compound.

FIG. 12F schematically illustrates a completed extension product 1230 hybridized to a first oligonucleotide 1202 of an RBO construct 1200 in accordance with various embodiments. In various embodiments, the extension product 1230 can comprise a second oligonucleotide 1216 of an amplification construct 1214, a reaction barcode sequence reverse complement 1206*rc*, and a first adapter binding site reverse complement 1204*rc*. Similarly to FIG. 12E, a reaction product 1228 can continue to hold the RBO construct 1200 in close proximity to the amplification construct 1214 even under conditions that can denature doubled stranded nucleotide sequences.

In various embodiments, the extension product 1230 can be generated using reverse transcription, thereby generating a reverse complement of the first oligonucleotide, which can comprise a reaction barcode sequence reverse complement 1206*rc* and a reverse complement of a first adapter binding site reverse complement 1204*rc*, and a second oligonucleotide 1216 (e.g., a second adapter) of the amplification construct 1214 according to various embodiments. In various embodiments, the first oligonucleotide 1202 can be coupled to a reaction product 1228 through a linker 1210. In various embodiments, the first oligonucleotide extension product 1230 can be coupled to a reaction product 1228 through a linker 1210. In some embodiments, one or both linkers 1210, 1218 may be cleaved in performing the methods described herein.

II.F. Exemplary Amplification Reactions and Products

FIG. 12G illustrates compositions that can be included in a reaction mixture for assessing enzymatic activity for amplifying the first oligonucleotide 1202 and the extension product 1230 shown in FIG. 12F. In various embodiments, the reaction mixture comprises a forward adapter 1231 (e.g., a forward primer) that can hybridize to a reverse complement of a first adapter binding site reverse complement 1204*rc* and a reverse adapter 1233 (e.g., a reverse primer) that can hybridize to a second adapter binding site 1208 according to various embodiments. In various embodiments, a reaction mixture can comprise a forward primer that can hybridize to a portion of the extension product 1230 and a reverse primer that can hybridize to a portion of the extension product 1230. In various embodiments, a reaction mixture can comprise a forward primer that can hybridize to the first oligonucleotide 1202 and reverse primer that can hybridize to the first oligonucleotide 1202. In various embodiments, the reaction mixture can comprise adapters (e.g. primers) for amplifying any particular region of interest in any combination. In various embodiments, the reaction mixture can comprise an amplification enzyme for carrying out an amplification reaction (e.g., a polymerase chain reaction). In various embodiments, the resulting amplification reaction can enable downstream assessment of enzymatic activity using the resulting, amplified first oligonucleotides 1202 and the extension products 1230. In various embodiments, the first oligonucleotide 1202 may be coupled to a reaction product 1228 through a linker 1210. In various embodiments, the extension product 1230 may be coupled to the reaction product 1228 through a linker 1218.

In some embodiments, an enzymatic activity acting on the reactants can be assessed using an amplification process (e.g., see FIG. 12G). In various embodiments, the amplification process can occur after a reverse transcription process.

In various embodiments, the first and second linkers 1210, 1218 can comprise an inert polymer. In various embodiments, the inert polymer can comprise polyethylene glycol (PEG). In various embodiments, the inert polymer can be a compound resistant to oxidation or reduction. Linkers can couple oligonucleotides to reactants in accordance with various embodiments. In some embodiments, a reaction product 1228 can include a linker for every reactant forming the reaction product 1228.

FIG. 12H illustrates a non-limiting example of compositions that can be included in a reaction mixture 1300 for assessing enzymatic activity comprising an extension product 1230 hybridized to a bead oligonucleotide 1299 according to various embodiments. In various embodiments, the bead 1130 described herein can be coupled to the bead oligonucleotide 1299.

Figure 11:
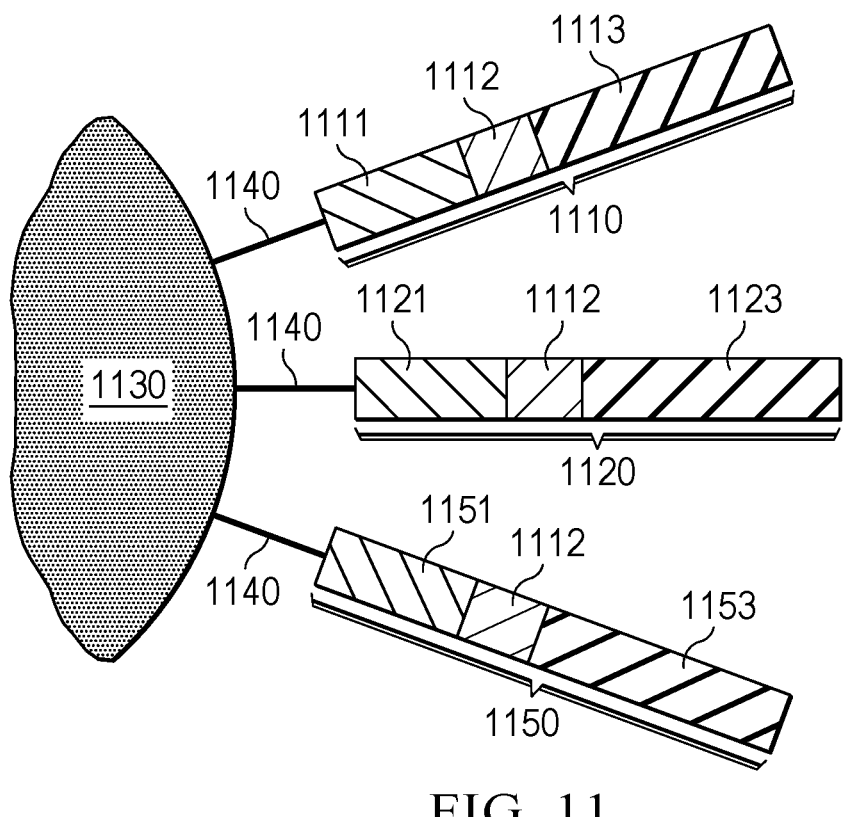
FIG. 11 schematically shows another example of a barcode-carrying bead according to various embodiments.

Now, additionally, referring to FIGS. 11, 12H, and 13, compositions in a reaction mixture 1300 for assessing enzymatic activity can comprise a bead 1130 coupled to a bead oligonucleotide 1299. In various embodiments, the bead oligonucleotide 1299 can be or comprise a nucleic acid barcode molecule (e.g., 1110, 1120, 1150) comprising a barcode sequence 1112 and a capture sequence (e.g., 1113, 1123, 1153). In some embodiments, barcode sequence 1112 can be a partition-specific barcode sequence. In some cases, additionally to the barcode sequence 1112, the nucleic acid barcode molecule comprises a UMI sequence. In some cases, alternatively to the barcode sequence 1112, the nucleic acid barcode molecule comprises a UMI sequence. In some cases, the nucleic acid barcode molecule (e.g., 1110, 1120, 1150) comprises an adapter sequence (e.g., 1111, 1121, 1151).

FIG. 12I illustrates a non-limiting example of compositions that can be included in a reaction mixture for assessing enzymatic activity. In various embodiments, extension product 1230 can be coupled to a bead oligonucleotide by ligation using a splint oligonucleotide 1297. For example, a first portion 1297*a* of splint oligonucleotide 1297 can be complementary to the sequence of the bead oligonucleotide. For example, a second portion 1297*b* of splint oligonucleotide can be complementary to a sequence of the extension product 1230 (e.g., can be complementary to a reverse complement of the first adapter binding site reverse complement reverse complement 1204*rc* or a portion thereof. In various embodiments, hybridization of bead oligonucleotide 1299 to the first portion 1297*a* of the splint oligonucleotide 1297 and hybridization of the extension product 1230 to the second portion 1297*b* of the splint oligonucleotide 1297 facilitates attachment (e.g., ligation) of the bead oligonucleotide 1299 to the extension product 1230. In various embodiments, the reaction mixture further comprises a ligase (not shown) for attaching the bead oligonucleotide 1299 to the extension product 1230 via ligation. Ligation can be used in any process joining nucleotide sequences (e.g., DNA ligase catalyzing a formation of two covalent phosphodiester bonds between a 3' hydroxyl group of one nucleotide and a 5' phosphate group of a second nucleotide.

FIG. 12J illustrates another non-limiting example of compositions that can be included in a reaction mixture 1300 for assessing enzymatic activity. In various embodiments, extension product 1230 can be coupled to a bead oligonucleotide 1130 by ligation using a splint oligonucleotide 1297. For example, a first portion 1297*a* of splint oligonucleotide 1297 can be complementary to a sequence of bead oligonucleotide 1299. For example, a second portion 1297*b* of splint oligonucleotide 1297 can be complementary to a sequence of the extension product 1230 (e.g., can be complementary to second oligonucleotide 1216 or a portion thereof). In various embodiments, hybridization of bead oligonucleotide 1299 to the first portion 1297*a* of the splint oligonucleotide 1297 and hybridization of the extension product 1230 to the second portion 1279*b* of the splint oligonucleotide 1297 facilitates attachment (e.g., ligation) of the bead oligonucleotide 1299 to the extension product 1230. In various embodiments, the reaction mixture 1300 further comprises a ligase (not shown) for attaching the bead oligonucleotide 1299 to the extension product 1230 via ligation.

FIG. 12K illustrates another non-limiting example of compositions that can be included in a reaction mixture 1300 for assessing enzymatic activity. In various embodiments, first oligonucleotide 1202 can be coupled to a bead oligonucleotide 1130 by ligation using a splint oligonucleotide 1297. For example, a first portion 1297*a* of splint oligonucleotide 1297 can be complementary to a sequence of bead oligonucleotide 1299. For example, a second portion 1297*b* of splint oligonucleotide 1297 can be complementary to a sequence of the first oligonucleotide 1202. In some embodiments, the second portion 1297*b* of splint oligonucleotide 1297 can be complementary to the first adapter binding site 1204 of the first oligonucleotide 1202. In various embodiments, hybridization of bead oligonucleotide 1299 to the first portion 1297*a* of the splint oligonucleotide 1297 and hybridization of the first oligonucleotide 1202 to the second portion 1279*b* of the splint oligonucleotide 1297 facilitates attachment (e.g., ligation) of the bead oligonucleotide 1299 to the first oligonucleotide 1202. In various embodiments, the reaction mixture 1300 further comprises a ligase (not shown) for attaching the bead oligonucleotide 1299 to the first oligonucleotide 1202 via ligation.

FIG. 12L illustrates another non-limiting example of compositions that can be included in a reaction mixture 1300 for assessing enzymatic activity. In various embodiments, first oligonucleotide 1202 can be coupled to a bead oligonucleotide 1130 by ligation using a splint oligonucleotide 1297. For example, a second portion 1297*b* of splint oligonucleotide 1297 can be complementary to a sequence of bead oligonucleotide 1299. For example, a first portion

1297*a* of splint oligonucleotide 1297 can be complementary to a sequence of the first oligonucleotide 1202. In some embodiments, the first portion 1297*a* of splint oligonucleotide 1297 can be complementary to the second adapter binding site 1208 of the first oligonucleotide 1202. In various embodiments, hybridization of bead oligonucleotide 1299 to the first portion 1297*a* of the splint oligonucleotide 1297 and hybridization of the first oligonucleotide 1202 to the second portion 1279*b* of the splint oligonucleotide 1297 facilitates attachment (e.g., ligation) of the bead oligonucleotide 1299 to the first oligonucleotide 1202. In various embodiments, the reaction mixture 1300 further comprises a ligase (not shown) for attaching the bead oligonucleotide 1299 to the first oligonucleotide 1202 via ligation.

In various embodiments, a capture sequence of the bead oligonucleotide can be complementary to at least a portion of the extension product 1230 generated by extension of second adapter (e.g., a second primer) of the second oligonucleotide 1216. For example, the capture sequence can be complementary to the reverse complement of the first adapter binding site reverse complement 1204*rc* of the first oligonucleotides 1202 generated by extension of second adapter (e.g., a second primer) of the second oligonucleotide 1216.

In some cases, the capture sequence can be configured to couple to an amplification product of the amplification reaction 1508 via ligation using a splint oligonucleotide (see exemplary process of FIG. 15). For example, the capture sequence can be complementary to a first portion of a splint oligonucleotide, and the amplification product of the amplification reaction 1508 can be complementary to a second portion of the splint oligonucleotide. Accordingly, the splint oligonucleotide can hybridize to both the capture sequence of the nucleic acid barcode molecule and the amplification product of amplification reaction 1508. Ligation of the nucleic acid barcode molecule and the amplification product of amplification reaction can be catalyzed by a ligase. The ligase can be a ligase suitable for single stranded (ss) nucleic acid ligation, e.g., suitable for ss DNA ligation. Suitable ligases include, e.g., CircLigase, T4 DNA ligase, T7 DNA ligase, SPLINTR®, T4RNA Ligase, KOD RNA Ligase, double-stranded DNA ligase, ATCV1 ligase, and the like.

Now referring back to FIG. 13, in various embodiments, multiple enzymes 1312 can be screened in the same assay. In various embodiments, multiple enzyme variants can be screened in the same assay. In various embodiments, reaction barcode sequences 1206 can assist in identifying which enzyme variant acts on which specific (i.e., unique) reactant.

In various embodiments, a composition in a reaction mixture for assessing enzymatic activity can comprise an RBO construct, an amplification construct, a blocking construct, and an enzyme as the composition for assessing enzymatic activity. In various embodiments, the composition in a reaction mixture for assessing enzymatic activity can comprise a plurality of reactants that can be paired by one of the unique enzymes to form a unique reaction product.

In various embodiments, compositions in a reaction mixture for assessing enzymatic activity can comprise a plurality of RBO constructs 1200. In various embodiments, the plurality of RBO constructs 1202 can each comprise a first oligonucleotide 1202 comprising a reaction barcode sequence 1206 and a first linker 1210 that connects the first oligonucleotide 1202 to a first reactant 1212.

In various embodiments, compositions in a reaction mixture for assessing enzymatic activity can further comprise a plurality of amplification constructs 1214. In various embodiments, each of the amplification construct 1214 can comprise a second oligonucleotide 1216 that can be complementary to at least a portion of the first oligonucleotide 1202 and a second linker 1218 that connects the second oligonucleotide 1216 to a second reactant 1220.

In various embodiments, each of the first oligonucleotides 1202 of each of the RBO constructs 1200 each include a first adapter binding site 1204 adjacent to a 5' end of the reaction barcode sequence 1206 and a second adapter binding site 1208 adjacent to a 3' end of the reaction barcode sequence 1206. In various embodiments, the reaction mixture can further comprise a plurality of first adapters (e.g. forward primers) comprising a sequence that is complementary to at least a portion of the first adapter binding site 1204. In various embodiments, the reaction mixture can further a plurality of second adapters (e.g. reverse primers) comprising a sequence that is complementary to at least a portion of the second adapter binding site 1208.

In various embodiments, a plurality of the reactants can be different from one another and two or more can combine in an enzymatic reaction by an enzyme of interest of produce a plurality of reaction products. In such embodiments, an enzymatic activity of more than one enzyme can be quantified in the same experiment or assay using different recants. In various embodiments, different reactants can allow for assessment (e.g., quantification) of a variety of different enzyme variants.

Bead oligonucleotides in accordance with embodiments described herein can include, e.g., nucleic acid barcode molecules comprising bead specific barcodes, capture sequences, complementary sequences to at least a portion of a first oligonucleotide, unique molecular identifiers or any combination thereof. In various embodiments, the reaction mixture or compositions can further comprise a bead 1130 coupled to a plurality of bead oligonucleotides 1130. In various embodiments, bead oligonucleotides can comprise a nucleic acid barcode molecule comprising a bead specific barcode. In various embodiments, bead oligonucleotides can comprise a capture sequence. In various embodiments, the capture sequence can be complementary to at least a portion of the first oligonucleotide of the plurality of RBO constructs. In various embodiments, bead oligonucleotides 1299 can, optionally, comprise a unique molecular identifier (UMI). In various embodiments, the capture sequence 1123 can be complementary to at least a portion of the first oligonucleotide 1202 of the plurality of RBO constructs 1202. In various embodiments, each of the bead oligonucleotides can comprise a bead specific barcode. In various embodiments, the bead specific barcode can identify an enzyme. In various embodiments, the UMI can identify a cell of origin.

III. Exemplary Methods

FIG. 14 illustrates steps in a method for assessing enzymatic activity 1400 according to various embodiments.

Step 1402 of the method includes combining a reactant barcoded oligonucleotide (RBO) construct with an amplification construct, a blocking construct, and an enzyme in a reaction mixture, according to various embodiments.

In various methods, the reactant barcoded oligonucleotide (RBO) construct may include a first oligonucleotide comprising a reaction barcode sequence and a first linker that connects the first oligonucleotide to a first reactant.

In various methods, the amplification construct may include a second oligonucleotide that is complementary to at least a portion of the first oligonucleotide and a second linker that connects the second oligonucleotide to a second reactant.

In various methods, the blocking construct may include a third oligonucleotide that is complementary to at least a portion of the first oligonucleotide. A quantity of the blocking construct may be greater than a quantity of the amplification construct according to various embodiments. A quantity of the blocking construct may be 10-fold more than a quantity of the amplification construct in accordance with some methods. A quantity of the blocking construct may be 100-fold more than a quantity of the amplification construct in accordance with other methods. In various methods, a quantity of the blocking construct may be in molar excess relative to a quantity of the amplification construct.

In various embodiments, the physical presence of the blocking construct may prevent a primer from binding, thereby, preventing an amplification reaction. In various embodiments, physically restricting movement of the blocking construct relative to the RBO construct comprises increases the binding affinity between the blocking construct and the first oligonucleotide.

Step 1404 of the method includes enzymatically reacting the first reactant with the second reactant to produce a reaction product, according to various embodiments. The reaction product may include the first reactant covalently linked to the second reactant.

Step 1406 of the method includes restricting movement of the of the amplification construct relative to the RBO construct, according to various embodiments. In various embodiments, the reaction product may restrict movement of the RBO construct and the amplification construct such that they remain in close proximity to one another.

In various embodiments, generation of a reaction product may bring the first oligonucleotide and the second oligonucleotide within close proximity, thereby, allowing hybridization of the first and second oligonucleotides to occur more frequently. Such conditions may allow the amplification construct to outcompete the blocking construct. Hybridization of the first and second oligonucleotides may facilitate a downstream amplification reaction that may be used to quantify an enzymatic reaction rate of the enzyme.

In various embodiments, unique reactants can be specifically selected as targets for specific enzymes. In various embodiments, the unique reactants can be targets for the same enzymes, however, reaction product generation can occur at different rates depending on which reactants are selected. In various embodiments, the reactants can be customized. In various embodiments, the reactants can be naturally occurring. In various embodiments, the reactants can be engineered.

Step 1408 of the method includes generating a reverse complement of the reaction barcode sequence with an amplification enzyme, according to various embodiments.

In various embodiments, the generating step may use an amplification enzyme. The amplification enzyme may be a polymerase in various methods. The amplification enzyme may be a reverse transcriptase. Some methods may use both a polymerase and a reverse transcriptase.

The method may include conducting an amplification reaction on the first oligonucleotide comprising the reaction barcode sequence to produce an extension product. The amplification reaction may comprise the step of annealing a second adapter to a second adapter binding site adjacent to a 3' end of the reaction barcode sequence and generating a reverse complement of the reaction barcode sequence. The step of annealing may further comprises annealing a first adapter to a first adapter binding site adjacent to a 5' end of the barcode sequence.

The method may include assessing an enzymatic activity of an enzyme based on an amplification product of the amplification reaction. Amplification products from the amplification reaction may be detectable. Amplification products from the amplification reaction may include a detectable label. Amplification products from the amplification reaction may encodes a detectable label. The detectable label may include a fluorescent molecule.

Amplification reactions in accordance with embodiments of the invention can include, e.g., methods to extend adapters/primers, polymerase chain reaction (PCR), reverse transcription or any combination thereof. In various embodiments, an amplification reaction can comprise PCR. In various embodiments, an amplification reaction can comprise reverse transcription.

The method may include identifying the enzyme using the reaction barcode sequence.

The method may include modifying an amino acid sequence of the enzyme. The step of modifying may occur before combining the RBO construct with the amplification construct, the blocking construct, and the enzyme in the reaction mixture. The step of modifying an amino acid sequence of the enzyme may include a CRISPR-mediated amino acid sequence modification.

The method may include increasing an affinity between the RBO construct and the blocking construct. Incorporation of LNAs may increase the affinity between the RBO construct and the blocking construct. In some methods, the second oligonucleotide comprises at least one LNA. In some methods, the second oligonucleotide comprises only LNAs.

In accordance with various methods, the first and second reactants may each comprise a protein. In accordance with various methods, the first and second reactants may each comprise a polynucleotide. In accordance with some methods, the portion of the first oligonucleotide that is complementary to the second oligonucleotide may comprise at least one LNA. In accordance with some methods, the portion of the first oligonucleotide that is complementary to the second oligonucleotide is comprised of only LNAs.

In various methods, the second oligonucleotide may include a non-reactive 3' end. The non-reactive '3 end may include a phosphorylated 3' end. In various embodiments, the second oligonucleotide can comprise a non-reactive 3' end. In various embodiments, the non-reactive end can be phosphorylated or designed to not be extendable using a polymerase.

In accordance with various methods, the first and second linkers may each comprise an inert polymer. The inert polymer may comprise polyethylene glycol (PEG).

FIG. 15 illustrates steps in a method for assessing enzymatic activity 1500 according to various embodiments.

Step 1502 of the method includes providing a partition comprising a reactant barcoded oligonucleotide (RBO) construct, an amplification construct, a blocking construct, and an enzyme. The partition may comprise anything that can compartmentalize a reaction mixture, e.g., wells, tubes, chambers, droplets, vials, flasks, or any other flexible or rigid housing. In various embodiments, the droplets can be water in oil. In various embodiments, the droplets be oil in water.

The reactant barcoded oligonucleotide (RBO) construct may include a first oligonucleotide comprising a reaction barcode sequence and a first linker that connects the first oligonucleotide to a first reactant.

The amplification construct may include a second oligonucleotide that may be complementary to at least a portion of the first oligonucleotide and a second linker that connects the second oligonucleotide to a second reactant.

The blocking construct may include a third oligonucleotide that may be complementary to at least a portion of the first oligonucleotide. In various embodiments, the physical presence of the blocking construct may prevent a primer from binding, thereby, preventing an amplification reaction. In various embodiments, physically restricting movement of the blocking construct relative to the RBO construct comprises increases the binding affinity between the blocking construct and the first oligonucleotide. In various embodiments, the second oligonucleotide can comprise a non-reactive 3' end. In various embodiments, the non-reactive end can be phosphorylated or designed to not be extendable using a polymerase.

Step 1504 of the method includes enzymatically reacting the first reactant with the second reactant to produce a reaction product. Enzymatically reacting the first reactant with the second reactant may produce a covalent linkage to produce the reaction product.

In various embodiments, unique reactants can be specifically selected as targets for specific enzymes. In various embodiments, the unique reactants can be targets for the same enzymes, however, reaction product generation can occur at different rates depending on which reactants are selected. In various embodiments, the reactants can be customized. In various embodiments, the reactants can be naturally occurring. In various embodiments, the reactants can be engineered.

Step 1506 of the method includes restricting movement of the of the amplification construct relative to the RBO construct forming a reaction complex. In various embodiments, the reaction product may restrict movement of the RBO construct and the amplification construct such that they remain in close proximity to one another.

In various embodiments, generation of a reaction product may bring the first oligonucleotide and the second oligonucleotide within close proximity, thereby, allowing hybridization of the first and second oligonucleotides to occur more frequently. Such conditions allow the amplification construct to outcompete the blocking construct. Hybridization of the first and second oligonucleotides may facilitate a downstream amplification reaction that may be used to quantify an enzymatic reaction rate of the enzyme.

Step 1508 of the method includes conducting an amplification reaction on the first oligonucleotide comprising the reaction barcode sequence. Amplification reactions in accordance with embodiments of the invention can include, e.g., methods to extend adapters/primers, polymerase chain reaction (PCR), reverse transcription or any combination thereof. In various embodiments, an amplification reaction can comprise PCR. In various embodiments, an amplification reaction can comprise reverse transcription.

Step 1510 of the method includes assessing enzymatic activity based on an amplification product of the amplification reaction.

In various methods, the partition includes a cell comprising the enzyme. The method may include lysing the cell to release the enzyme into the partition and contacting the reaction complex with the enzyme. The cell may include a plurality of different enzymes and the method may include contacting the reaction complex with each of the different enzymes.

In various methods, the partition may further include a bead that may be coupled to a plurality of bead oligonucleotides. The bead oligonucleotides may each include a nucleic acid barcode molecule comprising a bead-specific barcode. Additionally, the bead oligonucleotides may each include a capture sequence that is complementary to at least a portion of the first oligonucleotide sequences. The bead oligonucleotides may further include a unique molecular identifier (UMI). The method may include identifying the cell using the bead-specific barcode.

The method may include modifying an amino acid sequence of at least one of the enzymes using CRISPR prior to contacting the reaction complex with one or more of the enzymes. Modifying the amino acid sequence of at least one of the enzymes may include a CRISPR-mediated amino acid sequence modification. The method may include identifying the cell using the bead-specific barcode.

The method may include providing a plurality of partitions, each including a reactant barcoded oligonucleotide (RBO) construct, an amplification construct, a blocking construct, and an enzyme. The reactant barcoded oligonucleotide (RBO) construct may include a first oligonucleotide comprising a reaction barcode sequence and a first linker that connects the first oligonucleotide to a first reactant. The amplification construct may include a second oligonucleotide that is complementary to at least a portion of the first oligonucleotide and a second linker that connects the second oligonucleotide to a second reactant. The blocking construct may include a third oligonucleotide that is complementary to at least a portion of the first oligonucleotide. Steps 1502, 1504, 1506, 1508, and/or 1510 may be repeated for each partition. Any one of the other steps described herein may be repeated for each partition. The method may include comparing the enzymatic activity of each of the enzymes in each of the partitions using the barcode sequences that identify each of the reaction products and associated enzymes.

Any of the methods described herein can comprise the step of linking the reaction complexes (or extension products thereof) to a plurality of nucleic acid barcode molecules (e.g. nucleic acid barcode molecules that comprise capture sequences, e.g., a capture sequence disclosed herein). In various embodiments, the nucleic acid barcode molecules are coupled to a bead. In various embodiments, linking comprises hybridization. In various embodiments, linking comprises hybridization of two singled stranded nucleic acids. In various embodiments, each bead can be coupled to a plurality of bead oligonucleotides. In various embodiments, the bead oligonucleotides can comprise a nucleic acid barcode molecule comprising a bead-specific barcode and a capture sequence that is complementary to at least a portion of a portion of the first oligonucleotide, a portion of an extension product of the first oligonucleotide (e.g. a portion of any of, reverse complement of, or overlapping region of the following: adapter binding sequences, adapters, barcoded sequences), or a portion of a splint oligonucleotide. In various embodiments, the method can comprise hybridizing a portion of the bead oligonucleotides (e.g. a capture sequence) to a portion of the first oligonucleotides (e.g. a complementary sequence to the capture sequence). In various embodiments, the bead oligonucleotide can, optionally, comprise a UMI. In various embodiments, the bead oligonucleotides can each comprise a bead specific barcode and a capture sequence. In various embodiments, the bead oligonucleotides can each comprise a bead specific barcode, a UMI, and a capture sequence. In various embodiments, the linked nucleic acid barcode molecules and the reaction complexes (or extension products thereof) can be used to generate barcoded nucleic acid molecules comprising, e.g., a bead specific barcode or reverse complement thereof and a reaction barcode sequence or a reverse complement thereof.

A nucleic acid barcode molecule may be coupled to a bead (See Section V. SYSTEMS AND METHODS FOR SAMPLE COMPARTMENTALIZATION) and hybridize to at least a portion of a nucleotide sequence of a first oligonucleotide or an extension product or amplification product described herein, in accordance with various methods. In various methods, bead oligonucleotides described herein can include nucleic acid barcode molecules and vice versa. In various methods described herein, a reaction complex (e.g., an RBO construct hybridized to an amplification construct) forms after a reaction product has been generated by an enzyme. Once the reaction complex forms, a 3' end of a second oligonucleotide can be extended to generate a complementary sequence to the first oligo nucleotide (e.g., an extension product). The extended reaction complex can include a first adapter binding site of the first oligonucleotide hybridized to a first adapter binding site reverse complement of the extension product. The extended reaction complex can include a reaction barcode sequence of the first oligonucleotide hybridized to a reaction barcode sequence reverse complement of the extension product. The extended reaction complex can include a second adapter binding site of the first oligonucleotide hybridized to the second oligonucleotide of the extension product.

In various methods, a nucleic acid barcode molecule can be coupled to a complex including an RBO construct and a blocking construct, e.g., prior to a reaction product being formed. In various methods, an nucleic acid barcode molecule can be coupled to a reaction complex (e.g., an RBO construct and an amplification construct), e.g., after a reaction product is formed. In various methods, an extension product or copy thereof (e.g., post amplification) can hybridize to a nucleic acid construct. In various methods, a first oligonucleotide or copy thereof (e.g., post amplification) can hybridize to a nucleic acid construct.

In various methods, an extended reaction complex (e.g. a first oligonucleotide and an extension product) can undergo a process to dissociate from one another to form a single stranded extension product and a single stranded first oligonucleotide. In various methods, the process includes increasing a temperature to break hydrogen bonds between the two strands. Various methods include subsequent coupling of the single stranded molecules to a nucleic acid barcode molecule.

In various methods, a portion of a nucleotide sequence of the first oligonucleotide can hybridize to a nucleic acid barcode molecule. In various methods, the portion of the first oligonucleotide can hybridize to a capture sequence of the nucleic acid barcode molecule. In various methods, the portion of the first oligonucleotide can include a first adapter binding site. In various methods, the portion of the first oligonucleotide can include a second adapter binding site.

In various methods, a portion of a nucleotide sequence of the extension product can hybridize to a nucleic acid barcode molecule. In various methods, the portion of the extension product can hybridize to a capture sequence of the nucleic acid barcode molecule. In various methods, the portion of the extension product can include a first adapter binding site reverse complement. In various methods, the portion of the extension product can include a second adapter binding site reverse complement.

In various methods, an extended reaction complex can be amplified to generate copies of a first oligonucleotide and copies of an extension product. The amplification method can include polymerase chain reaction, in accordance with various methods.

In various methods, a portion of a nucleotide sequence of the copies of the first oligonucleotide can hybridize to a nucleic acid barcode molecules. In various methods, the portion of the copies of the first oligonucleotide can hybridize to capture sequences of the nucleic acid barcode molecules. In various methods, the portion of the copies of the first oligonucleotides can include first adapter binding sites. In various methods, the portions of the copies of the first oligonucleotides can include the second adapter binding sites.

In various methods, a portion of a nucleotide sequence of the copies of the extension product can hybridize to nucleic acid barcode molecules. In various methods, the portions of the copies of the extension products can hybridize to capture sequences of the nucleic acid barcode molecules. In various methods, the portion of the copies of the extension products can include first adapter binding site reverse complements. In various methods, the portion of the copies of the extension products can include second adapter binding site reverse complements.

Various methods can employ splint oligonucleotides. For example, splint oligonucleotides can hybridize to a single stranded portion of a first oligonucleotide and a single stranded portion of a second oligonucleotide to couple the first oligonucleotide to the second oligonucleotide. In various methods, a splint oligonucleotide can include a complementary sequence to a portion of a nucleotide sequence of a nucleic acid barcode molecule (e.g., bead oligonucleotide) and can include a complementary sequence to a portion of a first oligonucleotide or copies of a first oligonucleotide resulting from an amplification reaction. In some methods, the splint oligonucleotide can include a nucleotide sequence that is complementary to a first adapter binding site of the first oligonucleotide or copy thereof. In alternative methods, the splint oligonucleotide can include a nucleotide sequence that is complementary to a second adapter binding site of the first oligonucleotide or a copy thereof.

In various methods, a splint oligonucleotide can include a complementary sequence to a portion of a nucleotide sequence of a nucleic acid barcode molecule (e.g., bead oligonucleotide) and can include a complementary sequence to a portion of a nucleotide sequence of an extension product or copies of an extension product resulting from an amplification reaction. In some methods, the splint oligonucleotide can include a nucleotide sequence that is complementary to a first adapter binding site reverse complement of the extension product or copy thereof. In alternative methods, the splint oligonucleotide can include a nucleotide sequence that is complementary to a second oligonucleotide of the extension product or a copy thereof.

In various methods, the splint oligonucleotide can hybridize to both the bead oligonucleotide and the portion of a nucleotide sequence of the first oligonucleotide to join the bead oligonucleotide to the first oligonucleotide of copy thereof. In some methods, the hybridized splint oligonucleotide causes a 5' end of the bead oligonucleotide to abut or be adjacent to a 3' end of a first oligonucleotide or copy thereof. In some methods, the hybridized splint oligonucleotide causes a 3' end of the bead oligonucleotide to abut or be adjacent to a 5' end of a first oligonucleotide or copy thereof.

In various methods, the barcoded products can be quantitated using the methods described in Section V. SYSTEMS AND METHODS FOR SAMPLE COMPARTMENTAL- IZATION. For example, a UMI may provide a unique identifier of the starting analyte (e.g., barcoded product specific for a target enzyme) molecule that was captured, in order to allow quantitation of the number of original reaction complexes, in accordance with the various methods. Beneficially, even following any subsequent amplification of the contents of a given partition (e.g., a droplet, well, or vessel), the number of different UMIs can be indicative of the quantity of reaction complexes originating from the given partition, and thus from the biological particle (e.g., cell or target enzyme). Alternatively, or in addition to, imaging may be used to characterize a quantity of amplified barcoded products in the partition.

Any of the methods described herein can comprise the step of identifying a cell of origin using the bead specific barcode. In various embodiments, the bead specific barcode can identify an enzyme or modified enzyme.

Any of the methods described herein can comprise the step of modifying an amino acid sequence of one or more of the enzymes. In various embodiments, being able to easily modify the amino acid sequence of one or more of the enzymes and to then be able to quantify an enzymatic activity for each of the enzymes allows for massive parallel enzymatic assays of a pool of modified enzymes allowing for fast optimization (e.g. increased or decreased enzymatic activity based on a specified application by a researcher).

Any of the methods described herein can comprise the step of modifying an amino acid sequence of one or more of the enzymes comprises a CRISPR-mediated amino acid sequence modification. In various embodiments, using CRISPR gene editing enables modification of many enzymes in parallel. In various embodiments, the step of modifying the amino acid sequence of the one or more enzymes occurs prior to the step of contacting the reactant complex with the enzyme.

Any of the methods described herein can comprise the step of comparing enzymatic activity between two or more enzymes having different amino acid sequences.

Any of the methods described herein may include use of partitions which can include, e.g., cells lysed cells, enzymes expressed by cells, adapter sequences, reaction complexes, or any combination thereof. Any of the methods described herein may relate to creating such partitions. In various embodiments, a partition can comprise a cell. In various embodiments, the enzyme can be expressed by the cell. In various embodiments, the partition can comprise a lysed cell which can cause release of the enzyme into the partition which can facilitate the step of contacting the enzyme with the reaction complex. In various embodiments, the cell can comprise a plurality of different enzymes. In various embodiments, many cells can each comprise a different set of enzymes. In various embodiments, the methods described herein may include many cells and each cell can comprise a single enzyme variant.

Any of the methods described herein can comprise the step of screening a plurality of enzymes can be useful in functional assays. For example, glucose metabolism requires many different enzymatic reactions. Such embodiments can allow for determination of mechanisms and actions and impact of novel therapeutics. In various embodiments, screening a plurality of enzymes can be useful in characterizing cell pathways.

IV. Exemplary Kits

In various aspects of the disclosure, kits are provided for carrying out the methods described herein. Various kits may include a reactant barcoded oligonucleotide (RBO) construct, an amplification construct, and a blocking construct.

Various kits may include a reactant barcoded oligonucleotide (RBO) construct. RBO constructs may include a first oligonucleotide comprising a reaction barcode sequence. RBO constructs may include a first linker that connects the first oligonucleotide to a first reactant.

Various kits may include an amplification construct. Amplification constructs may include a second oligonucleotide that is complementary to at least a portion of the first oligonucleotide. Amplification constructs may include a second linker that connects the second oligonucleotide to a second reactant.

Various kits may include a blocking construct. Blocking constructs may include a third oligonucleotide that is complementary to at least a portion of the first oligonucleotide.

Various kits may include a plurality of first adapters including a sequence that may be complementary to at least a portion of the first oligonucleotide.

Various kits may include a plurality of second adapters including a sequence that may be complementary to at least a portion of the first oligonucleotide.

Various kits may include one or more reagents for conducting an amplification reaction.

Various kits may include a bead coupled to a plurality of bead oligonucleotides. Each of the plurality of bead oligonucleotides may include a nucleic acid barcode molecule including a bead-specific barcode and a capture sequence. The capture sequence may be complementary to at least a portion of the first oligonucleotide of the RBO construct.

Various kits may include one or more reagents for conducting a CRISPR modification reaction.

In various kits, the first reactant and the second reactant may be configured to be covalently linked to one another by an enzymatic reaction.

In various embodiments, kits can comprise one or more reagents for conducting an amplification reaction. In various embodiments, reagents can comprise buffers, nucleotides (e.g. dNTPs), Taq polymerase, and adapters.

In various embodiments, kits can comprise a bead coupled to a plurality of third oligonucleotides, wherein the plurality of third oligonucleotide can each comprise a nucleic acid barcode molecule comprising a unique molecular identifier (UMI) and a capture sequence, wherein the capture sequence can be complementary to at least a portion of the first oligonucleotide of the RBO construct. In various embodiments, the third oligonucleotide can comprise a bead specific barcode and a capture sequence. In various embodiments, the third oligonucleotide can comprise only a capture sequence. In various embodiments, the third oligonucleotide can comprise a bead specific barcode and a capture sequence. In various embodiments, the third oligonucleotide can comprise a bead specific barcode, a UMI, and a capture sequence.

In various embodiments, kits can comprise one or more reagents for conducting a CRISPR modification reaction. In various embodiments, the reagents can comprise one or more exogenous CRISPR-associated endonuclease (Cas) molecules, one or more exogenous insert oligonucleotide comprising a tagging sequence, a plurality of exogenous targeting guide ribonucleic acids (gRNAs) configured to modify a targeting genomic locus in the cell, and a plurality of exogenous tagging gRNAs configured to modify a tagging genomic locus in the cell.

V. Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion or a well. A partition can comprise one or more other partitions.

A partition can include one or more particles. A partition can include one or more types of particles. For example, a partition of the present disclosure can comprise one or more biological particles and/or macromolecular constituents thereof. A partition can comprise one or more beads. A partition can comprise one or more gel beads. A partition can comprise one or more cell beads. A partition can include a single gel bead, a single cell bead, or both a single cell bead and single gel bead. A partition can include one or more reagents. Alternatively, a partition can be unoccupied. For example, a partition may not comprise a bead.

Unique identifiers, such as barcodes, can be injected into the droplets prior to, subsequent to, or concurrently with droplet generation, such as via a bead, as described elsewhere herein.

The methods and systems of the present disclosure can comprise methods and systems for generating one or more partitions such as droplets. The droplets can comprise a plurality of droplets in an emulsion. In various examples, the droplets can comprise droplets in a colloid. In various cases, the emulsion can comprise a microemulsion or a nanoemulsion. In various examples, the droplets can be generated with aid of a microfluidic device and/or by subjecting a mixture of immiscible phases to agitation (e.g., in a container). In various cases, a combination of the mentioned methods can be used for droplet and/or emulsion formation.

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet-based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with beads, it will be appreciated that the sample fluid volume, e.g., including co-partitioned biological particles and/or beads, within the partitions may be less than about 90% of the above-described volumes, less than about 80%, less than about 70%, less than about 60%, less than about 50%, less than about 40%, less than about 30%, less than about 20%, or less than about 10% of the above-described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions, at least about 10,000,000 partitions, at least about 50,000,000 partitions, at least about 100,000,000 partitions, at least about 500,000,000 partitions, at least about 1,000, 000,000 partitions, or more partitions can be generated or otherwise provided. Moreover, the plurality of partitions may comprise both unoccupied partitions (e.g., empty partitions) and occupied partitions.

Droplets can be formed by creating an emulsion by mixing and/or agitating immiscible phases. Mixing or agitation may comprise various agitation techniques, such as vortexing, pipetting, tube flicking, or other agitation techniques. In various cases, mixing or agitation may be performed without using a microfluidic device. In various examples, the droplets may be formed by exposing a mixture to ultrasound or sonication. Systems and methods for droplet and/or emulsion generation by agitation are described in International Application No. PCT/US20/17785, which is entirely incorporated herein by reference for all purposes.

V.A. Microfluidic Systems:

Microfluidic devices or platforms comprising microfluidic channel networks (e.g., on a chip) can be utilized to generate partitions such as droplets and/or emulsions as described herein. Methods and systems for generating partitions such as droplets, methods of encapsulating biological particles in partitions, methods of increasing the throughput of droplet generation, and various geometries, architectures, and configurations of microfluidic devices and channels are described in U.S. Patent Publication Nos. 2019/0367997 and 2019/0064173, each of which is entirely incorporated herein by reference for all purposes.

In various examples, individual particles can be partitioned to discrete partitions by introducing a flowing stream of particles in an aqueous fluid into a flowing stream or reservoir of a non-aqueous fluid, such that droplets may be generated at the junction of the two streams/reservoir, such as at the junction of a microfluidic device provided elsewhere herein.

The methods of the present disclosure may comprise generating partitions and/or encapsulating particles, such as biological particles, in various cases, individual biological particles such as single cells. In various examples, reagents may be encapsulated and/or partitioned (e.g., co-partitioned with biological particles) in the partitions. Various mechanisms may be employed in the partitioning of individual particles. An example may comprise porous membranes through which aqueous mixtures of cells may be extruded into fluids (e.g., non-aqueous fluids).

The partitions can be flowable within fluid streams. The partitions may comprise, for example, micro-vesicles that have an outer barrier surrounding an inner fluid center or core. In various cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In various examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In various cases, partitions among a plurality of partitions may contain at most one biological particle (e.g., bead, DNA, cell or cellular material). In various embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

Figure 3:
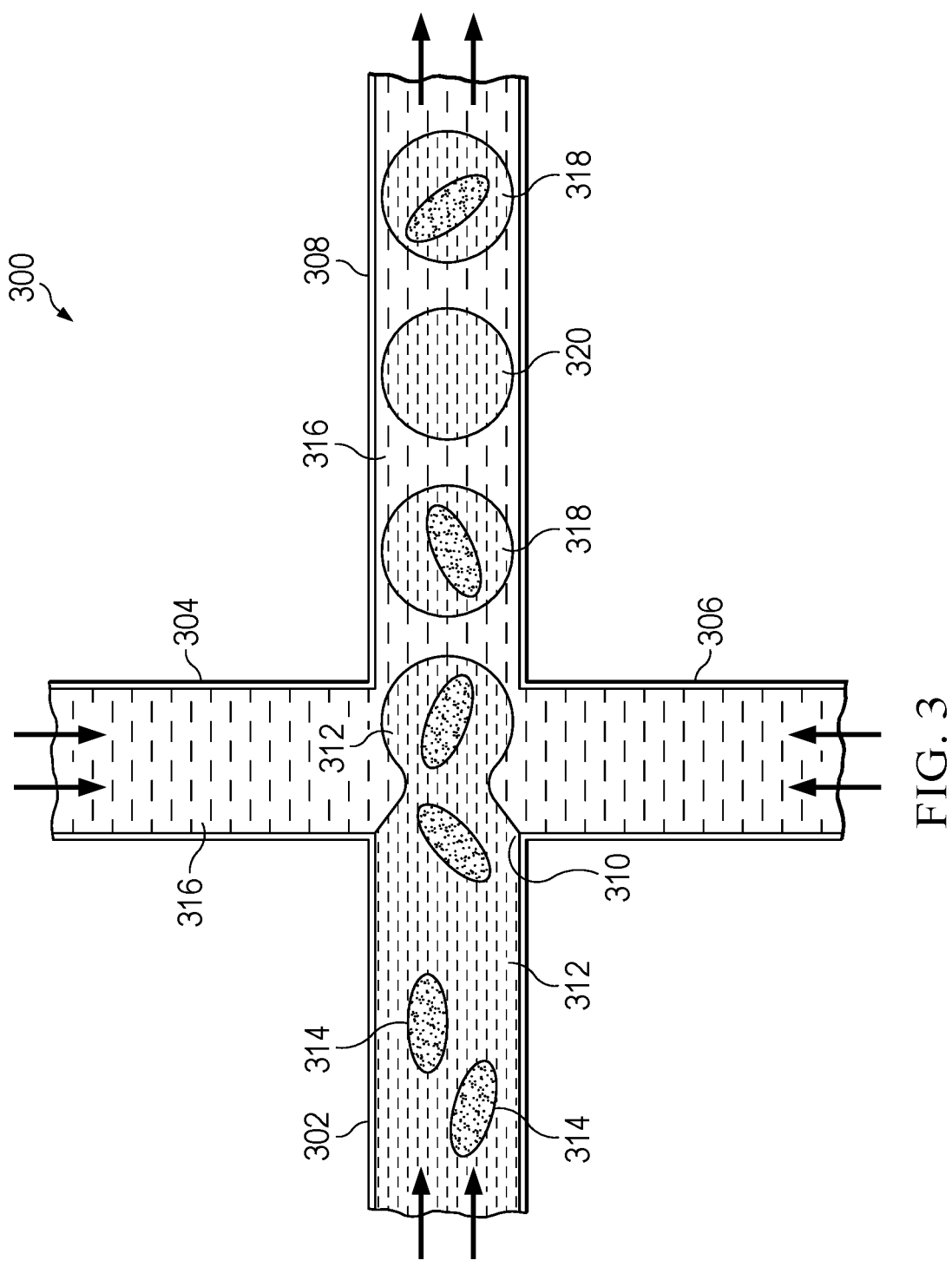
FIG. 3 is a schematic illustration showing an example of a microfluidic channel structure for partitioning individual analyte carriers according to various embodiments.

FIG. 3 shows an example of a microfluidic channel structure 306 for partitioning individual biological particles according to various embodiments. The channel structure 306 can include channel segments 302, 304, 306 and 308 communicating at a channel junction 310. In operation, a first aqueous fluid 312 that includes suspended biological particles (or cells) 314 may be transported along channel segment 302 into junction 310, while a second fluid 316 that is immiscible with the aqueous fluid 312 is delivered to the junction 310 from each of channel segments 304 and 306 to create discrete droplets 318, 320 of the first aqueous fluid 312 flowing into channel segment 308, and flowing away from junction 310. The channel segment 308 may be fluidically coupled to an outlet reservoir where the discrete droplets can be stored and/or harvested. A discrete droplet generated may include an individual biological particle 314 (such as droplets 318). A discrete droplet generated may include more than one individual biological particle 314 (not shown in FIG. 3). A discrete droplet may contain no biological particle 314 (such as droplet 320). Each discrete partition may maintain separation of its own contents (e.g., individual biological particle 314) from the contents of other partitions.

The second fluid 316 can comprise an oil, such as a fluorinated oil, that includes a fluorosurfactant for stabilizing the resulting droplets, for example, inhibiting subsequent coalescence of the resulting droplets 318, 320. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 318, containing one or more biological particles 314, and (2) unoccupied droplets 320, not containing any biological particles 314. Occupied droplets 318 may comprise singly occupied droplets (having one biological particle) and multiply occupied droplets (having more than one biological particle). As described elsewhere herein, in various cases, the majority of occupied partitions can include no more than one biological particle per occupied partition and various of the generated partitions can be unoccupied (of any biological particle). In various cases, though, various of the occupied partitions may include more than one biological particle. In various cases, the partitioning process may be controlled such that fewer than about 25% of the occupied partitions contain more than one biological particle, and in many cases, fewer than about 20% of the occupied partitions have more than one biological particle, while in various cases, fewer than about 10% or even fewer than about 5% of the occupied partitions include more than one biological particle per partition.

In various cases, it may be desirable to minimize the creation of excessive numbers of empty partitions, such as to reduce costs and/or increase efficiency. While this minimization may be achieved by providing a sufficient number of biological particles (e.g., biological particles 314) at the partitioning junction 310, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In various cases, flows can be controlled so as to present a non-Poissonian distribution of single-occupied partitions while providing lower levels of unoccupied partitions (e.g., no more than about 50%, about 25%, or about 10% unoccupied). The above noted ranges of unoccupied partitions can be achieved while still providing any of the single occupancy rates described above.

As will be appreciated, the above-described occupancy rates are also applicable to partitions that include both biological particles and additional reagents, such as beads (e.g., gel beads) carrying nucleic acid barcode molecules (e.g., oligonucleotides).

In various examples, a partition of the plurality of partitions may comprise a single biological particle (e.g., a single cell or a single nucleus of a cell). In various examples, a partition of the plurality of partitions may comprise multiple biological particles. Such partitions may be referred to as multiply occupied partitions, and may comprise, for example, two, three, four or more cells and/or beads (e.g., beads) comprising nucleic acid barcode molecules within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in various cases greater than about 80%, 90%, 95%, or higher.

Microfluidic systems for partitioning are further described in U.S. Patent Application Pub. No. US 2015/0376609, which is hereby incorporated by reference in its entirety.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, e.g., nucleic acid barcode molecules or barcoded oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 (e.g., cells or macromolecular constituents of cells that have been contacted with an aptamer-payload complex or internalization complex disclosed herein, e.g., depicted in FIG. 1, 13, 14, 15) along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested. As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

V.B. Controlled Partitioning:

In various aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
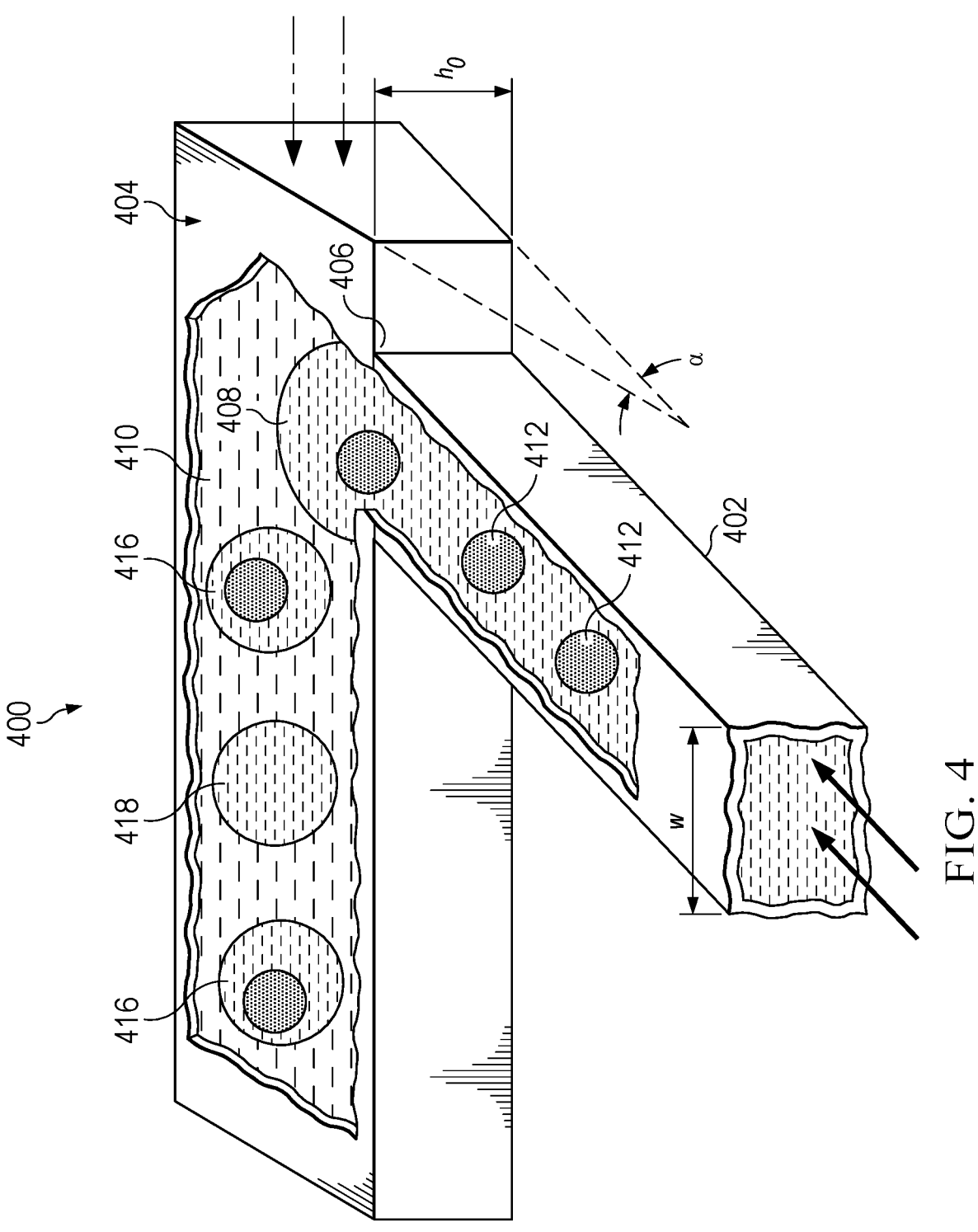
FIG. 4 is a schematic illustration showing an example of a microfluidic channel structure for the controlled partitioning of beads into discrete droplets according to various embodiments.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

In various instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 202 and/or the relative flow rates of the fluids in the channel segment 402 and the separate channel. In various instances, the beads can be introduced into the channel segment 402 from a plurality of different channels, and the frequency controlled accordingly.

In various instances, the aqueous fluid 408 in the channel segment 402 can comprise biological particles. In various instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In various instances, the biological particles can be introduced into the channel segment 402 from a plurality of different channels, and the frequency controlled accordingly. In various instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In various instances, the second fluid 410 may not be subjected to and/or directed to any flow in or out of the reservoir 404. For example, the second fluid 410 may be substantially stationary in the reservoir 404. In various instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

Systems and methods for controlled partitioning are described further in PCT/US2018/047551, the disclosure of which is hereby incorporated by reference in its entirety.

V.C. Beads:

Nucleic acid barcode molecules may be delivered to a partition (e.g., a droplet or well) via a solid support or carrier (e.g., a bead). In various cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

The solid support may be a bead. A solid support, e.g., a bead, may be porous, non-porous, hollow, solid, semi-solid, and/or a combination thereof. Beads may be solid, semi-solid, semi-fluidic, fluidic, and/or a combination thereof. In various instances, a solid support, e.g., a bead, may be at least partially dissolvable, disruptable, and/or degradable. In various cases, a solid support, e.g., a bead, may not be degradable. In various cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In various cases, the solid support, e.g., the bead, may be a silica bead. In various cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual biological particle to the particular partition. Barcodes may be delivered, for example on a nucleic acid molecule (e.g., via a nucleic acid barcode molecule), to a partition via any suitable mechanism. Nucleic acid barcode molecules can be delivered to a partition via a bead. Beads are described in further detail below.

In various cases, nucleic acid barcode molecules can be initially associated with the bead and then released from the bead. Release of the nucleic acid barcode molecules can be passive (e.g., by diffusion out of the bead). In addition or alternatively, release from the bead can be upon application of a stimulus which allows the nucleic acid barcode molecules to dissociate or to be released from the bead. Such stimulus may disrupt the bead, an interaction that couples the nucleic acid barcode molecules to or within the bead, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

Methods and systems for partitioning barcode carrying beads into droplets are provided herein, and in in US. Patent Publication Nos. 2019/0367997 and 2019/0064173, and International Application No. PCT/US20/17785, the disclosure of which are herein incorporated by reference in their entireties for all purposes.

A bead may be porous, non-porous, solid, semi-solid, semi-fluidic, fluidic, and/or a combination thereof. In various instances, a bead may be dissolvable, disruptable, and/or degradable. Degradable beads, as well as methods for degrading beads, are described in PCT/US2014/044398, the disclosure of which is hereby incorporated by reference in its entirety. In various cases, any combination of stimuli, e.g., stimuli described in PCT/US2014/044398 and US Patent Application Pub. No. 2015/0376609, the disclosures of which are hereby incorporated by reference in their entireties, may trigger degradation of a bead. For example, a change in pH may enable a chemical agent (e.g., DTT) to become an effective reducing agent.

In various cases, a bead may not be degradable. In various cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In various cases, the bead may be a silica bead. In various cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In various cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In various cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In various cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in various cases less than 15%, less than 10%, less than 5%, or less.

A bead may comprise natural and/or synthetic materials. For example, a bead can comprise a natural polymer, a synthetic polymer or both natural and synthetic polymers. See, e.g., PCT/US2014/044398, the disclosure of which is hereby incorporated by reference in its entirety. Beads may also be formed from materials other than polymers, including lipids, micelles, ceramics, glass-ceramics, material composites, metals, other inorganic materials, and others.

In various cases, the bead may comprise covalent or ionic bonds between polymeric precursors (e.g., monomers, oligomers, linear polymers), nucleic acid barcode molecules (e.g., oligonucleotides), primers, and other entities. In various cases, the covalent bonds can be carbon-carbon bonds, thioether bonds, or carbon-heteroatom bonds.

In various cases, a plurality of nucleic acid barcode molecules may be attached to a bead. The nucleic acid barcode molecules may be attached directly or indirectly to the bead. In various cases, the nucleic acid barcode molecules may be covalently linked to the bead. In various cases, the nucleic acid barcode molecules are covalently linked to the bead via a linker. In various cases, the linker is a degradable linker. In various cases, the linker comprises a labile bond configured to release said nucleic acid barcode molecule of said plurality of nucleic acid barcode molecules. In various cases, the labile bond comprises a disulfide linkage.

Activation of disulfide linkages within a bead can be controlled such that only a small number of disulfide linkages are activated. Methods of controlling activation of disulfide linkages within a bead are described in PCT/US2014/044398, the disclosure of which is hereby incorporated by reference in its entirety.

In various cases, a bead may comprise an acrydite moiety, which in certain aspects may be used to attach one or more nucleic acid barcode molecules (e.g., barcode sequence, nucleic acid barcode molecule, barcoded oligonucleotide, primer, or another oligonucleotide) to the bead. Acrydite moieties, as well as their uses in attaching nucleic acid molecules to beads, are described in PCT/US2014/044398, the disclosure of which is hereby incorporated by reference in its entirety.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule, e.g., a nucleic acid barcode molecule described herein.

In various cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. Exemplary precursors comprising functional groups are described in PCT/US2014/044398, the disclosure of which is hereby incorporated by reference in its entirety.

Other non-limiting examples of labile bonds that may be coupled to a precursor or bead are described in PCT/US2014/044398, the disclosure of which is hereby incorporated by reference in its entirety. A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. See, e.g., PCT/US2014/044398, the disclosure of which is hereby incorporated by reference in its entirety. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., NEXTERA® for ILLUMINA®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Alternatively, or in addition, species may be partitioned in a partition (e.g., droplet) during or subsequent to partition formation. Such species may include, without limitation, the abovementioned species that may also be encapsulated in a bead.

In various cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In various cases, the pre-defined concentration of the primer can be limited by the process of producing oligonucleotide bearing beads.

V.D. Nucleic Acid Barcode Molecules:

A nucleic acid barcode molecule may contain one or more barcode sequences. A plurality of nucleic acid barcode molecules may be coupled to a bead. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

Nucleic acid barcode molecules can comprise one or more functional sequences for coupling to an analyte or analyte tag such as a reporter oligonucleotide. Such functional sequences can include, e.g., a template switch oligonucleotide (TSO) sequence, a primer sequence (e.g., a poly T sequence, or a nucleic acid primer sequence complementary to a target nucleic acid sequence and/or for amplifying a target nucleic acid sequence, a random primer, and a primer sequence for messenger RNA).

In various cases, the nucleic acid barcode molecule can further comprise a unique molecular identifier (UMI). In various cases, the nucleic acid barcode molecule can comprise one or more functional sequences, for example, for attachment to a sequencing flow cell, such as, for example, a P5 sequence (or a portion thereof) for ILLUMINA® sequencing. In various cases, the nucleic acid barcode molecule or derivative thereof (e.g., oligonucleotide or poly-nucleotide generated from the nucleic acid molecule) can comprise another functional sequence, such as, for example, a P7 sequence (or a portion thereof) for attachment to a sequencing flow cell for Illumina sequencing. In various cases, the nucleic acid molecule can comprise an R1 primer sequence for Illumina sequencing. In various cases, the nucleic acid molecule can comprise an R2 primer sequence for Illumina sequencing. In various cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In various cases, a downstream procedure may extend the partial sequence, or derivative thereof, to achieve a full sequence of the partial sequence, or derivative thereof.

Examples of such nucleic acid molecules (e.g., oligo-nucleotides, polynucleotides, etc.) and uses thereof, as may be used with compositions, devices, methods and systems of the present disclosure, are provided in U.S. Patent Pub. Nos. 2014/0378345 and 2015/0376609, the disclosures of which are incorporated by reference herein in their entireties.

Figure 5:
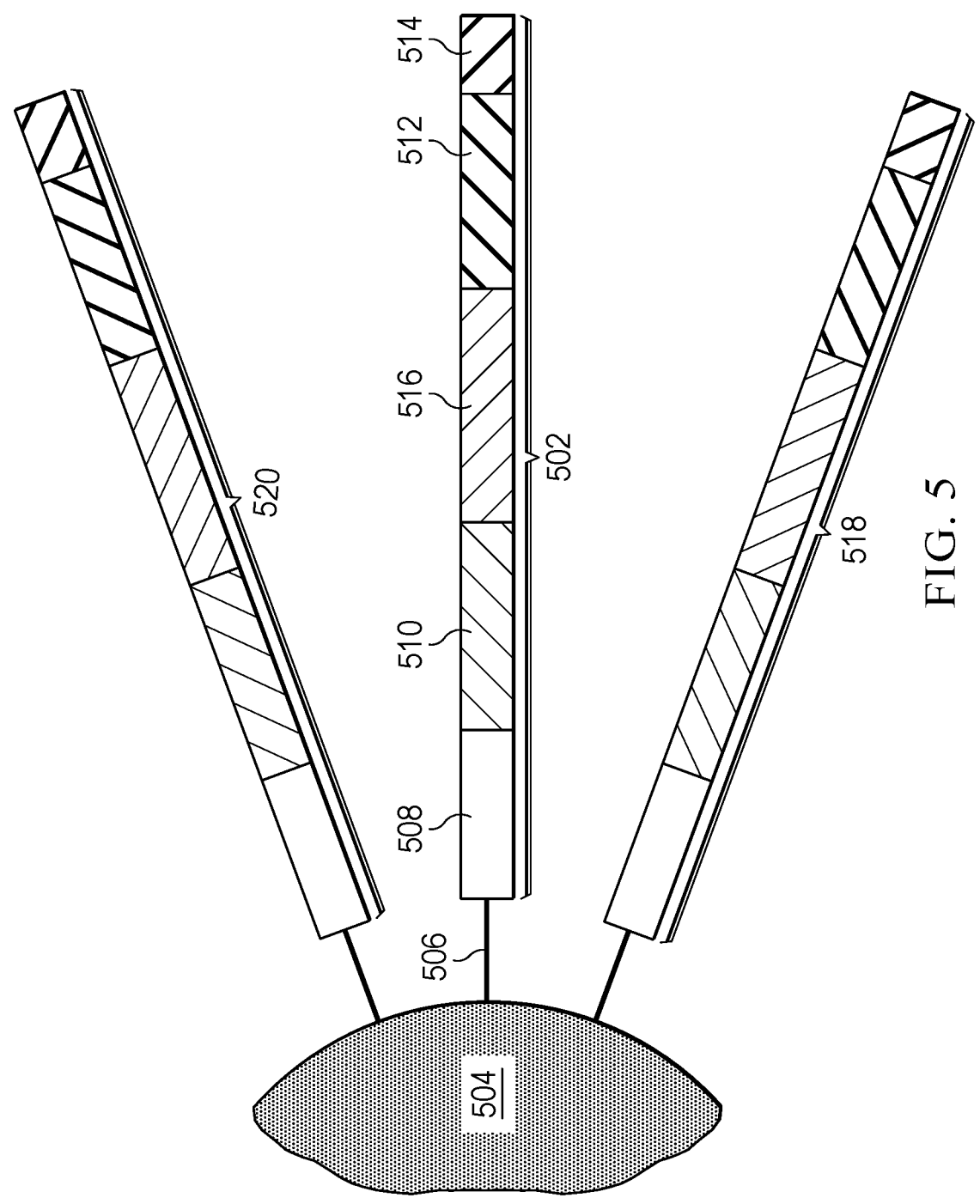
FIG. 5 illustrates an example of a barcode-carrying bead according to various embodiments.

FIG. 5 illustrates an example of a barcode carrying bead. A nucleic acid barcode molecule 502 can be coupled to a bead 504 by a releasable linkage 506, such as, for example, a disulfide linker. The same bead 504 may be coupled (e.g., via releasable linkage) to one or more other nucleic acid barcode molecules 518, 520. The nucleic acid barcode molecule 502 may be or comprise a barcode. As noted elsewhere herein, the structure of the barcode may comprise a number of sequence elements. The nucleic acid barcode molecule 502 may comprise a functional sequence 508 that may be used in subsequent processing. For example, the functional sequence 508 may include one or more of a sequencer specific flow cell attachment sequence (e.g., a P5 sequence for ILLUMINA® sequencing systems) and a sequencing primer sequence (e.g., a R1 primer for ILLU-MINA® sequencing systems), or partial sequence(s) thereof. The nucleic acid barcode molecule 502 may comprise a barcode sequence 510 for use in barcoding the sample (e.g., DNA, RNA, protein, etc.). In various cases, the barcode sequence 510 can be bead-specific such that the barcode sequence 510 is common to all nucleic acid barcode molecules (e.g., including nucleic acid barcode molecule 502) coupled to the same bead 504. Alternatively or in addition, the barcode sequence 510 can be partition-specific such that the barcode sequence 510 is common to all nucleic acid barcode molecules coupled to one or more beads that are partitioned into the same partition. The nucleic acid barcode molecule 502 may comprise sequence 512 complementary to an analyte of interest, e.g., a priming sequence. Sequence 512 can be a poly-T sequence complementary to a poly-A tail of an mRNA analyte, a targeted priming sequence, and/or a random priming sequence. The nucleic acid barcode molecule 502 may comprise an anchoring sequence 514 to ensure that the specific priming sequence 512 hybridizes at the sequence end (e.g., of the mRNA). For example, the anchoring sequence 514 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid barcode molecule 502 may comprise a unique molecular identifying (UMI) sequence 516. In various cases, the unique molecular identifying sequence 516 may comprise from about 5 to about 8 nucleotides. Alternatively, the unique molecular identifying sequence 516 may compress less than about 5 or more than about 8 nucleotides. The unique molecular identifying sequence 516 may be a unique sequence that varies across individual nucleic acid barcode molecules (e.g., 502, 518, 520, etc.) coupled to a single bead (e.g., bead 504). In various cases, the unique molecular identifying sequence 516 may be a random sequence (e.g., such as a random N-mer sequence). For example, the UMI 516 may provide a unique identifier of the starting analyte (e.g., mRNA) molecule that was captured, in order to allow quantitation of the number of original expressed RNA molecules. As will be appreciated, although FIG. 5 shows three nucleic acid barcode molecules 502, 518, 520 coupled to the surface of the bead 504, an individual bead may be coupled to any number of individual nucleic acid barcode molecules, for example, from one to tens to hundreds of thousands, millions, or even a billion of individual nucleic acid barcode molecules. The respective barcodes for the individual nucleic acid barcode molecules can comprise both common sequence segments or relatively common sequence segments (e.g., 508, 510, 512, etc.) and variable or unique sequence segments (e.g., 516) between different individual nucleic acid barcode molecules coupled to the same bead.

In operation, a biological particle (e.g., cell, DNA, RNA, etc.) can be co-partitioned along with a barcode bearing bead 504. The nucleic acid barcode molecules 502, 518, 520 can be released from the bead 504 in the partition. By way of example, in the context of analyzing sample RNA, the poly-T segment (e.g., 512) of one of the released nucleic acid barcode molecules (e.g., 502) can hybridize to the poly-A tail of a mRNA molecule. Reverse transcription may result in a cDNA transcript of the mRNA, but which transcript includes each of the sequence segments 508, 510, 516 of the nucleic acid barcode molecule 502. Because the nucleic acid barcode molecule 502 comprises an anchoring sequence 514, it will more likely hybridize to and prime reverse transcription at the sequence end of the poly-A tail of the mRNA. Within any given partition, all of the cDNA transcripts of the individual mRNA molecules may include a common barcode sequence segment 510. However, the transcripts made from the different mRNA molecules within a given partition may vary at the unique molecular identifying sequence 516 segment (e.g., UMI segment). Beneficially, even following any subsequent amplification of the contents of a given partition, the number of different UMIs 516 can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in various cases, the nucleic acid barcode molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where analytes from the sample are captured by the nucleic acid barcode molecules in a partition (e.g., by hybridization), captured analytes from various partitions may be collected, pooled, and subjected to further processing (e.g., reverse transcription, adapter attachment, amplification, clean up, sequencing). For example, in cases wherein the nucleic acid molecules from the sample remain attached to the bead, the beads from various partitions may be collected, pooled, and subjected to further processing (e.g., reverse transcription, adapter attachment, amplification, clean up, sequencing). In other instances, one or more of the processing methods, e.g., reverse transcription, may occur in the partition. For example, conditions sufficient for barcoding, adapter attachment, reverse transcription, or other nucleic acid processing operations may be provided in the partition and performed prior to clean up and sequencing.

In various instances, a bead may comprise a capture sequence or binding sequence configured to bind to a corresponding capture sequence or binding sequence. In various instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, etc. A bead may comprise any number of different capture sequences. In various instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In various instances, the different capture sequences or binding sequences may be configured to facilitate analysis of a same type of analyte. In various instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, an biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In various instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 6:
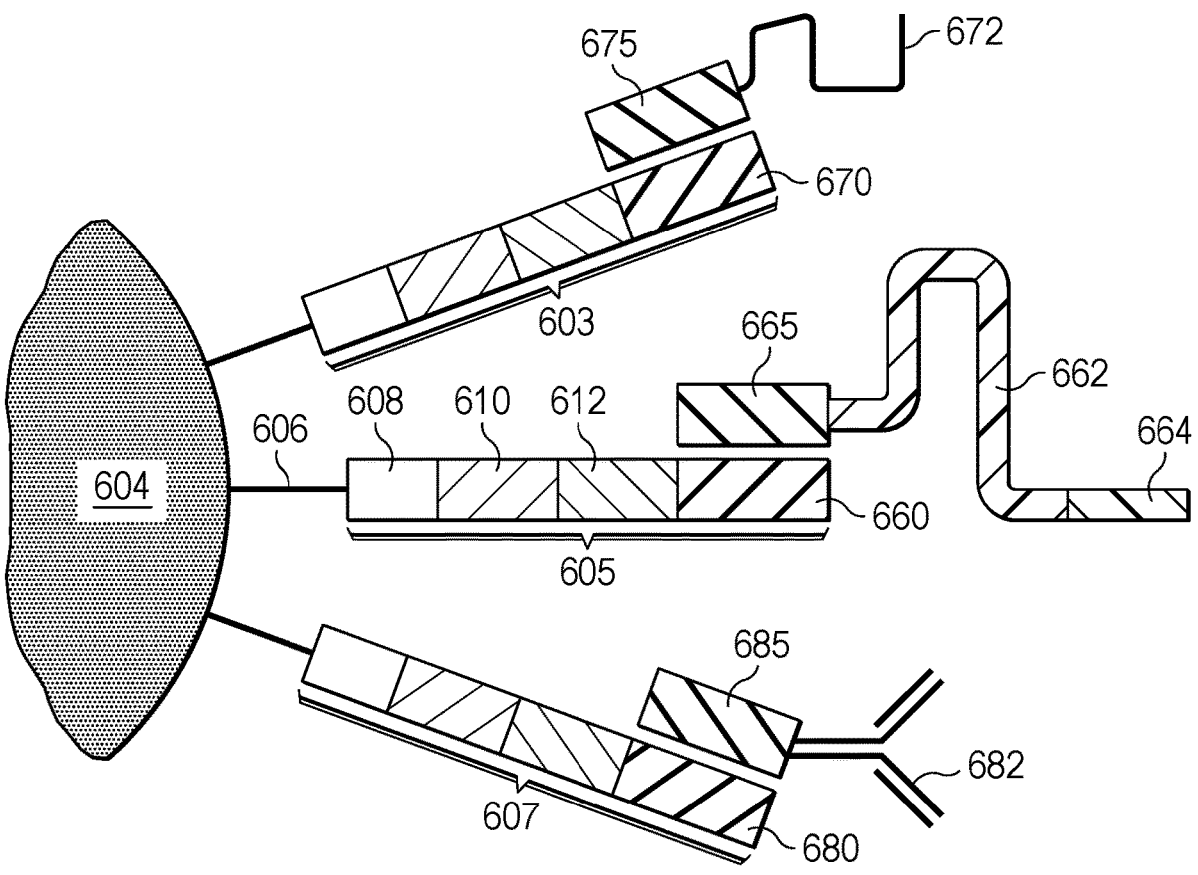
FIG. 6 illustrates another example of a barcode-carrying bead according to various embodiments.

FIG. 6 illustrates another example of a barcode carrying bead. A nucleic acid barcode molecule 605, such as an oligonucleotide, can be coupled to a bead 604 by a releasable linkage 606, such as, for example, a disulfide linker. The nucleic acid barcode molecule 605 may comprise a first capture sequence 660. The same bead 604 may be coupled (e.g., via releasable linkage) to one or more other nucleic acid molecules 603, 607 comprising other capture sequences. The nucleic acid barcode molecule 605 may be or comprise a barcode. As noted elsewhere herein, the structure of the barcode may comprise a number of sequence elements, such as a functional sequence 608 (e.g., flow cell attachment sequence, sequencing primer sequence, etc.), a barcode sequence 610 (e.g., bead-specific sequence common to bead, partition-specific sequence common to partition, etc.), and a unique molecular identifier 612 (e.g., unique sequence within different molecules attached to the bead), or partial sequences thereof. The capture sequence 660 may be configured to attach to a corresponding capture sequence 665. In various instances, the corresponding capture sequence 665 may be coupled to another molecule that may be an analyte or an intermediary carrier. For example, as illustrated in FIG. 6, the corresponding capture sequence 665 is coupled to a guide RNA molecule 662 comprising a target sequence 664, wherein the target sequence 664 is configured to attach to the analyte. Another oligonucleotide molecule 607 attached to the bead 604 comprises a second capture sequence 680 which is configured to attach to a second corresponding capture sequence 685. As illustrated in FIG. 6, the second corresponding capture sequence 685 is coupled to an antibody 682. In various cases, the antibody 682 may have binding specificity to an analyte (e.g., surface protein). Alternatively, the antibody 682 may not have binding specificity. Another oligonucleotide molecule 603 attached to the bead 604 comprises a third capture sequence 670 which is configured to attach to a second corresponding capture sequence 675. As illustrated in FIG. 6, the third corresponding capture sequence 675 is coupled to a molecule 672. The molecule 672 may or may not be configured to target an analyte. The other oligonucleotide molecules 603, 607 may comprise the other sequences (e.g., functional sequence, barcode sequence, UMI, etc.) described with respect to oligonucleotide molecule 605. While a single oligonucleotide molecule comprising each capture sequence is illustrated in FIG. 6, it will be appreciated that, for each capture sequence, the bead may comprise a set of one or more oligonucleotide molecules each comprising the capture sequence. For example, the bead may comprise any number of sets of one or more different capture sequences. Alternatively, or in addition, the bead 604 may comprise other capture sequences, e.g., a capture sequence configured to couple to extension product 1230 or amplicon thereof (e.g., FIGS. 12F-12L). Alternatively, or in addition, the bead 604 may comprise fewer types of capture sequences (e.g., two capture sequences). Alternatively, or in addition, the bead 604 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. See, e.g., PCT/US2014/044398, the disclosure of which is hereby incorporated by reference in its entirety.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. See, e.g., PCT/US2014/044398, the disclosure of which is hereby incorporated by reference in its entirety.

As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In various cases, a species (e.g., oligonucleotide molecules comprising barcodes) that are attached to a solid support (e.g., a bead) may comprise a U-excising element that allows the species to release from the bead. In various cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In various cases, the length of a barcode sequence may be about 6, 7, 8, 9, 10, 11, 12, 13, 14, 15, 16, 17, 18, 19, 20 nucleotides or longer. In various cases, the length of a barcode sequence may be at least about 6, 7, 8, 9, 10, 11, 12, 13, 14, 15, 16, 17, 18, 19, 20 nucleotides or longer. In various cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In various cases, separated barcode subsequences can be from about 4 to about 16 nucleotides in length. In various cases, the barcode subsequence may be about 4, 5, 6, 7, 8, 9, 10, 11, 12, 13, 14, 15, 16 nucleotides or longer. In various cases, the barcode subsequence may be at least about 4, 5, 6, 7, 8, 9, 10, 11, 12, 13, 14, 15, 16 nucleotides or longer. In various cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying nucleic acids (e.g., mRNA, the genomic DNA) from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, beads, such as beads, are provided that each include large numbers of the above-described nucleic acid barcode molecules releasably attached to the beads, where all of the nucleic acid barcode molecules attached to a particular bead will include a common nucleic acid barcode sequence, but where a large number of diverse barcode sequences are represented across the population of beads used. In various embodiments, hydrogel beads, e.g., comprising polyacrylamide polymer matrices, are used as a solid support and delivery vehicle for the nucleic acid barcode molecules into the partitions, as they are capable of carrying large numbers of nucleic acid barcode molecules, and may be configured to release those nucleic acid molecules upon exposure to a particular stimulus, as described elsewhere herein. In various cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. In various cases, the population of beads provides a diverse barcode sequence library that includes about 1,000 to about 10,000 different barcode sequences, about 5,000 to about 50,000 different barcode sequences, about 10,000 to about 100,000 different barcode sequences, about 50,000 to about 1,000,000 different barcode sequences, or about 100,000 to about 10,000,000 different barcode sequences.

Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in various cases at least about 1 billion nucleic acid molecules, or more. In various embodiments, the number of nucleic acid molecules including the barcode sequence on an individual bead is between about 1,000 to about 10,000 nucleic acid molecules, about 5,000 to about 50,000 nucleic acid molecules, about 10,000 to about 100,000 nucleic acid molecules, about 50,000 to about 1,000,000 nucleic acid molecules, about 100,000 to about 10,000,000 nucleic acid molecules, about 1,000,000 to about 1 billion nucleic acid molecules.

Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid barcode molecules, at least about 5,000 nucleic acid barcode molecules, at least about 10,000 nucleic acid barcode molecules, at least about 50,000 nucleic acid barcode molecules, at least about 100,000 nucleic acid barcode molecules, at least about 500,000 nucleic acids, at least about 1,000,000 nucleic acid barcode molecules, at least about 5,000,000 nucleic acid barcode molecules, at least about 10,000,000 nucleic acid barcode molecules, at least about 50,000,000 nucleic acid barcode molecules, at least about 100,000,000 nucleic acid barcode molecules, at least about 250,000,000 nucleic acid barcode molecules and in various cases at least about 1 billion nucleic acid barcode molecules.

In various cases, the resulting population of partitions provides a diverse barcode sequence library that includes about 1,000 to about 10,000 different barcode sequences, about 5,000 to about 50,000 different barcode sequences, about 10,000 to about 100,000 different barcode sequences, about 50,000 to about 1,000,000 different barcode sequences, or about 100,000 to about 10,000,000 different barcode sequences. Additionally, each partition of the population can include between about 1,000 to about 10,000 nucleic acid barcode molecules, about 5,000 to about 50,000 nucleic acid barcode molecules, about 10,000 to about 100,000 nucleic acid barcode molecules, about 50,000 to about 1,000,000 nucleic acid barcode molecules, about 100,000 to about 10,000,000 nucleic acid barcode molecules, about 1,000,000 to about 1 billion nucleic acid barcode molecules.

In various cases, it may be desirable to incorporate multiple different barcodes within a given partition, either attached to a single or multiple beads within the partition. For example, in various cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In various cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

V.E. Reagents:

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 410), such as through an additional channel or channels upstream of the channel junction. In accordance with other aspects, additionally or alternatively, biological particles may be partitioned along with other reagents, as will be described further below.

The methods and systems of the present disclosure may comprise microfluidic devices and methods of use thereof, which may be used for co-partitioning biological particles with reagents. Such systems and methods are described in U.S. Patent Publication No. US/20190367997, the disclosure of which is herein incorporated by reference in its entirety for all purposes.

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments of the microfluidic devices described elsewhere herein may be coupled to any of a variety of different fluid sources or receiving components, including reservoirs, tubing, manifolds, or fluidic components of other systems. As will be appreciated, the microfluidic channel structures may have various geometries and/or configurations. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in various cases, surfactant-based lysis solutions may be used to lyse cells, although these may be less desirable for emulsion-based systems where the surfactants can interfere with stable emulsions. In various cases, lysis solutions may include non-ionic surfactants such as, for example, TritonX-100 and Tween 20. In various cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion-based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., a cell or a nucleus in a polymer matrix), the biological particles may be exposed to an appropriate stimulus to release the biological particles or their contents from a co-partitioned bead. For example, in various cases, a chemical stimulus may be co-partitioned along with an encapsulated biological particle to allow for the degradation of the bead and release of the cell or its contents into the larger partition. In various cases, this stimulus may be the same as the stimulus described elsewhere herein for release of nucleic acid molecules (e.g., oligonucleotides) from their respective bead. In alternative examples, this may be a different and non-overlapping stimulus, in order to allow an encapsulated biological particle to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. No. 20190100632, the disclosures of which are hereby incorporated by reference in their entireties.

Additional reagents may also be co-partitioned with the biological particle, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching.

In various cases, template switching can be used to increase the length of a cDNA. In various cases, template switching can be used to append a predefined nucleic acid sequence to the cDNA. Template switching is further described in PCT/US2017/068320, the disclosure of which is hereby incorporated by reference in its entirety. Template switching oligonucleotides may comprise a hybridization region and a template region. Template switching oligonucleotides are further described in PCT/US2017/068320, the disclosure of which is hereby incorporated by reference in its entirety.

Any of the reagents described in this disclosure may be encapsulated in, or otherwise coupled to, a droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, and oligonucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles. In various aspects, this is performed by co-partitioning the individual biological particle or groups of biological particles with the unique identifiers, such as described above (with reference to FIG. 3 or 4).

In various cases, additional beads can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction. In such cases, the flow and frequency of the different beads into the channel or junction may be controlled to provide for a certain ratio of beads from each source, while ensuring a given pairing or combination of such beads into a partition with a given number of biological particles (e.g., one biological particle and one bead per partition).

V.F. Wells:

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In various instances, the wells or microwells may be configured to toggle between "open" and "closed" configurations. For instance, an "open" microwell or set of microwells may be "closed" or "sealed" using a membrane (e.g., semipermeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (μL), at most 100 μL, at most 10 μL, at most 1 μL, at most 100 nanoliters (nL), at most 10 nL, at most 1 nL, at most 100 picoliters (pL), at most 10 (pL), or less. The well may be configured to hold a volume of about 1000 µL, about 100 µL, about 10 µL, about 1 µL, about 100 nL, about 10 nL, about 1 nL, about 100 pL, about 10 pL, etc. The well may be configured to hold a volume of at least 10 pL, at least 100 pL, at least 1 nL, at least 10 nL, at least 100 nL, at least 1 µL, at least 10 µL, at least 100 µL, at least 1000 µL, or more. The well may be configured to hold a volume in a range of volumes listed herein, for example, from about 5 nL to about 20 nL, from about 1 nL to about 100 nL, from about 500 pL to about 100 µL, etc. The well may be of a plurality of wells that have varying volumes and may be configured to hold a volume appropriate to accommodate any of the partition volumes described herein.

In various instances, a microwell array or plate comprises a single variety of microwells. In various instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a droplet, bead, or other reagent. In various cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

Once sealed, the well may be subjected to conditions for further processing of a cell (or cells) in the well. For instance, reagents in the well may allow further processing of the cell, e.g., cell lysis, as further described herein. Alternatively, the well (or wells such as those of a well-based array) comprising the cell (or cells) may be subjected to freeze-thaw cycling to process the cell (or cells), e.g., cell lysis. The well containing the cell may be subjected to freezing temperatures (e.g., 0° C., below 0° C., −5° C., −10° C., −15° C., −20° C., −25° C., −30° C., −35° C., −40° C., −45° C., −50° C., −55° C., −60° C., −65° C., −70° C., −80° C., or −85° C.). Freezing may be performed in a suitable manner, e.g., sub-zero freezer or a dry ice/ethanol bath. Following an initial freezing, the well (or wells) comprising the cell (or cells) may be subjected to freeze-thaw cycles to lyse the cell (or cells). In one embodiment, the initially frozen well (or wells) are thawed to a temperature above freezing (e.g., 4° C. or above, 8° C. or above, 12° C. or above, 16° C. or above, 20° C. or above, room temperature, or 25° C. or above). In another embodiment, the freezing is performed for less than 10 minutes (e.g., 5 minutes or 7 minutes) followed by thawing at room temperature for less than 10 minutes (e.g., 5 minutes or 7 minutes). This freeze-thaw cycle may be repeated a number of times, e.g., 2, 3, 4 or more times, to obtain lysis of the cell (or cells) in the well (or wells). In one embodiment, the freezing, thawing and/or freeze/thaw cycling is performed in the absence of a lysis buffer. Additional disclosure related to freeze-thaw cycling is provided in WO2019165181A1, which is incorporated herein by reference in its entirety.

A well may comprise free reagents and/or reagents encapsulated in, or otherwise coupled to or associated with, beads, beads, or droplets.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In various cases, a well comprises a bead, or droplet that comprises a set of reagents that has a similar attribute (e.g., a set of enzymes, a set of minerals, a set of oligonucleotides, a mixture of different barcode molecules, a mixture of identical barcode molecules). In other cases, a bead or droplet comprises a heterogeneous mixture of reagents. In various cases, the heterogeneous mixture of reagents can comprise all components necessary to perform a reaction. In various cases, such mixture can comprise all components necessary to perform a reaction, except for 1, 2, 3, 4, 5, or more components necessary to perform a reaction. In various cases, such additional components are contained within, or otherwise coupled to, a different droplet or bead, or within a solution within a partition (e.g., microwell) of the system.

Figure 7:
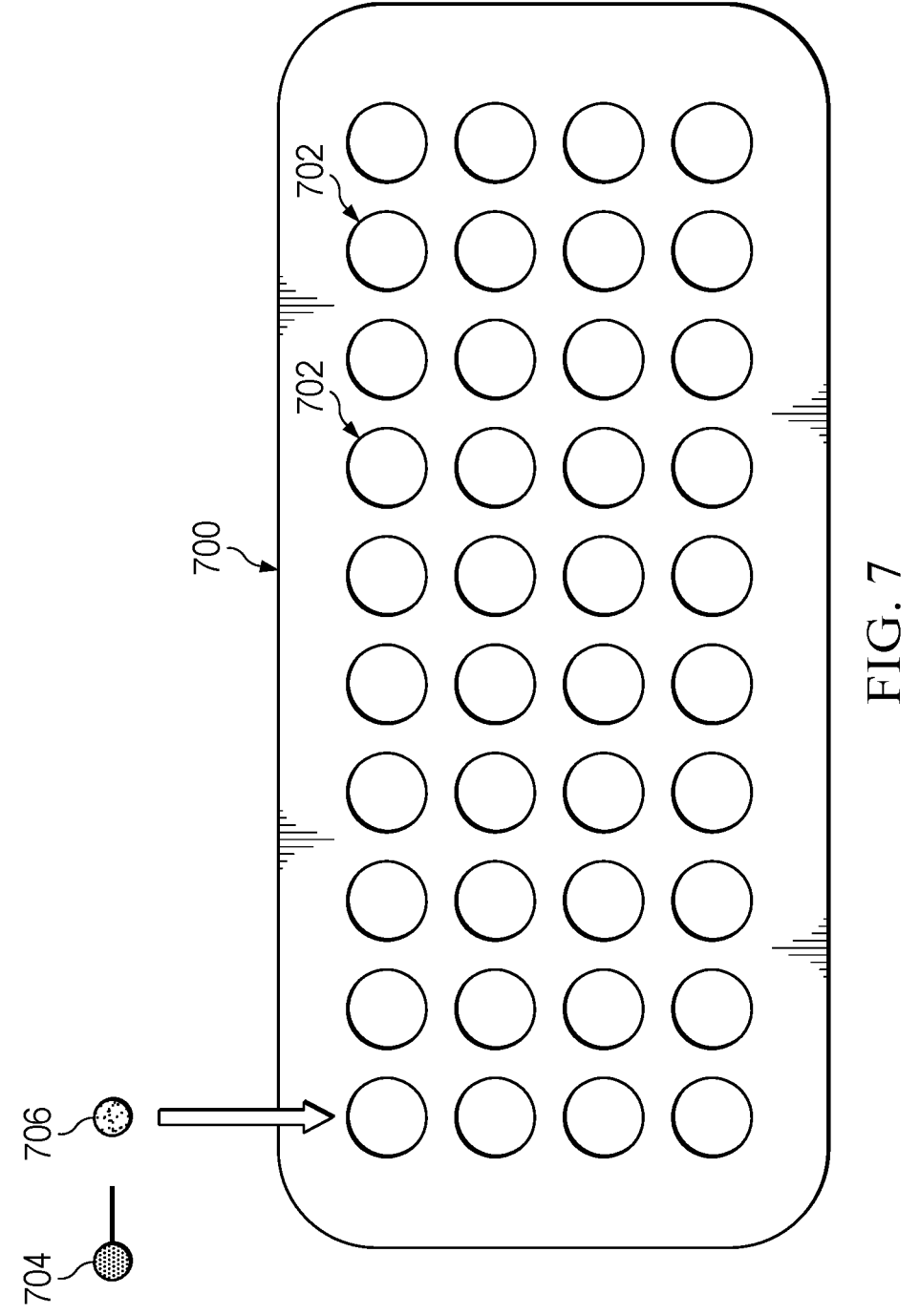
FIG. 7 is a schematic illustration of an example microwell array according to various embodiments.

FIG. 7 schematically illustrates an example of a microwell array. The array can be contained within a substrate 700. The substrate 700 comprises a plurality of wells 702. The wells 702 may be of any size or shape, and the spacing between the wells, the number of wells per substrate, as well as the density of the wells on the substrate 700 can be modified, depending on the particular application. In one such example application, a sample molecule 706, which may comprise a cell or cellular components (e.g., nucleic acid molecules) is co-partitioned with a bead 704, which may comprise a nucleic acid barcode molecule coupled thereto. The wells 702 may be loaded using gravity or other loading technique (e.g., centrifugation, liquid handler, acoustic loading, optoelectronic, etc.). In various instances, at least one of the wells 702 contains a single sample molecule 706 (e.g., cell) and a single bead 704.

Reagents may be loaded into a well either sequentially or concurrently. In various cases, reagents are introduced to the device either before or after a particular operation. In various cases, reagents (which may be provided, in certain instances, in droplets, or beads) are introduced sequentially such that different reactions or operations occur at different steps. The reagents (or droplets, or beads) may also be loaded at operations interspersed with a reaction or operation step. For example, beads (or droplets) comprising reagents for fragmenting polynucleotides (e.g., restriction enzymes) and/or other enzymes (e.g., transposases, ligases, polymerases, etc.) may be loaded into the well or plurality of wells, followed by loading of droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a bead, or droplet. These beads, or droplets may be loaded into a partition (e.g., a microwell) before, after, or concurrently with the loading of a cell, such that each cell is contacted with a different bead, or droplet. This technique may be used to attach a unique nucleic acid barcode molecule to nucleic acid molecules obtained from each cell. Alternatively, or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in various instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in various instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In various cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or bead may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In various instances, the wells can comprise nucleic acid barcode molecules attached thereto. The nucleic acid barcode molecules may be attached to a surface of the well (e.g., a wall of the well). The nucleic acid barcode molecules may be attached to a droplet or bead that has been partitioned into the well. The nucleic acid barcode molecule (e.g., a partition barcode sequence) of one well may differ from the nucleic acid barcode molecule of another well, which can permit identification of the contents contained with a single partition or well. In various cases, the nucleic acid barcode molecule can comprise a spatial barcode sequence that can identify a spatial coordinate of a well, such as within the well array or well plate. In various cases, the nucleic acid barcode molecule can comprise a unique molecular identifier for individual molecule identification. In various instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In various instances, the nucleic acid barcode molecules may be releasable from the microwell. In some instances, the nucleic acid barcode molecules may be releasable from the bead or droplet. For instance, the nucleic acid barcode molecules may comprise a chemical cross-linker which may be cleaved upon application of a stimulus (e.g., photo-, magnetic, chemical, biological, stimulus). The nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In some instances nucleic acid barcode molecules attached to a bead or droplet in a well may be hybridized to sample nucleic acid molecules, and the bead with the sample nucleic acid molecules hybridized thereto may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In various instances, imaging may be used to characterize live cells in the wells, including, but not limited to: dynamic live-cell tracking, cell-cell interactions (when two or more cells are co-partitioned), cell proliferation, etc. Alternatively, or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 8:
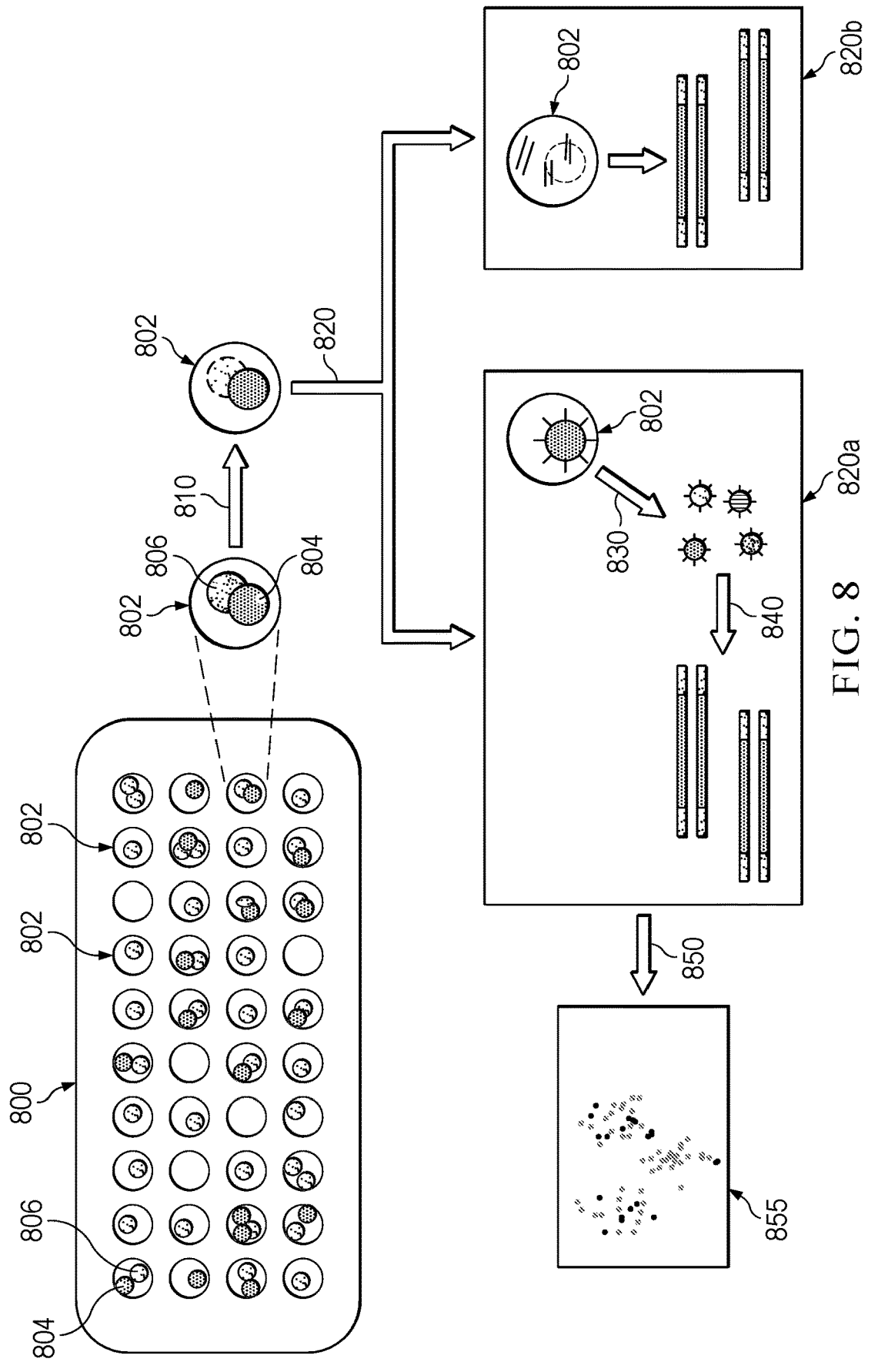
FIG. 8 is a schematic illustration of an example workflow for processing nucleic acid molecules according to various embodiments.

FIG. 8 schematically shows an example workflow for processing nucleic acid molecules within a sample. A substrate 800 comprising a plurality of microwells 802 may be provided. A sample 806 which may comprise a cell, cell bead, cellular components or analytes (e.g., proteins and/or nucleic acid molecules) can be co-partitioned, in a plurality of microwells 802, with a plurality of beads 804 comprising nucleic acid barcode molecules. During process 810, the sample 806 may be processed within the partition. For instance, in the case of live cells, the cell may be subjected to conditions sufficient to lyse the cells and release the analytes contained therein. In process 820, the bead 804 may be further processed. By way of example, processes 820*a* and 820*b* schematically illustrate different workflows, depending on the properties of the bead 804.

In 820*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 830, the beads 804 from multiple wells 802 may be collected and pooled. Further processing may be performed in process 840. For example, one or more nucleic acid reactions may be performed, such as reverse transcription, nucleic acid extension, amplification, ligation, transposition, etc. In various instances, adapter sequences are ligated to the nucleic acid molecules, or derivatives thereof, as described elsewhere herein. For instance, sequencing primer sequences may be appended to each end of the nucleic acid molecule. In process 850, further characterization, such as sequencing may be performed to generate sequencing reads. The sequencing reads may yield information on individual cells or populations of cells, which may be represented visually or graphically, e.g., in a plot 855.

In 820*b*, the bead comprises nucleic acid barcode molecules that are releasably attached thereto, as described below. The bead may degrade or otherwise release the nucleic acid barcode molecules into the well 802; the nucleic acid barcode molecules may then be used to barcode nucleic acid molecules within the well 802. Further processing may be performed either inside the partition or outside the partition. For example, one or more nucleic acid reactions may be performed, such as reverse transcription, nucleic acid extension, amplification, ligation, transposition, etc. In various instances, adapter sequences are ligated to the nucleic acid molecules, or derivatives thereof, as described elsewhere herein. For instance, sequencing primer sequences may be appended to each end of the nucleic acid molecule. In process 650, further characterization, such as sequencing may be performed to generate sequencing reads. The sequencing reads may yield information on individual cells or populations of cells, which may be represented visually or graphically, e.g., in a plot 855.

V.G. Targeted Enrichment

The methods provided herein may comprise the use of a targeting process to, for example, enrich selected nucleic acid molecules within a sample.

An exemplary target enrichment method may comprise providing a plurality of barcoded nucleic acid molecules and hybridizing barcoded nucleic acid molecules comprising targeted regions of interest to oligonucleotide probes ("baits") which are complementary to the targeted regions of interest (or to regions near or adjacent to the targeted regions of interest). Baits may be attached to a capture molecule, including without limitation a biotin molecule. The capture molecule (e.g., biotin) can be used to selectively pull down the targeted regions of interest (for example, with magnetic streptavidin beads) to thereby enrich the resultant population of barcoded nucleic acid molecules for those containing the targeted regions of interest.

V.H. Multiplexing:

The present disclosure provides methods and systems for multiplexing, and otherwise increasing throughput in, analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labelling agents capable of binding to or otherwise coupling to one or more cell features may be used to characterize biological particles and/or cell features. In various instances, labelling agents can include extension products 1230 or amplicons thereof. In various instances, cell features can include reaction products 1228. In various instances, cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In various instances, cell features may include intracellular analytes, such as proteins, protein modifications (e.g., phosphorylation status or other post-translational modifications), nuclear proteins, nuclear membrane proteins, or any combination thereof. A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have a first reporter oligonucleotide coupled thereto, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, the disclosures of which are incorporated by reference in their entireties for all purposes.

In a particular example, a library of potential cell feature labelling agents may be provided, where the respective cell feature labelling agents are associated with nucleic acid reporter molecules, such that a different reporter oligonucleotide sequence is associated with each labelling agent capable of binding to a specific cell feature. In various aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labelling agents capable of binding to or otherwise coupling to one or more biological particles may be used to characterize a biological particle as belonging to a particular set of biological particles. For example, labeling agents may be used to label a sample of cells or a group of cells. In this way, a group of cells may be labeled as different from another group of cells. In an example, a first group of cells may originate from a first sample and a second group of cells may originate from a second sample. Labelling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group.

For example, a reporter oligonucleotide may be linked to an antibody or an epitope binding fragment thereof, and labeling a biological particle may comprise subjecting the antibody-linked barcode molecule or the epitope binding fragment-linked barcode molecule to conditions suitable for binding the antibody to a molecule present on a surface of the biological particle. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as partitioning and/or nucleic acid amplification or extension. A dissociation constant (Kd) between the antibody or an epitope binding fragment thereof and the molecule to which it binds may be less than about 100 μM, 90 μM, 80 μM, 70 μM, 60 μM, 50 μM, 40 μM, 30

μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 μM.

In another example, a reporter oligonucleotide may be coupled to a cell-penetrating peptide (CPP), and labeling cells may comprise delivering the CPP coupled reporter oligonucleotide into a biological particle. Labeling biological particles may comprise delivering the CPP conjugated oligonucleotide into a cell and/or cell bead by the cell-penetrating peptide. A cell-penetrating peptide that can be used in the methods provided herein can comprise at least one non-functional cysteine residue, which may be either free or derivatized to form a disulfide link with an oligonucleotide that has been modified for such linkage. Non-limiting examples of cell-penetrating peptides that can be used in embodiments herein include penetratin, transportan, plsl, TAT(48-60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The cell-penetrating peptide may be an arginine-rich peptide transporter. The cell-penetrating peptide may be Penetratin or the Tat peptide.

In another example, a reporter oligonucleotide may be coupled to a fluorophore or dye, and labeling cells may comprise subjecting the fluorophore-linked barcode molecule to conditions suitable for binding the fluorophore to the surface of the biological particle. In various instances, fluorophores can interact strongly with lipid bilayers and labeling biological particles may comprise subjecting the fluorophore-linked barcode molecule to conditions such that the fluorophore binds to or is inserted into a membrane of the biological particle. In various cases, the fluorophore is a water-soluble, organic fluorophore. In various instances, the fluorophore is Alexa 532 maleimide, tetramethylrhodamine-5-maleimide (TMR maleimide), BODIPY-TMR maleimide, Sulfo-Cy3 maleimide, Alexa 546 carboxylic acid/succinimidyl ester, Atto 550 maleimide, Cy3 carboxylic acid/succinimidyl ester, Cy3B carboxylic acid/succinimidyl ester, Atto 565 biotin, Sulforhodamine B, Alexa 594 maleimide, Texas Red maleimide, Alexa 633 maleimide, Abberior STAR 635P azide, Atto 647N maleimide, Atto 647 SE, or Sulfo-Cy5 maleimide. See, e.g., Hughes L D, et al. PLoS One. 2014 Feb. 4; 9(2):e87649, which is hereby incorporated by reference in its entirety for all purposes, for a description of organic fluorophores.

A reporter oligonucleotide may be coupled to a lipophilic molecule, and labeling biological particles may comprise delivering the nucleic acid barcode molecule to a membrane of the biological particle or a nuclear membrane by the lipophilic molecule. Lipophilic molecules can associate with and/or insert into lipid membranes such as cell membranes and nuclear membranes. In various cases, the insertion can be reversible. In various cases, the association between the lipophilic molecule and biological particle may be such that the biological particle retains the lipophilic molecule (e.g., and associated components, such as nucleic acid barcode molecules, thereof) during subsequent processing (e.g., partitioning, cell permeabilization, amplification, pooling, etc.). The reporter nucleotide may enter into the intracellular space and/or a cell nucleus.

A reporter oligonucleotide may be part of a nucleic acid molecule comprising any number of functional sequences, as described elsewhere herein, such as a target capture sequence, a random primer sequence, and the like, and coupled to another nucleic acid molecule that is, or is derived from, the analyte.

Prior to partitioning, the cells may be incubated with the library of labelling agents, that may be labelling agents to a broad panel of different cell features, e.g., receptors, proteins, etc., and which include their associated reporter oligonucleotides. Unbound labelling agents may be washed from the cells, and the cells may then be co-partitioned (e.g., into droplets or wells) along with partition-specific barcode oligonucleotides (e.g., attached to a support, such as a bead or gel bead) as described elsewhere herein. As a result, the partitions may include the cell or cells, as well as the bound labelling agents and their known, associated reporter oligonucleotides.

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis (e.g., partition-based barcoding as described elsewhere herein). See, e.g., U.S. Pat. Pub. 20190323088, the disclosure of which is hereby incorporated by reference in its entirety for all purposes.

As described elsewhere herein, libraries of labelling agents may be associated with a particular cell feature as well as be used to identify analytes as originating from a particular biological particle, population, or sample. The biological particles may be incubated with a plurality of libraries and a given biological particle may comprise multiple labelling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labelling agents may allow multi-analyte, multiplexed analyses to be performed.

In various instances, these reporter oligonucleotides may comprise nucleic acid barcode sequences that permit identification of the labelling agent to which the reporter oligonucleotide is coupled. The use of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment), e.g., via a linker, using chemical conjugation techniques (e.g., LIGHTNING-LINK® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2): 708-715, which is entirely incorporated herein by reference for all purposes. Likewise, protein and peptide biotinylation techniques have been developed and are readily available. See, e.g., U.S. Pat. No. 6,265,552, the disclosure of which is incorporated by reference herein in its entirety for all purposes. Furthermore, click reaction chemistry such as a Methyltetrazine-PEG5-NHS Ester reaction, a TCO-PEG4-NHS Ester reaction, or the like, may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In various embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In various instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer biding sequence, a sequencing primer or primer biding sequence (such as an R1, R2, or partial R1 or R2 sequence).

In various cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In various cases, a label is conjugated to an oligonucleotide that is complementary to a sequence of the reporter oligonucleotide, and the oligonucleotide may be allowed to hybridize to the reporter oligonucleotide.

Figure 9:
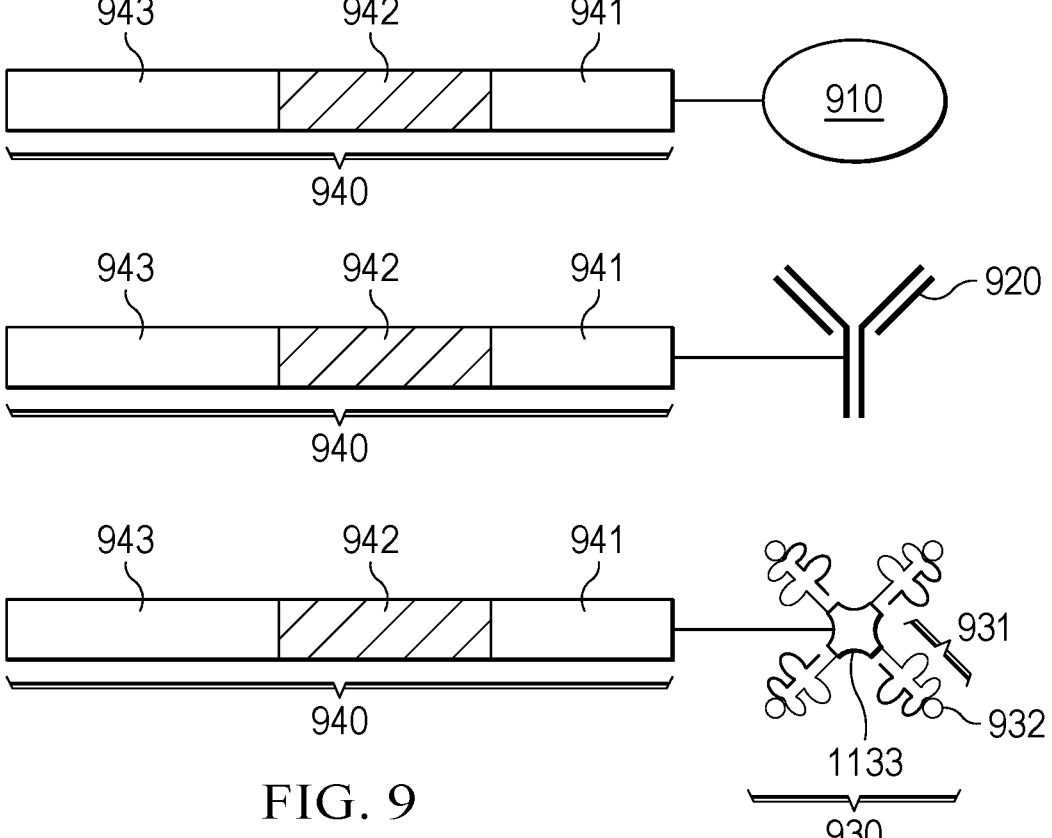
FIG. 9 is a schematic illustration of example labelling agents with nucleic acid molecules attached thereto according to various embodiments.

FIG. 9 describes exemplary labelling agents (910, 920, 930) comprising reporter oligonucleotides (940) attached thereto. Labelling agent 910 (e.g., any of the labelling agents described herein) is attached (either directly, e.g., covalently attached, or indirectly) to reporter oligonucleotide 940. Reporter oligonucleotide 940 may comprise barcode sequence 942 that identifies labelling agent 910. Reporter oligonucleotide 940 may also comprise one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, or a sequencing primer or primer binding sequence (such as an R1, R2, or partial R1 or R2 sequence).

Referring to FIG. 9, in various instances, reporter oligonucleotide 940 conjugated to a labelling agent (e.g., 910, 920, 930) comprises a functional sequence 941 (e.g., a primer sequence), a barcode sequence that identifies the labelling agent (e.g., 910, 920, 930), and functional sequence 943. Functional sequence 943 can be a reporter capture handle sequence configured to hybridize to a complementary sequence, such as a complementary sequence present on a nucleic acid barcode molecule 990 (not shown), such as those described elsewhere herein. In various instances, nucleic acid barcode molecule 990 is attached to a support (e.g., a bead, such as a gel bead), such as those described elsewhere herein. For example, nucleic acid barcode molecule 990 may be attached to the support via a releasable linkage (e.g., comprising a labile bond), such as those described elsewhere herein. In various instances, reporter oligonucleotide 940 comprises one or more additional functional sequences, such as those described above.

In various instances, the labelling agent 910 is a protein or polypeptide (e.g., an antigen or prospective antigen) comprising reporter oligonucleotide 940. Reporter oligonucleotide 940 comprises barcode sequence 942 that identifies polypeptide 910 and can be used to infer the presence of an analyte, e.g., a binding partner of polypeptide 910 (i.e., a molecule or compound to which polypeptide 910 can bind). In various instances, the labelling agent 910 is a lipophilic moiety (e.g., cholesterol) comprising reporter oligonucleotide 940, where the lipophilic moiety is selected such that labelling agent 910 integrates into a membrane of a cell or nucleus. Reporter oligonucleotide 940 comprises barcode sequence 942 that identifies lipophilic moiety 910 which in various instances is used to tag cells (e.g., groups of cells, cell samples, etc.) and may be used for multiplex analyses as described elsewhere herein. In various instances, the labeling agent is a reaction product 1228 comprising reporter oligonucleotide 940. In such instances, reporter oligonucleotide 940 can be or can include an extension product 1230. Reporter oligonucleotide 940 can include a reaction barcode sequence 942. In various instances, the labelling agent is an antibody 920 (or an epitope binding fragment thereof) comprising reporter oligonucleotide 940. Reporter oligonucleotide 940 comprises barcode sequence 942 that identifies antibody 920 and can be used to infer the presence of, e.g., a target of antibody 920 (i.e., a molecule or compound to which antibody 920 binds). In other embodiments, labelling agent 930 comprises an MHC molecule 931 comprising peptide 932 and reporter oligonucleotide 940 that identifies peptide 932. In various instances, the MHC molecule is coupled to a support 933. In various instances, support 933 may be a polypeptide, such as streptavidin, or a polysaccharide, such as dextran. In various instances, reporter oligonucleotide 940 may be directly or indirectly coupled to MHC labelling agent 930 in any suitable manner. For example, reporter oligonucleotide 940 may be coupled to MHC molecule 931, support 933, or peptide 932. In various embodiments, labelling agent 930 comprises a plurality of MHC molecules, (e.g. is an MHC multimer, which may be coupled to a support (e.g., 933)). There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., PRO5® MHC Class I Pentamers, (ProImmune, Ltd.), MHC octamers, MHC dodecamers, MHC decorated dextran molecules (e.g., MHC DEXTRAMER® (Immudex)), etc. For a description of exemplary labelling agents, including antibody and MHC-based labelling agents, reporter oligonucleotides, and methods of use, see, e.g., U.S. Pat. No. 10,550,429 and U.S. Pat. Pub. 20190367969, the disclosures of which are herein incorporated by reference in their entireties for all purposes.

FIG. 11 illustrates another example of a barcode carrying bead. In various embodiments, analysis of multiple analytes (e.g., RNA and one or more analytes using labelling agents described herein) may comprise nucleic acid barcode molecules as generally depicted in FIG. 11. In various embodiments, nucleic acid barcode molecules 1110 and 1120 are attached to support 1130 via a releasable linkage 1140 (e.g., comprising a labile bond) as described elsewhere herein. Nucleic acid barcode molecule 1110 may comprise adapter sequence 1111, barcode sequence 1112 and capture sequence 1113. Nucleic acid barcode molecule 1120 may comprise adapter sequence 1121, barcode sequence 1112, and capture sequence 1123, wherein capture sequence 1123 comprises a different sequence than capture sequence 1113. In various instances, adapter 1111 and adapter 1121 comprise the same sequence. In various instances, adapter 1111 and adapter 1121 comprise different sequences. Although support 1130 is shown comprising nucleic acid barcode molecules 1110 and 1120, any suitable number of barcode molecules comprising common barcode sequence 1112 are contemplated herein. For example, in various embodiments, support 1130 further comprises nucleic acid barcode molecule 1150. Nucleic acid barcode molecule 1150 may comprise adapter sequence 1151, barcode sequence 1112 and capture sequence 1153, wherein capture sequence 1153 comprises a different sequence than capture sequence 1113 and 1123. In various instances, nucleic acid barcode molecules (e.g., 1110, 1120, 1150) comprise one or more additional functional sequences, such as a UMI or other sequences described herein. The nucleic acid barcode molecules 1110, 1120 or 1150 may interact with analytes as described elsewhere herein, for example, as depicted in FIGS. 10A-C.

Figure 10A:
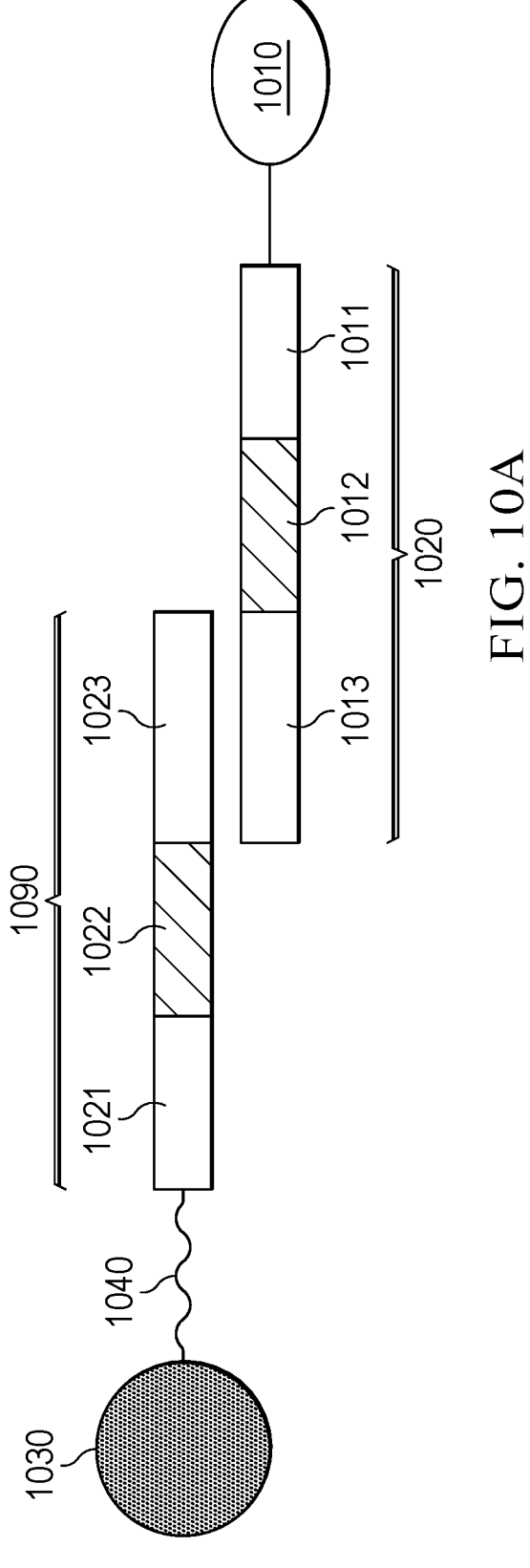
FIG. 10A is a schematic illustration of example labelling agents according to various embodiments.

Referring to FIG. 10A, in an instance where cells are labelled with labeling agents, capture sequence 1023 may be complementary to an adapter sequence of a reporter oligonucleotide. Cells may be contacted with one or more reporter oligonucleotide 1020 conjugated labelling agents 1010 (e.g., polypeptide, antibody, or others described elsewhere herein). In various cases, the cells may be further processed prior to barcoding. For example, such processing steps may include one or more washing and/or cell sorting steps. In various instances, a cell that is bound to labelling agent 1010 which is conjugated to oligonucleotide 1020 and support 1030 (e.g., a bead, such as a gel bead) comprising nucleic acid barcode molecule 1090 is partitioned into a partition amongst a plurality of partitions (e.g., a droplet of a droplet emulsion or a well of a microwell array). In various instances, the partition comprises at most a single cell bound to labelling agent 1010. In various instances, reporter oligonucleotide 1020 conjugated to labelling agent 1010 (e.g., polypeptide, an antibody, pMHC molecule such as an MHC multimer, etc.) comprises a first adapter sequence 1011 (e.g., a primer sequence), a barcode sequence 1012 that identifies the labelling agent 1010 (e.g., the polypeptide, antibody, or peptide of a pMHC molecule or complex), and an capture handle sequence 1013. Capture handle sequence 1013 may be configured to hybridize to a complementary sequence, such as a capture sequence 1023 present on a nucleic acid barcode molecule 1090. In various instances, oligonucleotide 1020 comprises one or more additional functional sequences, such as those described elsewhere herein.

Figure 10B:
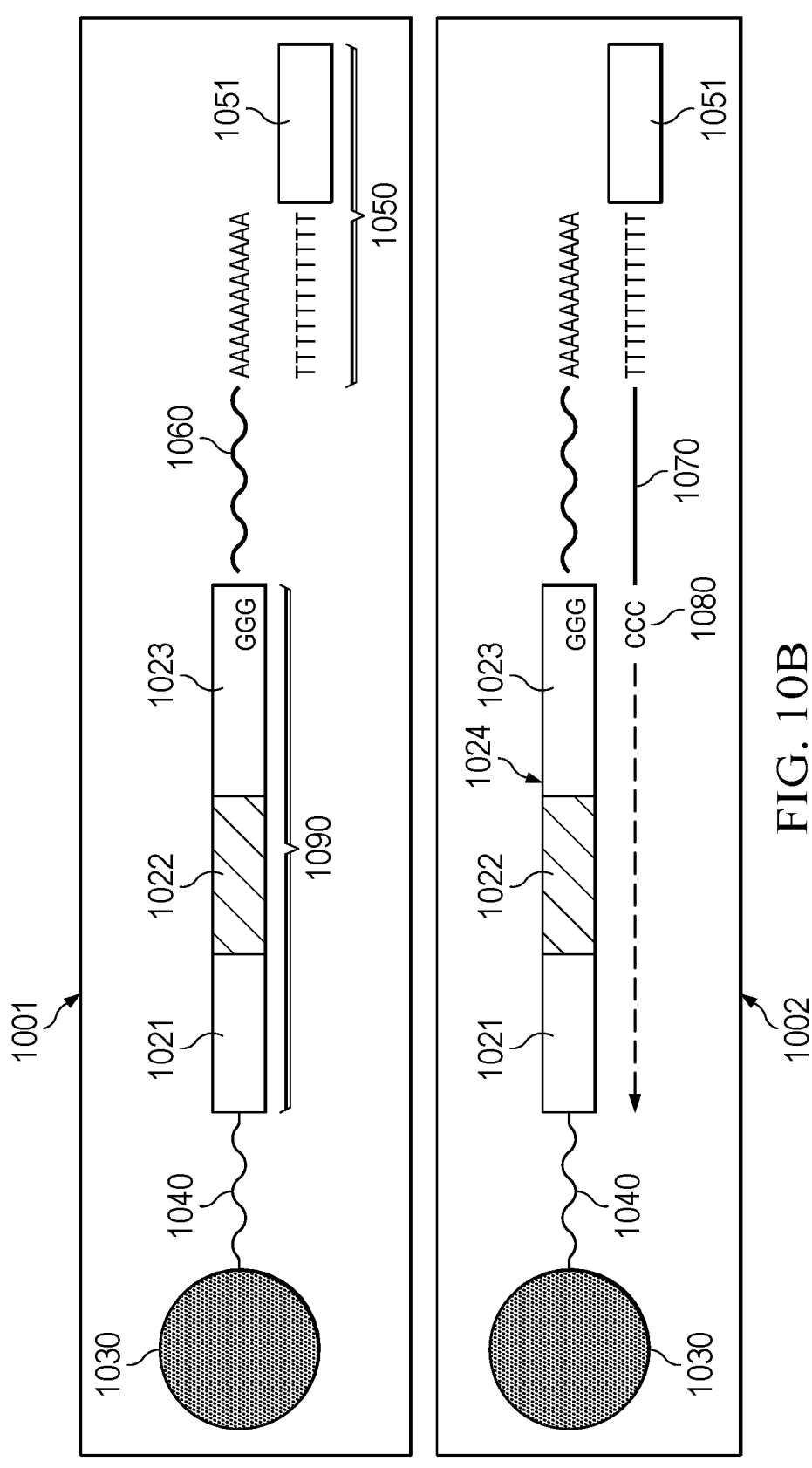
FIG. 10B schematically shows another example workflow for processing nucleic acid molecules according to various embodiments.
Figure 10C:
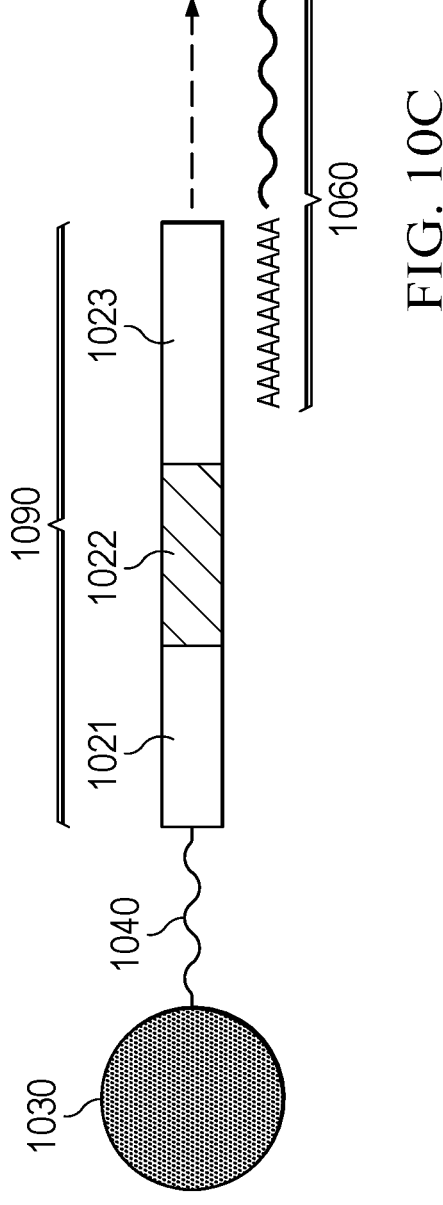
FIG. 10C schematically shows another example workflow for processing nucleic acid molecules according to various embodiments.

Barcoded nucleic acid molecules may be generated (e.g., via a nucleic acid reaction, such as nucleic acid extension or ligation) from the constructs described in FIGS. 10A-C. For example, capture handle sequence 1013 may then be hybridized to complementary sequence, such as capture sequence 1023 to generate (e.g., via a nucleic acid reaction, such as nucleic acid extension or ligation) a barcoded nucleic acid molecule comprising cell (e.g., partition specific) barcode sequence 1022 (or a reverse complement thereof) and reporter barcode sequence 1012 (or a reverse complement thereof). In various embodiments, the nucleic acid barcode molecule 1090 (e.g., partition-specific barcode molecule) further includes a UMI (not shown). Barcoded nucleic acid molecules can then be optionally processed as described elsewhere herein, e.g., to amplify the molecules and/or append sequencing platform specific sequences to the fragments. See, e.g., U.S. Pat. Pub. 2018/0105808, the disclosure of which is hereby incorporated by reference in its entirety herein for all purposes. Barcoded nucleic acid molecules, or derivatives generated therefrom, can then be sequenced on a suitable sequencing platform.

In various instances, analysis of multiple analytes (e.g., nucleic acids and one or more analytes using labelling agents described herein) may be performed. For example, the workflow may comprise a workflow as generally depicted in any of FIGS. 10A-C, or a combination of workflows for an individual analyte, as described elsewhere herein. For example, by using a combination of the workflows as generally depicted in FIGS. 10A-C, multiple analytes can be analyzed.

In various instances, analysis of an analyte (e.g. a nucleic acid, a polypeptide, a carbohydrate, a lipid, etc.) comprises a workflow as generally depicted in FIG. 10A. A nucleic acid barcode molecule 1090 may be co-partitioned with the one or more analytes. In various instances, nucleic acid barcode molecule 1090 is attached to a support 1030 (e.g., a bead, such as a gel bead), such as those described elsewhere herein. For example, nucleic acid barcode molecule 1090 may be attached to support 1030 via a releasable linkage 1040 (e.g., comprising a labile bond), such as those described elsewhere herein. Nucleic acid barcode molecule 1090 may comprise a functional sequence 1021 and optionally comprise other additional sequences, for example, a barcode sequence 1022 (e.g., common barcode, partition-specific barcode, or other functional sequences described elsewhere herein), and/or a UMI sequence (not shown). The nucleic acid barcode molecule 1090 may comprise a capture sequence 1023 that may be complementary to another nucleic acid sequence, such that it may hybridize to a particular sequence, e.g., capture handle sequence 1013.

For example, capture sequence 1023 may comprise a poly-T sequence and may be used to hybridize to mRNA. Referring to FIG. 10C, in various embodiments, nucleic acid barcode molecule 1090 comprises capture sequence 1023 complementary to a sequence of RNA molecule 1060 from a cell. In various instances, capture sequence 1023 comprises a sequence specific for an RNA molecule. Capture sequence 1023 may comprise a known or targeted sequence or a random sequence. In various instances, a nucleic acid extension reaction may be performed, thereby generating a barcoded nucleic acid product comprising capture sequence 1023, the functional sequence 1021, barcode sequence 1022, any other functional sequence, and a sequence corresponding to the RNA molecule 1060.

In another example, capture sequence 1023 may be complementary to an overhang sequence or an adapter sequence that has been appended to an analyte. For example, referring to FIG. 10B, panel 1001, in various embodiments, primer 1050 comprises a sequence complementary to a sequence of nucleic acid molecule 1060 (such as an RNA encoding for a BCR sequence) from a biological particle. In various instances, primer 1050 comprises one or more sequences 1051 that are not complementary to RNA molecule 1060. Sequence 1051 may be a functional sequence as described elsewhere herein, for example, an adapter sequence, a sequencing primer sequence, or a sequence the facilitates coupling to a flow cell of a sequencer. In various instances, primer 1050 comprises a poly-T sequence. In various instances, primer 1050 comprises a sequence complementary to a target sequence in an RNA molecule. In various instances, primer 1050 comprises a sequence complementary to a region of an immune molecule, such as the constant region of a TCR or BCR sequence. Primer 1050 is hybridized to nucleic acid molecule 1060 and complementary molecule 1070 is generated (see Panel 1002). For example, complementary molecule 1070 may be cDNA generated in a reverse transcription reaction. In various instances, an additional sequence may be appended to complementary molecule 1070. For example, the reverse transcriptase enzyme may be selected such that several non-templated bases 1080 (e.g., a poly-C sequence) are appended to the cDNA. In another example, a terminal transferase may also be used to append the additional sequence. Nucleic acid barcode molecule 1090 comprises a sequence 1024 complementary to the non-templated bases, and the reverse transcriptase performs a template switching reaction onto nucleic acid barcode molecule 1090 to generate a barcoded nucleic acid molecule comprising cell (e.g., partition specific) barcode sequence 1022 (or a reverse complement thereof) and a sequence of complementary molecule 1070 (or a portion thereof). In various instances, sequence 1023 comprises a sequence complementary to a region of an immune molecule, such as the constant region of a TCR or BCR sequence. Sequence 1023 is hybridized to nucleic acid molecule 1060 and a complementary molecule 1070 is generated. For example, complementary molecule 1070 may be generated in a reverse transcription reaction generating a barcoded nucleic acid molecule comprising cell (e.g., partition specific) barcode sequence 1022 (or a reverse complement thereof) and a sequence of complementary molecule 1070 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO2018/075693, U.S. Patent Publication No. 2018/0105808, U.S. Patent Publication No. 2015/0376609, filed Jun. 26, 2015, and U.S. Patent Publication No. 2019/0367969, the disclosures of which are herein incorporated by reference in their entireties for all purposes.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification can have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences can be varied and still remain within the spirit and scope of the various embodiments.

The invention claimed is:

1. A method for assessing enzymatic activity, the method comprising: combining a reactant barcoded oligonucleotide (RBO) construct with an amplification construct, a blocking construct, and an enzyme in a reaction mixture, wherein the reactant barcoded oligonucleotide (RBO) construct comprises:
    a first oligonucleotide comprising a reaction barcode sequence; and a first linker that connects the first oligonucleotide to a first reactant;
    wherein the amplification construct comprises:
        a second oligonucleotide that is complementary to at least a portion of the first oligonucleotide; and
        a second linker that connects the second oligonucleotide to a second reactant; and
    wherein the blocking construct comprises:
    a third oligonucleotide that is complementary to at least a portion of the first oligonucleotide;
enzymatically reacting the first reactant with the second reactant to produce a reaction product;
restricting movement of the amplification construct relative to the RBO construct; and
generating a reverse complement of the reaction barcode sequence with an amplification enzyme.

2. The method of claim 1, wherein generating a reverse complement of the reaction barcode sequence with an amplification enzyme comprises conducting an amplification reaction on the first oligonucleotide comprising the reaction barcode sequence to produce an extension product.

3. The method of claim 2, wherein the amplification reaction comprises the step of annealing a second adapter to a second adapter binding site adjacent to a 3' end of the reaction barcode sequence and generating a reverse complement of the reaction barcode sequence.

4. The method of claim 3, wherein the step of annealing further comprises annealing a first adapter to a first adapter binding site adjacent to a 5' end of the barcode sequence.

5. The method according to claim 2, wherein the amplification enzyme comprises a polymerase.

6. The method according to claim 2, wherein the amplification enzyme comprises a reverse transcriptase.

7. The method according to claim 1, further comprising:
    assessing an enzymatic activity of an enzyme based on an amplification product of the amplification reaction.

8. The method of claim 7, wherein the amplification product is detectable.

9. The method of claim 7, wherein the amplification product comprises a detectable label.

10. The method of claim 7, wherein the amplification product encodes a detectable label.

11. The method according to claim 2, further comprising:
    identifying the enzyme using the reaction barcode sequence.

12. The method according to claim 2, further comprising:
    modifying an amino acid sequence of the enzyme.

13. The method of claim 12, wherein the step of modifying occurs before combining the reactant barcoded oligonucleotide (RBO) construct with the amplification construct, the blocking construct, and the enzyme in the reaction mixture.

14. The method according claim 12, wherein modifying an amino acid sequence of the enzyme comprises a CRISPR-mediated amino acid sequence modification.

15. The method according to claim 1, wherein the first and second reactants each comprise a protein.

16. The method according to claim 1, wherein the first and second reactants each comprise a polynucleotide.

17. The method according to claim 1, further comprising:
increasing an affinity between the RBO construct and the
blocking construct.

18. The method according to claim 1, wherein the second oligonucleotide comprises at least one LNA.

19. The method according to claim 1, wherein the portion of the first oligonucleotide that is complementary to the second oligonucleotide comprises at least one LNA.

20. The method according to claim 1, wherein the second oligonucleotide comprises a non-reactive 3' end.

21. The method according to claim 1, wherein the reaction product comprises the first reactant covalently linked to the second reactant.

22. The method according to claim 1, wherein a quantity of the blocking construct is greater than a quantity of the amplification construct.

* * * * *